United States Patent
Kedia et al.

(10) Patent No.: US 11,440,014 B2
(45) Date of Patent: Sep. 13, 2022

(54) POINT OF CARE (POC) DEVICE FOR FACILITATING NUCLEIC ACID BASED TESTING AND METHOD THEREOF

(71) Applicant: INDIAN INSTITUTE OF TECHNOLOGY KHARAGPUR, West Bengal (IN)

(72) Inventors: Nandita Kedia, West Bengal (IN); Sujay Kumar Biswas, West Bengal (IN); Saptarshi Banerjee, West Bengal (IN); Aditya Bandopadhyay, West Bengal (IN); Arindam Mondal, West Bengal (IN); Suman Chakraborty, West Bengal (IN)

(73) Assignee: INDIAN INSTITUTE OF TECHNOLOGY KHARAGPUR, West Bengal (IN)

( * ) Notice: Subject to any disclaimer, the term of this patent is extended or adjusted under 35 U.S.C. 154(b) by 0 days.

(21) Appl. No.: 17/201,968

(22) Filed: Mar. 15, 2021

(65) Prior Publication Data
US 2022/0023867 A1    Jan. 27, 2022

(30) Foreign Application Priority Data
Jul. 23, 2020   (IN) .............................. 202031031597

(51) Int. Cl.
*B01L 7/00*   (2006.01)
*B01L 3/00*   (2006.01)
(Continued)

(52) U.S. Cl.
CPC .......... *B01L 7/52* (2013.01); *B01L 3/502715* (2013.01); *C12Q 1/686* (2013.01); *C12Q 1/6832* (2013.01);
(Continued)

(58) Field of Classification Search
None
See application file for complete search history.

(56) References Cited

U.S. PATENT DOCUMENTS

| 5,786,182 A * | 7/1998 | Catanzariti ............ B01L 3/502 |
| | | 422/417 |
| 7,595,381 B2 | 9/2009 | Minekawa |
| (Continued) | | |

FOREIGN PATENT DOCUMENTS

| CN | 111024954 A | 4/2020 |
| CN | 111187863 A | 5/2020 |
| CN | 111239400 A | 6/2020 |

OTHER PUBLICATIONS

Yiyue Ge et.al.; Rapid and Sensitive Detection of Novel Avian-Origin Influenza A (H7N9) Virus by Reverse Transcription Loop Mediated Isothermal Amplification Combined with a Lateral-Flow Device;PLOS ONE | www.plosone.org ,Aug. 2013 , vol. 8 ,Issue 8 , e69941.
(Continued)

*Primary Examiner* — Matthew D Krcha
(74) *Attorney, Agent, or Firm* — D'Ambrosio & Menon, PLLC; Usha Menon

(57) ABSTRACT

A generic point of care based portable device and method thereof as a platform technology for detecting pathogenic infection via nucleic acid based testing achieving sample-to-result integration, comprising the following interconnected stand-alone modules: a thermal unit for executing piece-wise isothermal reactions in a pre-programmable concomitant fashion without necessitating in-between operative intervention; a colorimetric detection unit seamlessly interfaced with smartphone-app based analytics for detecting the target analyte. The said platform technology is thus capable of detecting targeted pathogen-associated RNA by coupling additional complementary DNA probe hybridization com-
(Continued)

bined with isothermal reaction purposed for reverse transcription of RNA followed by amplification of the resulting c-DNA as well as subsequent specific binding of the same in a single user-step in a concomitant fashion and its smartphone-enabled interpretation, in a generic modular format that renders operative suitability outside controlled laboratory environment in a user-friendly manner, with predictive accuracy favorably comparable with gold standard RT-PCR tests.

20 Claims, 22 Drawing Sheets

Specification includes a Sequence Listing.

(51) Int. Cl.
  *C12Q 1/70* (2006.01)
  *G01N 33/543* (2006.01)
  *C12Q 1/6832* (2018.01)
  *C12Q 1/686* (2018.01)

(52) U.S. Cl.
  CPC ........ *C12Q 1/701* (2013.01); *G01N 33/54386* (2013.01); *B01L 2300/126* (2013.01); *B01L 2300/1805* (2013.01); *B01L 2300/1844* (2013.01); *G01N 2333/165* (2013.01)

(56) References Cited

U.S. PATENT DOCUMENTS

| | | | |
|---|---|---|---|
| 8,911,941 B2 | 12/2014 | Michlitsch | |
| 8,980,561 B1 | 3/2015 | Cai | |
| 2005/0208539 A1* | 9/2005 | Vann | B01L 3/502707 435/6.11 |
| 2007/0164211 A1* | 7/2007 | Flechsig | G01N 27/3276 250/288 |
| 2012/0264116 A1* | 10/2012 | Michlitsch | C12Q 1/6846 435/6.1 |
| 2014/0162244 A1* | 6/2014 | Bau | C12Q 1/703 435/5 |
| 2016/0195523 A1* | 7/2016 | Chatterjee | B01L 3/502784 435/6.1 |
| 2017/0096702 A1 | 4/2017 | Bau et al. | |
| 2020/0013488 A1 | 1/2020 | Lui et al. | |

OTHER PUBLICATIONS

Asmarani Kusumawati et.al.;Use of reverse transcription loop-mediated isothermal amplification combined with lateral flow dipstick for an easy and rapid detection of Jembrana disease virus;VirusDis. (Jul.-Sep. 2015) 26 (3):189-195.

Changping Xu et. al.;Rapid detection of measles virus using reverse transcription loop-mediated isothermal amplification coupled with a disposable lateral flow device;Diagnostic Microbiology and Infectious Disease ,85 (2016) 168-173.

Veronica L. Fowler et.al.;Development of a reverse transcription loop-mediated isothermal amplification assay for the detection of vesicular stomatitis New Jersey virus: Use of rapid molecular assays to differentiate between vesicular disease viruses;Journal of Virological Methods,234 (2016) 123-131.

Kattika Kaarj et.al.;Simpler, Faster, and Sensitive Zika Virus Assay Using Smartphone Detection of Loop-mediated Isothermal Amplifcation on Paper Microfuidic Chips;Scientific Reports | (2018) 8:12438 |.

Jinhui Li et.al.;Rapid and sensitive detection of Senecavirus A by reverse transcription loop-mediated isothermal amplification combined with a lateral flow dipstick method,PLOS ONE | https://doi.org/10.1371/journal.pone.0216245 May 2, 2019.p. 1-16.

Ashwin Ramachandran et .al.;Electric field-driven microfluidics for rapid CRISPR-based diagnostics and its application to detection of SARS-CoV-2,PNAS , Nov. 24, 2020 , vol. 117 ,No. 4729518-29525 |.

Anurup Ganguli et.al. ;Rapid isothermal amplification and portable detection system for SARS-CoV-2;PNAS | Sep. 15, 2020 , vol. 117 , No. 37, 22727-22735.

Julien Reboud et al.; Paper-based microfluidics for DNA diagnostics of malaria in low resource underserved rural communities,p. 4834-4842 ,PNAS ,Mar. 12, 2019 ,vol. 116 ,No. 11.

Huan Xu et. al.; An ultraportable and versatile point-of-care DNA testing platform,Sci. Adv. 2020; 6 : eaaz7445 Apr. 22, 2020, p. 1-10.

Kristina Roskos et. al.; Simple System for Isothermal DNA Amplification Coupled to Lateral Flow Detection,Plos One, 2013, p. 1-17;https://doi.org/10.1371/journal.pone.0069355.

Lisa K. Lafleur, et.al.;A rapid, instrument-free, sample-to-result nucleic acid amplification test, Royal Society of Chemistry, Lab Chip, 2016, 16, 3777-3787.

\* cited by examiner

A

B

C

D

SEQUENCE LISTING

<160> NUMBER OF SEQ ID NOS: 43

<210> SEQ ID NO 1
<211> LENGTH: 23
<212> TYPE: DNA
<213> ORGANISM: Artificial Sequence
<220> FEATURE:
<223> OTHER INFORMATION: Sequence of outer Forward primer F3 for ORF1b

<400> SEQUENCE: 1
gccattagtg caaagaatag agc                                              23

<210> SEQ ID NO 2
<211> LENGTH: 23
<212> TYPE: DNA
<213> ORGANISM: Artificial Sequence
<220> FEATURE:
<223> OTHER INFORMATION: Sequence of outer Backward primer B3 for ORF1b

<400> SEQUENCE: 2
ggcatggctc tatcacattt agg                                              23

<210> SEQ ID NO 3
<211> LENGTH: 42
<212> TYPE: DNA
<213> ORGANISM: Artificial Sequence
<220> FEATURE:
<223> OTHER INFORMATION: Sequence of Forward inner primer FIP(F1c+F2)5'-
      [Btn]for ORF1b

<400> SEQUENCE: 3
tagctcctct agtggcggct attgcaccgt agctggtgtc tc                         42

<210> SEQ ID NO 4
<211> LENGTH: 52
<212> TYPE: DNA
<213> ORGANISM: Artificial Sequence
<220> FEATURE:
<223> OTHER INFORMATION: Sequence of Backward inner primer
      BIP(B1c+B2)for ORF1b

<400> SEQUENCE: 4
tgtagtaatt ggaacaagca aattctatgg tggccaaccc ataaggtgag gg              52

<210> SEQ ID NO 5
<211> LENGTH: 37
<212> TYPE: DNA
<213> ORGANISM: Artificial Sequence
<220> FEATURE:
<223> OTHER INFORMATION: Sequence of Forward loop primer for ORF1b

<400> SEQUENCE: 5
tttttgatga aactgtctat tggtcatagt actacag                          37

<210> SEQ ID NO 6
<211> LENGTH: 36
<212> TYPE: DNA
<213> ORGANISM: Artificial Sequence
<220> FEATURE:
<223> OTHER INFORMATION: Sequence of Backward loop primer for ORF1b

<400> SEQUENCE: 6
ggcacaacat gttaaaaact gtttatagtg atgtag                           36

<210> SEQ ID NO 7
<211> LENGTH: 35
<212> TYPE: DNA
<213> ORGANISM: Artificial Sequence
<220> FEATURE:
<223> OTHER INFORMATION: Sequence of  BLP mod 5'-[6FAM]Probe for ORF1b

<400> SEQUENCE: 7
ttggcacaac atgttaaaaa ctgtttatag tgatg                            35

<210> SEQ ID NO 8
<211> LENGTH: 35
<212> TYPE: DNA
<213> ORGANISM: Artificial Sequence
<220> FEATURE:
<223> OTHER INFORMATION: Sequence of BLP mod 5'-[6FAM] 3'-[3d_G] Probe
      for ORF1b

<400> SEQUENCE: 8
ttggcacaac atgttaaaaa ctgtttatag tgatg                            35

<210> SEQ ID NO 9
<211> LENGTH: 33
<212> TYPE: DNA
<213> ORGANISM: Artificial Sequence
<220> FEATURE:
<223> OTHER INFORMATION: Sequence of FLP Probe mod 5'-[6FAM] for ORF1b

<400> SEQUENCE: 9
gcggctattg atttcaataa tttttgatga aac                              33

<210> SEQ ID NO 10
<211> LENGTH: 21
<212> TYPE: DNA
<213> ORGANISM: Artificial Sequence
<220> FEATURE:
<223> OTHER INFORMATION: Sequence of outer Forward primer F3 for N gene

<400> SEQUENCE: 10
acaatgtaac acaagctttc g                                           21

<210> SEQ ID NO 11
<211> LENGTH: 21
<212> TYPE: DNA
<213> ORGANISM: Artificial Sequence
<220> FEATURE:

<223> OTHER INFORMATION: Sequence of outer Backward primer B3for N gene

<400> SEQUENCE: 11
ttggatcttt gtcatccaat t                                              21

<210> SEQ ID NO 12
<211> LENGTH: 43
<212> TYPE: DNA
<213> ORGANISM: Artificial Sequence
<220> FEATURE:
<223> OTHER INFORMATION: Sequence of Forward inner primer(F1c+F2)5'-
      [Btn] for N gene

<400> SEQUENCE: 12
ggccaatgtt tgtaatcagt tccttagacg tggtccagaa caa                      43

<210> SEQ ID NO 13
<211> LENGTH: 38
<212> TYPE: DNA
<213> ORGANISM: Artificial Sequence
<220> FEATURE:
<223> OTHER INFORMATION: Sequence of Backward inner primer(B1c+B2) for N
      gene

<400> SEQUENCE: 13
gcttcagcgt tcttcggaat cacctgtgta ggtcaacc                            38

<210> SEQ ID NO 14
<211> LENGTH: 21
<212> TYPE: DNA
<213> ORGANISM: Artificial Sequence
<220> FEATURE:
<223> OTHER INFORMATION: Sequence of Forward loop primer for N gene

<400> SEQUENCE: 14
tggtccccaa aatttccttg g                                              21

<210> SEQ ID NO 15
<211> LENGTH: 19
<212> TYPE: DNA
<213> ORGANISM: Artificial Sequence
<220> FEATURE:
<223> OTHER INFORMATION: Sequence of Backward loop primer for N gene

<400> SEQUENCE: 15
cgcgcattgg catggaagt                                                 19

<210> SEQ ID NO 16
<211> LENGTH: 22
<212> TYPE: DNA
<213> ORGANISM: Artificial Sequence
<220> FEATURE:
<223> OTHER INFORMATION: Sequence of Backward loop probe 5'-[6FAM]for N
      gene

<400> SEQUENCE: 16
ttggcatgga agtcacacct tc                                             22

<210> SEQ ID NO 17
<211> LENGTH: 22
<212> TYPE: DNA
<213> ORGANISM: Artificial Sequence
<220> FEATURE:
<223> OTHER INFORMATION: Sequence of BLP mod Probe 5'-[6FAM]
      3'-[3d_C]for N gene

<400> SEQUENCE: 17
ttggcatgga agtcacacct tc                                              22

<210> SEQ ID NO 18
<211> LENGTH: 27
<212> TYPE: DNA
<213> ORGANISM: Artificial Sequence
<220> FEATURE:
<223> OTHER INFORMATION: Sequence of Forward loop Probe 5'-[6FAM] for N
      gene

<400> SEQUENCE: 18
gattagttcc tggtccccaa aatttcc                                         27

<210> SEQ ID NO 19
<211> LENGTH: 19
<212> TYPE: DNA
<213> ORGANISM: Artificial Sequence
<220> FEATURE:
<223> OTHER INFORMATION: Sequence of outer Forward primer F3 for E gene

<400> SEQUENCE: 19
ttgtaagcac aagctgatg                                                  19

<210> SEQ ID NO 20
<211> LENGTH: 23
<212> TYPE: DNA
<213> ORGANISM: Artificial Sequence
<220> FEATURE:
<223> OTHER INFORMATION: Sequence of outer Backward primer B3 for E gene

<400> SEQUENCE: 20
agagtaaacg taaaaagaag gtt                                             23

<210> SEQ ID NO 21
<211> LENGTH: 49
<212> TYPE: DNA
<213> ORGANISM: Artificial Sequence
<220> FEATURE:
<223> OTHER INFORMATION: Sequence of Forward inner primer(F1c+F2)5'-
      [Btn] for E gene

<400> SEQUENCE: 21
cgaaagcaag aaaaagaagt acgctagtac gaacttatgt actcattcg                 49

<210> SEQ ID NO 22
<211> LENGTH: 48
<212> TYPE: DNA
<213> ORGANISM: Artificial Sequence
<220> FEATURE:
<223> OTHER INFORMATION: Sequence of Backward inner primer(B1c+B2)for E
      gene

<400> SEQUENCE: 22
ggtattcttg ctagttacac tagccaagac tcacgttaac aatattgc                  48

<210> SEQ ID NO 23
<211> LENGTH: 25
<212> TYPE: DNA
<213> ORGANISM: Artificial Sequence
<220> FEATURE:
<223> OTHER INFORMATION: Sequence of Forward loop primer for E gene

<400> SEQUENCE: 23
attaacgtac ctgtctcttc cgaaa                                           25

```
<210> SEQ ID NO 24
<211> LENGTH: 25
<212> TYPE: DNA
<213> ORGANISM: Artificial Sequence
<220> FEATURE:
<223> OTHER INFORMATION: Sequence of Backward loop  primer for E gene

<400> SEQUENCE: 24
atccttactg cgcttcgatt gtgtg                                              25

<210> SEQ ID NO 25
<211> LENGTH: 25
<212> TYPE: DNA
<213> ORGANISM: Artificial Sequence
<220> FEATURE:
<223> OTHER INFORMATION: Sequence of Backward loop probe5'-[6FAM] for E
      gene

<400> SEQUENCE: 25
atccttactg cgcttcgatt gtgtg                                              25

<210> SEQ ID NO 26
<211> LENGTH: 25
<212> TYPE: DNA
<213> ORGANISM: Artificial Sequence
<220> FEATURE:
<223> OTHER INFORMATION: Sequence of BLP mod Probe 5'-[6FAM] 3'-[3d_G]
      for E gene

<400> SEQUENCE: 26
atccttactg cgcttcgatt gtgtg                                              25

<210> SEQ ID NO 27
<211> LENGTH: 28
<212> TYPE: DNA
<213> ORGANISM: Artificial Sequence
<220> FEATURE:
<223> OTHER INFORMATION: Sequence of Forward loop probe5'-[6FAM] for E
      gene

<400> SEQUENCE: 27
attaactatt aacgtacctg tctcttcc                                           28

<210> SEQ ID NO 28
<211> LENGTH: 17
<212> TYPE: DNA
<213> ORGANISM: Artificial Sequence
<220> FEATURE:
<223> OTHER INFORMATION: Sequence of outer Forward primer F3 for RNaseP
      gene

<400> SEQUENCE: 28
ttgatgagct ggagcca                                                       17

<210> SEQ ID NO 29
<211> LENGTH: 18
<212> TYPE: DNA
<213> ORGANISM: Artificial Sequence
<220> FEATURE:
<223> OTHER INFORMATION: Sequence of Backward  primer B3 for RNaseP gene

<400> SEQUENCE: 29
caccctcaat gcagagtc                                                      18

<210> SEQ ID NO 30
<211> LENGTH: 41
<212> TYPE: DNA
```

```
<213> ORGANISM: Artificial Sequence
<220> FEATURE:
<223> OTHER INFORMATION: Sequence of Forward inner primer(F1c+F2)5'-
      [Btn] for RNaseP gene

<400> SEQUENCE: 30
gtgtgaccct gaagactcgg ttttagccac tgactcggat c                    41

<210> SEQ ID NO 31
<211> LENGTH: 45
<212> TYPE: DNA
<213> ORGANISM: Artificial Sequence
<220> FEATURE:
<223> OTHER INFORMATION: Sequence of Backward inner primer(B1c+B2 for
      RNaseP gene

<400> SEQUENCE: 31
cctccgtgat atggctcttc gttttttttct tacatggctc tggtc               45

<210> SEQ ID NO 32
<211> LENGTH: 20
<212> TYPE: DNA
<213> ORGANISM: Artificial Sequence
<220> FEATURE:
<223> OTHER INFORMATION: Sequence of Forward loop primer for RNaseP gene

<400> SEQUENCE: 32
atgtggatgg ctgagttgtt                                            20

<210> SEQ ID NO 33
<211> LENGTH: 20
<212> TYPE: DNA
<213> ORGANISM: Artificial Sequence
<220> FEATURE:
<223> OTHER INFORMATION: Sequence of Backward loop primer for RNaseP
      gene

<400> SEQUENCE: 33
catgctgagt actggacctc                                            20

<210> SEQ ID NO 34
<211> LENGTH: 21
<212> TYPE: DNA
<213> ORGANISM: Artificial Sequence
<220> FEATURE:
<223> OTHER INFORMATION: Sequence of BLP probe 5'-[6FAM]for RNaseP gene

<400> SEQUENCE: 34
catgctgagt actggacctc g                                          21

<210> SEQ ID NO 35
<211> LENGTH: 20
<212> TYPE: DNA
<213> ORGANISM: Artificial Sequence
<220> FEATURE:
<223> OTHER INFORMATION: Sequence of FLP probe5'-[6FAM] for RNaseP gene

<400> SEQUENCE: 35
atgtggatgg ctgagttgtt                                            20

<210> SEQ ID NO 36
<211> LENGTH: 18
<212> TYPE: DNA
<213> ORGANISM: Artificial Sequence
<220> FEATURE:
<223> OTHER INFORMATION: Sequence of outer Forward primer F3 for FluA
      gene
```

<400> SEQUENCE: 36
gggctgtgac cactgaag                                                 18

<210> SEQ ID NO 37
<211> LENGTH: 20
<212> TYPE: DNA
<213> ORGANISM: Artificial Sequence
<220> FEATURE:
<223> OTHER INFORMATION: Sequence of outer Backward primer B3 for FluA
      gene

<400> SEQUENCE: 37
agcaatatcc atggcctctg                                               20

<210> SEQ ID NO 38
<211> LENGTH: 40
<212> TYPE: DNA
<213> ORGANISM: Artificial Sequence
<220> FEATURE:
<223> OTHER INFORMATION: Sequence of Forward inner primer (F1c+F2)5'-
      [Btn) for FluA gene

<400> SEQUENCE: 38
tgagaccgat gctgggagtc atggcatttg gcctggtatg                         40

<210> SEQ ID NO 39
<211> LENGTH: 41
<212> TYPE: DNA
<213> ORGANISM: Artificial Sequence
<220> FEATURE:
<223> OTHER INFORMATION: Sequence of Backward inner primer(B1c+B2) for
      FluA gene

<400> SEQUENCE: 39
tggttctagc caggagtaga gcctgcttgc tcactcgatc c                       41

<210> SEQ ID NO 40
<211> LENGTH: 21
<212> TYPE: DNA
<213> ORGANISM: Artificial Sequence
<220> FEATURE:
<223> OTHER INFORMATION: Sequence of Forward loop primer for FluA gene

<400> SEQUENCE: 40
gcaatctgtt cacaggttgc g                                             21

<210> SEQ ID NO 41
<211> LENGTH: 21
<212> TYPE: DNA
<213> ORGANISM: Artificial Sequence
<220> FEATURE:
<223> OTHER INFORMATION: Sequence of Backward loop primer for FluA gene

<400> SEQUENCE: 41
taaggctatg gagcaaatgg c                                             21

<210> SEQ ID NO 42
<211> LENGTH: 22
<212> TYPE: DNA
<213> ORGANISM: Artificial Sequence
<220> FEATURE:
<223> OTHER INFORMATION: Sequence of Backward loop probe5'-[6FAM] for
      FluA gene

<400> SEQUENCE: 42

-continued

```
taaggctatg gagcaaatgg ct                                            22

<210> SEQ ID NO 43
<211> LENGTH: 21
<212> TYPE: DNA
<213> ORGANISM: Artificial Sequence
<220> FEATURE:
<223> OTHER INFORMATION: Sequence of Forward loop probe5'-[6FAM] for
      FluA gene

<400> SEQUENCE: 43
gcaatctgtt cacaggttgc g                                             21
```

POINT OF CARE (POC) DEVICE FOR FACILITATING NUCLEIC ACID BASED TESTING AND METHOD THEREOF

CROSS-REFERENCE TO RELATED APPLICATIONS

This application is related to and claims priority to Indian Patent Application No. 202031031597 filed on Jul. 23, 2020, the contents of which are incorporated by reference herein.

INCORPORATION BY REFERENCE

This application includes a sequence listing in computer readable form (a "txt" file) that is submitted herewith on ASCII text file named SeqList.txt, created on Mar. 15, 2021 and 10,210 bytes in size. This sequence listing is incorporated by reference herein.

FIELD OF THE INVENTION

The present invention relates to a portable low-cost point of care (POC) diagnostic device for the detection of pathogenic infection via nucleic acid-based testing. More specifically, the detection method by the said POC device includes selectively piecewise isothermal reaction steps in a pre-programmable format with no intermediate manual intervention, concomitantly executing a compatible detection and read-out. The said device comprises modular thermal control cum reaction unit for running the test protocol on clinical samples (patient's body fluid mixed with test reagents) or any other sample for In-vitro analysis; exclusive detection unit comprising functionalized paper substrates conjugated with surface plasmon resonating nano-materials and immobilized bio-conjugates for colorimetric visualization of the reaction products and smartphone-enabled image analytic unit for dissemination of the test outcome without necessitating manual interpretation, all seamlessly integrated in a portable box having scalable dimensions that can be operated without specialized infrastructural support and technicians. Advantageously, the device of the present invention finds application in health care fields for rapid and efficient detection of a plethora of bacterial, viral and parasitic infections premised on nucleic-acid based testing, inclusive of, but not limited to COVID-19, Dengue, Influenza, Malaria, Tuberculosis, cost effectively without involving the conventionally used expensive instruments and skilled human resources.

BACKGROUND ART

Molecular diagnostic test relies upon detection of pathogen associated molecular targets like genetic materials (DNA or RNA), antigens or corresponding antibodies in appropriate body fluid samples. Point-of-care (POC) immunoassays, alternatively known as rapid diagnostic tests (RDTs), targeting the viral antigens or antibodies in the patient sample, are extremely attractive for deployment in resource limited settings. However, these techniques demonstrate limited accuracy, specifically at the early stage of infection, owing to the limited abundance of the pathogenic antigens or antibodies, and rapid genetic evolution of pathogenic strains.

In sharp contrast, the nucleic acid amplification-based tests (NAATs), detecting most fundamental signature of infection, provide a highly sensitive, accurate and reliable approach for diagnoses. The RT-qPCR technique, based on this concept, detects genomic RNA by reverse transcribing and amplifying into large number of complementary DNA molecules and monitoring the amplification reaction in real time with specific DNA based fluorescent probes. Owing to its high sensitivity and specificity, RT-PCR method is an established laboratory gold-standard for probing pathogenic RNAs. However, this mode of detection requires costly high-end RT-PCR machine that should be housed in highly sophisticated laboratory and demands highly trained laboratory personnel owing to the complexity of the protocol and data analysis associated. This limits the large-scale dissemination of this technique into resource-limited settings.

Circumventing the limitations mentioned in the aforesaid diagnostic methods, it is imperative to develop a sample-to-result integrable, portable, and low-cost, POC device which can rapidly detect pathogenic nucleic acids without compromising on the predictive capability in terms of sensitivity and specificity in comparison to gold standard PCR based results. More importantly, the said device needs to have the capability of performing the entire analysis up to result dissemination in an integrated easy-to-handle low-cost portable unit without further intervention by the user. Such a proposition holds utilitarian importance in performing mass screening tests for diagnosing highly infectious diseases over community levels even at extremely resource-poor settings, yet maintaining high standards of accuracy of the test results.

Isothermal nucleic acid amplification techniques (INAAT), including loop-mediated isothermal amplification (LAMP), multiple cross displacement amplification, cross-priming amplification, helicase-dependent amplification (HAD), recombinase polymerase amplification (RPA), and a few others, have emerged as potential alternatives to the RT-PCR test. The most attractive proposition of INAAT lies in obviating the need of complex thermal cycling, by adhering to isothermal reaction steps. Amongst INAATs, the RT-LAMP technique has emerged as one among the most versatile methods in recent times, for the detection of a wide variety of pathogens. The RT-LAMP reactions are simple, rapid and extremely targeted to identify six to eight regions on the template RNA sequence for amplification. As opposed to the RT-PCR test, the RT-LAMP test may be performed by using a smaller and simpler platform, requiring only a heat block in principle. Moreover, the reagents are stable and inhibitor-tolerant, so that, unlike RT-PCR, no purification steps are required. However, the major disadvantage of the RT-LAMP method is its indirect mode of detection that relies either upon change in turbidity of the reaction mixture or nonspecific dyes that respond to the change in the pH or free magnesium ion concentration. This may often produce ambiguous results that are difficult to interpret and hence restrict extensive clinical application of RT-LAMP for detection of pathogen associated nucleic acids. Another compelling challenge that has largely prohibited the INAAT tests to be deployed for community-level testing is the lack of a simple, user-friendly low-cost yet generic, robust instrument that can seamlessly couple any arbitrary isothermal reaction steps customizable with the test protocol with minimal manual steps.

In an effort to circumvent some of these constraints, the classical RT-LAMP method has been augmented with the CRISPR-Cas12/13 based detection technology. This method relies upon specific recognition of the RT-LAMP products by single guide RNA (sgRNA), subsequent activation of Cas12/13 to cleave the reporter DNA/RNA molecules and final detection of the reporter molecules (cleaved or uncleaved) using a lateral flow assay (LFA) strip or fluorescence detector. However, the sgRNA-mediated detection steps of CRISPR-based technology, when implemented outside controlled laboratory set-up, may result in false test outcomes owing to the high abundance of RNase that can degrade either the sgRNA or the dual labelled RNA probes (specifically in case of Cas13 based procedure). Additionally, the sgRNA-Cas12/13 complex should be freshly prepared (not earlier than 24 hours of conducting the test) before conducting the detection procedure, adding procedural complicacy to the overall test method. Further, the implementation of CRISPR based detection as a separate step necessitates in-between intervention, thereby increasing the chances of carryover contamination. Therefore, a different improvisation of the RT-LAMP technique merits innovation, retaining the simplicity of the RT-LAMP backbone, but augmenting it with further probing steps to iron out any potential deficits in specificity and sensitivity, and integrating all the necessary steps in a portable low-cost device unit that may be potentially functional with minimal resources.

Ge et al. (https://doi.org/10.1371/journal.pone.0069941) have developed LAMP-LFD (Lateral Flow Dipstick) based assay system for the rapid detection of an avian origin Influenza-A virus of the H7N9 subtype that causes disease in humans. They designed RT-LAMP primers targeting the HA and NA gene segments, including FITC-labelled LF primers and biotinylated LB primers, for each set so that the amplicons from a positive RT-LAMP reaction are specifically tagged and can generate a visible test line on a lateral flow platform for rapid detection in diagnostic or surveillance applications. The RT-LAMP-LFD assay was as sensitive as real-time RT-LAMP turbidity detection, with the limit of detection being 10 copies of synthetic viral RNA for both targets. Clinical sample-based validation data using 80 patient specimen showed complete specificity for the H7N9 subtype with 100% accuracy.

Kusumawati et al. (https://doi.org/10.1007/s13337-015-0277-5) have developed LAMP-LFD based assay system for the rapid detection of Jembrena Disease Virus (JDV), a viral pathogen of Bali cattle with high mortality, from organs and blood of infected cattle. They designed RT-LAMP primers (with 5'-biotinylated FIP) targeting the conserved tm subunit of JDV env gene and 5'-6FAM labelled specific DNA probes for hybridization-based detection on a lateral flow platform. Their LAMP-LFD assay was 100 times more sensitive than RT-PCR, with a limit of detection of $2 \times 10^{-15}$ g of template DNA.

Xu et al. (https://doi.org/10.1016/j.diagmicrobio.2016.02.023) have developed LAMP-LFD based assay system for the rapid detection of Measles virus (MeV). They designed RT-LAMP primers (with 5'-biotinylated FIP) targeting the conserved region of H gene and 5'-FITC labelled specific DNA probes for hybridization-based detection on a lateral flow platform. The limit of detection was 10 copies/µL of synthetic viral RNA, which was comparable to the sensitivity of real-time RT-PCR and their patient sample validation data (around 500 samples) using RT LAMP-LFD vs RT-PCR was highly concordant.

Fowler et al. (https://doi.org/10.1016/j.jviromet.2016.04.012) have developed LAMP-LFD based assay system for the rapid, specific detection of Vesicular stomatitis virus (VSV), of the New Jersey (VSNJ) serotype. They further developed a multiplex RT-LAMP assay to distinguish VSV from other viruses that cause vesicular disease in cattle with common clinical symptoms, namely, FMDV and SVDV, without prior RNA extraction from epithelial suspension samples. They designed RT-LAMP primers (with 5'-biotinylated BIP) targeting the junction between nucleocapsid (N) and phopshoprotein (P) genomic regions, including a 5'-fluorescein labelled FIP primer and a 5'-biotinylated BIP primer for the visual detection of LAMP amplicons by immune-chromatography based LFD.

Kaarj et al. (https://doi.org/10.1038/s41598-018-30797-9) have developed a RT-LAMP based assay for rapid and sensitive detection of Zika virus directly from biological samples (tap water, urine and plasma) on a paper microfluidic chip. The disposable chip platform was optimized for adequate filtration of the samples during capillary action-driven flow, allowing separation and subsequent excision of Zika virus RNA on reaching the detection area, which was subsequently applied to a RT-LAMP mixture followed by colorimetric detection of positive reactions. The limit of detection was as low as 1 copy/µL. The assay was also coupled with quantitative smartphone imaging for real-time monitoring of the colour change during the reaction.

Li et al. (https://doi.org/10.1371/journal.pone.0216245) have developed LAMP-LFD based assay system for the rapid detection of Seneca virus A (SVA) which is difficult to distinguish from other classical vesicular disease-causing viruses (eg: FMD, SVD) based only on clinical symptoms. They designed RT-LAMP primer sets targeting the conserved region of SVA 3D genomic region including a 5'-biotinylated FIP primer and a 5'-FITC labelled BIP primer for the visual detection of LAMP amplicons by LFD on a paper strip. The assay was demonstrated to be specific for SVA, with a detection limit of 4.5×10-8 ng/µ that was 10 times more sensitive than conventional RT-PCR.

Ramachandran et al. (https://doi.org/10.1073/pnas.2010254117) have reported an electric field gradient using selective ionic focusing technique for CRISPR-Cas12 enzyme-based detection of COVID 19 RNA in a microfluidic device. In this work, the authors have used isotachophoresis (ITP) for extraction, purification of the nucleic acid and control the CRISPR-Cas-12 activity for targeted DNA for detection. The LAMP-based amplification was performed in a tube after extraction of the nucleic acid using ITP technique. The fluorescent-based detection procedure was performed using an inverted epifluorescence microscope. Even though the assay procedure required very small amount of reagents and relatively less detection time of 30 minutes, it inherits some limitations with multiple intermediate manual steps for sample lysis and tube-based LAMP reaction. Moreover, this assay requires high voltage source meter to apply 1 kV for the isotachophoresis process in a specialized microfluidic chip, which adds further complexity in device and method. Furthermore, this method is yet to be tested in the form of an integrated device.

Ganguli et al. (https://doi.org/10.1073/pnas.2014739117) have demonstrated a fluorescent-based portable system for colorimetric detection of SARS-CoV-2 virus using nasal swab sample. The device consists of a 3D printed portable structure fitted with an isothermal heating arrangement, a setup for fluorescent light emission and a smartphone-based image capturing facilities. Two injection syringes (1 ml and 5 ml) are used for injecting the lysed sample and the RT-LAMP reagents separately into a polymer made microfluidic cartridge for mixing and subsequent isothermal heating. The heating unit includes a positive temperature coefficient (PCT) heater, a printed circuit board (PCB) and a battery for power supply. The fluorescent-based detection arrangement is equipped with long pass filters, short pass filters and blue light emitting diode (LED)s to excite the EvaGreen dye. The smartphone is used to capture images which are analysed using ImageJ software and data processing is done using MATLAB. Though this work has been claimed as a POC device, the entire process of sample collection to results display is not performed on a single platform. The sample preparation with cell lysis and also the image processing for analysis have been performed separately. Moreover, in this assay procedure, substantial volume of LAMP reagent is required as the reagent is injected into the microchamber using a 5 ml syringe.

Reboud et al. (https://doi.org/10.1073/pnas.1812296116) have developed a LAMP-based malaria detection platform using origami paper microfluidics combined with lateral flow assay technique. In this work, the origami paper assembly is used for DNA extraction from the sample followed by binding with beads and then distribution of the washed bead-bound DNA to the amplification unit. The plastic microfluidic platform consists of four finger pumping buffer chambers, four LAMP reaction and amplification units and a set of distribution channels to the four lateral flow strips. The DNA amplification is performed on the plastic microfluidic chamber and subsequently released to the later flow strips using paper-based valves. An electric-powered hot plate is used for isothermal heating of the DNA for amplification. Image capturing is performed using a smartphone and post-processing is done using ImageJ software. In this work, a method has been demonstrated where sample lysis is performed separately (not in the device). Image processing step is performed in a computer and also the isothermal heating is done using a separate hot plate.

Xu et al. (https://advances.sciencemag.org/lookup/doi/10.1126/sciadv.aaz7445) have reported an ultraportable POC device for DNA amplification and detection in which isothermal heating (37° C.) is provided from smartphone. The device is made of two components: a vertical unit for sample preparation and DNA amplification in a 3D printed structure and a foldable box for smartphone based detection. The sample preparation is done using a DNA extraction paper and the sample amplification is performed in a glass-PDMS microchannel. A smartphone app has been developed for heat generation and temperature control for incubation of the DNA sample at a temperature of 37° C. Though this particular assay can be performed using the smartphone generated heat for isothermal amplification at 37° C., the same heating procedure may not be implementable for the requirement of higher temperature such as 65° C. for LAMP amplification. Moreover, the glass-PDMS channel used for DNA amplification with probe-modified glass surface adds inevitable complexity in the manufacturing procedure.

Roskos et al. (https://dx.plos.org/10.1371/journal.pone.0069355) have reported a fully integrated POC device for DNA amplification and lateral flow assay (LFA) based detection in a contamination-free closed pouch. The disposable cartridge consists of two paper strips at the top connected with two pouch reaction chambers in the middle and another two pump pouches at the bottom. The pump pouch is filled with electrolyte solution for electrolysis which provides pumping of the amplified DNA solution upwards to the lateral flow strips. A thin-film polyimide heater is attached to the bottom of an aluminium plate which acts as a heating surface of the device. Due to the electrolytic pumping of the amplified solution to the LFA, the reaction mixture transports through the paper by capillary action and produces a colorimetric signal for visual readout. Though the work has been presented as a POC device, it does not achieve sample-to-result integration. Additionally, considering the complexity of the pouch-based cartridge, the cost of the disposable cartridge and machine unit may not be suitable for implementation in POC setup.

Lafleur et al. (http://xlink.rsc.org/?DOI=C6LC00677A) have demonstrated an integrated POC as well as disposable system for sample processing, nucleic acid amplification to colorimetric detection of bacteria from nasal swab. The sample chamber is fabricated with syringe, rubber tube, heating arrangement and graphene wax block. The sample processing is done by incubating with an enzyme mixture for bacterial cell lysis followed by heating at 95° C. for 10 minutes for denaturation. The lysed sample is transported to the paper-based amplification chamber by melting the wax block into the rubber tube using point heating mechanism. After isothermal amplification of the fluid into the paper-PMMA chamber, the amplified solution is transported through the paper network by melting another wax valve set after the amplification chamber. The colorimetric detection of the lateral flow strip is done using a flatbed scanner and computer-based ImageJ software, restricting the device integration in the framework of a smartphone integrated stand-alone POC unit. Since the entire device is disposable and for one-time use, consumables per test are substantial and manufacturing scale-up is not realizable.

U.S. Pat. No. 8,980,561B1 has disclosed a rapid, sensitive, and specific nucleic acid detection method for influenza viruses using isothermal amplification and colorimetric detection with LFA strip. The functionality of the reported invention includes extraction of target RNA from clinical samples using immunomagnetic affinity capture, specific amplification of the target sequence with hybridization and colorimetric detection with lateral flow strip and visual readout device. This prior patent, while detailing a complete detection process, does not mention any device which might have been used for isothermal heating. The entire process of sample preparation steps followed by isothermal amplification has done in a single reaction vessel.

US20170096702A1 has disclosed a microfluidic cassette for the extraction of nucleic acid from the collected sample followed by isothermal amplification and fluorescent base detection in real-time. For capturing, isolation and concentrating the nucleic acid, the inventor has used a special silica-based membrane in the device. This prior art demonstrated the device for detection of HIV from oral fluid with sensitivity of 10 HIV particles per sample. The isothermal heating is provided by a thin film heater to the PMMA made reaction chamber. A portable fluorescent base reader is used for real-time monitoring and detection of the amplified nucleic acid. Despite certain merits, this invention does not provide sample-to-answer integration in a POC format. U.S. Pat. No. 8,911,941 has reported a fully integrated sample-to-answer point-of-care molecular diagnostic method and apparatus for nucleic acid amplification and colorimetric detection. This apparatus is similar in kind of a digital home pregnancy test kit. The sample preparation with this apparatus is done using heat treatment and chemically treated filter paper. Subsequently this sample-contained filter paper is transported to the amplification chamber by inserting through a slot and this process is a manually performed. The isothermal amplification of nucleic acid is performed using LAMP method in tubes or cylinders. The detection of amplicons is done using colorimetric techniques either visually or utilizing spectrophotometric imaging. From the detailed description and the claims of the invention, it is clear that there are many manual steps involved in this assay and high-specificity in the detection procedure is not ensured.

US20200013488A1 has reported a system, method and device for the detection of infectious agents from a single clinical sample. The prior art claimed that the method, device or the system can be tested at point-of-service (POS) location for detection of multiple markers for multiple diseases including lower and upper respiratory diseases. Almost all types of viral infections and bacterial diseases are claimed to be detected using this device and system. The prior art further claimed that both nucleic acid markers and protein biomarkers can be detected using this POS device. Moreover, almost all kinds of swab samples and blood samples are claimed to be usable for the detection. This prior art further asserted with its claim that the POS device can be used for detection of plural markers of an indicative infectious disease. Although, the prior patent has mentioned about the point-of-service location as supermarket, clinic, hospital and doctor's office, however, from the patent disclosure, it is not clear about the portability or user-friendliness of the device. Furthermore, it is not mentioned in the claim about the machine whether it is a single integrated system or multiple machine units working together to perform the test along with other auxiliary works. In addition, any generalization or explicit intervention for improving the detection specificity is not attempted in this prior patent.

US20140162244A1 has disclosed a microfluidic cassette for purification of nucleic acid followed by isothermal amplification and real-time fluorescence detection into one chamber. The cassette is made of transparent PMMA sheets joined together to form a reaction chamber. The isothermal heating arrangement comprises a heating block (wire heater, thin-film heater or radiant heater) connected to a temperature controller to maintain the targeted temperature. For detection of the presence of the targeted nucleic acid, florescent based method is applied where a camera, CCD or fluorometer has been used. However, there is no proven evidence of this device to produce test results of comparable specificity and sensitivity of gold standard, with compatible adaptations via innovative detection protocol. Further, the microfluidic cassette demands sophisticated micro-fabrication steps that may compromise affordable mass-manufacturing.

U.S. Pat. No. 7,595,381B2 has disclosed a method and kit for specific detection of SARS coronavirus by designing a unique oligonucleotide primer that can selectively hybridize the specific nucleotide sequence using isothermal amplification process. The kit has been tested using both of the PCR and LAMP and the detection sensitivity has been checked by electrophoresis which confirms that the specific band is clear up to 100 copies. However, the band is not clear for the order of 10 copies of dilution of the sample. Further, the technology is specific to the detection of SARS coronavirus and no further generalization is envisaged.

CN111187863A has disclosed a kit and a method for detection of COVID-19 by double-enzyme method using isothermal amplification. The kit includes the primer pairs for COVID-19 detection, MNAzyme nuclease, reagents for amplification, such as reaction buffer solution, MgAc solution, freeze-dried enzyme. The fluorescent-based detection method uses double-enzyme isothermal amplification of the RNA to be detected and MNAzyme nuclease for fluorescence amplification which indirectly identifies the presence of COVID-19 virus. According to this prior art, the advancement is based on development of a unique reagent kit and a method on isothermal RNA amplification and fluorescence-based detection. However, generalization of the method as well as development of a generic device for such purposes has not been within the scope of this disclosure.

CN111239400A has disclosed an immunochromatographic LFA strip device for detection of COVID-19 using swab, urine or blood samples. The LFA comprises a sample pad, binding pad, reaction pad and water absorption pad. According to this prior art, the advancement has used colloidal gold nanoparticles with a diameter of 55-65 nm for colorimetric detection. For detection of COVID-19 antigen, a novel NP protein monoclonal antibody has been used. From a similar viewpoint, CN111024954A has disclosed a colloidal gold immunochromatographic LFA device for combined detection of COVID-19 antigen and antibody. This prior art is mostly limited to a chromatographic paper-based LFA device along with a separate detection protocol standardized for both antigen and antibody detection. Evidently, the above disclosures are specific to a specialized detection without offering any generalization.

Based on the above traversed prior arts, the following key aspects of consideration are well apparent:

(a) There is no reported prior art on specific DNA-probing integrated generalization of nucleic acid based detection protocol seamlessly fused with an isothermal backbone (for example, RT-LAMP protocol backbone) as a single operational step, type-caste in the generic format of a piece-wise isothermal nucleic acid based testing with streamlined sample-to-result integration in a single low-cost portable device without any intermediate manual intervention between the reaction steps. Advantageously, the selective piece-wise isothermal testing covered under the present advancement includes operability of the advancement under selectively variable operating requirements based on the desired test protocol for pathogenic detection being carried out including following any varied numbers/sets of temperatures maintained over specified/varied ranges of time, as per the chosen test protocol.

(b) Despite the availability of a wide variety of instruments for isothermal nucleic acid testing, several challenges remain unaddressed, in the reported devices for rendering their applicability in resource-poor settings, including: the need of high voltage power sources to harness electric-field mediated effects, separate arrangements for cell lysis, image analysis outside the ambit of device integration, need of large reagent volume per test, requirement of sophisticated microfabrication steps with inherent complexity, and prohibitive cost of the disposable unit, to name a few. Further, none of these provide a generic universal platform technology for integrated sample-to-result procedure that can be suitably customized as per specific test protocols implementable with minimal manual steps outside controlled laboratory environment.

(c) Considering the emergent scenario of the ongoing COVID-19 pandemic and possible emergence of other pandemics in the future, it is thus absolutely essential to establish a generic rapid yet highly accurate detection procedure which can unambiguously detect the infection at its early stage efficiently without requirement of sophisticated infrastructural support.

OBJECT OF THE INVENTION

It is thus the basic object of the present invention to provide a low cost portable POC diagnostic device for detection of pathogenic infection via nucleic acid based testing that ensures supreme quality compatible with gold-standard laboratory tests and at the same time, inherits cost-effectiveness, rapidity and simplicity of rapid tests, including user-friendly sample-to-result integration.

Another object of the present invention is to provide a RT-PCR simplified method in a generic low-cost stand-alone portable device unit that substitute the complex thermal cycle of the PCR test with piece-wise isothermal reactions inclusive of seamlessly-fused specific DNA-mediated probing steps via pre-programmable thermal controllability, to obtain a test result compatible with the quality of acceptable benchmark gold standards.

Another object of the present invention is to provide a low cost portable POC diagnostic device that integrates one or more of the following procedures: (i) sequence of isothermal reaction steps for amplification and/or probing of the molecular targets (DNA/RNA/proteins) (ii) detection of the labelled/probed molecules on a functionalized paper strip, and (iii) dissemination of colorimetric outcome of the test result by qualitative or quantitative analytics.

Yet another object of the present invention is to provide a low-cost portable POC diagnostic device with an improved isothermal amplification method by seamlessly coupling an additional complementary DNA-probe hybridization as a single step followed by specific binding of dual labelled cDNA on a functionalized paper strip for precise and unambiguous detection with high sensitivity and specificity.

Yet another object of the present advancement is directed to a device which overcomes limitations over CRISPR-Cas based detection technology owing to the high specificity of the complementary base pairing and extensive stability of DNA with respect to RNA.

In particular, the high specificity of the complementary base pairing envisaged in the present innovation in a stable genomic analytical procedure formatted in a single-manual-step based device integration in a pre-programmed manner becomes a highly favorable proposition outside controlled laboratory ambience where any detection method is prone to obvious perturbations stemming from the lack of stringent control.

Yet another object of the present invention is to substitute the complex fluorescent-based optical detection and real-time monitoring of DNA amplification in RT-PCR machines or other equivalent reported detection protocols of similar high standards with a simplified single-user step colorimetric detection of nucleic acid mediated test reaction products on paper-based platform followed by smartphone app-based image analytics without compromising the quality of the end results.

Yet another object of the present invention is to provide a device which substitutes manual-based colorimetric interpretation of the test outcome with smartphone app-based analysis and decision making, the interpretation algorithm applied by the smartphone based detection being non-trivial.

Yet another object of the present invention is to provide a generic low-cost portable POC diagnostic device that can be used for a large number of stand-alone tests, with simple replacement of micro-chamber contents and paper strip after each test.

Yet another object of the present invention is to provide a unified low-cost portable POC diagnostic device that may be used to distinguish between the cases of co-infection or cross-infection of different pathogens (for example, influenza-A and COVID-19).

Yet another object of the present advancement is directed to a device for early detection of pathogen associated nucleic acids which could perform the test at any location and any environmental condition without requiring any specialized healthcare infrastructure and centralized and sophisticated detection instrument like RT-PCR.

Yet another object of the present invention is to provide a POC device for early detection of pathogen associated nucleic acids involving cost-effective materials such as polydimethylsiloxane (PDMS), paper and Pyrex or similar materials for constituting the thermally activated reactive micro-chamber, obviating the needs of PCR tube/micro-tube/Eppendorf as a reaction chamber.

Yet another object of the present invention is to provide a low-cost POC diagnostic device that would ensure seamless integration of the of the reaction chamber with the paper-strip for smooth and automatic dispensing of the amplified DNA product onto the sample pad without any intervention of the user.

Yet another object of the present invention is to provide a sample-to-solution portable diagnostic device that ensures the entire detection process of sample handling to result display with minimum manual intervention and by executing all the process steps within close device to avoid potential carryover contamination which often produces ambiguous results with compromised specificity and sensitivity.

Yet further object of the invention is directed to provide for advancement in POC based diagnostic device for the detection of pathogenic infection via nucleic acid based testing which can be down-scalable or up-scalable depending on the number of test samples required to be diagnosed in parallel.

Another object of the present invention is to provide for a modular POC based diagnostic device for the detection of pathogenic infection via nucleic acid based testing wherein the thermal-reaction unit and the detection unit can be used as independent modules, i.e., the reaction unit can be used as standalone module for those tests for which other methods of detection may be coupled and likewise generic nature of the detection unit renders it to offer a stand-alone platform for colorimetric detection in other types of tests, including rapid antigen and rapid antibody tests as well.

Yet further object of the present invention is to provide for POC based diagnostic device for the detection of pathogenic infection via nucleic acid based testing as a portable instrumentation which can be used as portable lab-in-a-box for a wide variety of nucleic acid based tests, with specific protocols varying from one another.

Yet another object of the present invention is directed to development of a POC based diagnostic device for the detection of pathogenic infection via nucleic acid based testing enabling generic nature of the test rendering it suitable as a unique low-cost platform technology that can bring molecular diagnostics out of specialized and sophisticated lab to resource-limited settings without compromising the accuracy of the test to a significant extent. This enables the realization of amalgamated hybrid paradigm of affordable nucleic acid-based point of care test that ensures supreme quality of gold-standard laboratory tests in one hand, and inherits the cost-effectiveness as well as simplicity of commonly available rapid tests on the other hand.

Yet another object of the present invention is achievement of complete sample-to-result integration in a generic low-cost portable device that can be used for a large number of different stand-alone tests, with simple replacement of micro-chamber and paper strip after each test as the only disposables. This favours manufacturing scale-up of the device unit, as well as minimization of disposable unit costs.

Another object of the present advancement is directed to integration of isothermal DNA amplification process with generic DNA based specific probing process in a single user step concomitant format customizable in a single thermal control cum reaction unit enabling high specificity without incurring any operative additions and procedural complexities that could otherwise lead to features hallmarking unwarranted carry over contamination.

Yet another object of the present invention is directed to the developments of novel primers/reagents in accordance with the present advancement suitable for the desired SARS-CoV-2 detection with enhanced specificity and sensitivity.

SUMMARY OF THE INVENTION

Thus, according to the basic aspect in the present invention, there is provided a point of care (POC) device for use in the detection of pathogenic infection via nucleic acid-based testing comprising a thermal control cum reaction unit for providing seamless integration selectively for (a) RNA containing test sample conditioning (b) reverse transcription to cDNA including its amplification, and (c) complementary DNA-probe based hybridization all in said thermal control cum reaction unit for use in desired analyte testing;
said thermal control cum reaction unit including a microcontroller based isothermal heating unit operatively connected to carry out microcontroller controlled isothermal heating of at least one reaction microchamber in said thermal control cum reaction unit for said desired seamlessly integrated selective (a) RNA containing test sample conditioning (b) reverse transcription to cDNA including its amplification, and (c) its complementary DNA-probe hybridization—in said reaction microchamber, all performed concomitantly, under selectively controlled isothermal heating selectively for piece-wise isothermal nucleic acid based testing subjects following pre-set said microcontroller controlled isothermal heating stages including selectively (a) raising temperature to a desired level (b) holding temperature to a desired temperature for a specified time and (c) lowering temperature to a desired level for desired seamlessly integrated selective (a) RNA containing test sample conditioning (b) reverse transcription to cDNA including its amplification, and (c) complementary DNA-probe hybridization adapted to generate desired specific DNA-probe hybridized reaction product in said reaction microchamber in said thermal control cum reaction unit required for detecting pathogenic infection via nucleic acid based testing.

Another aspect of the present invention provides a POC based device comprising said thermal control cum reaction unit adapted for DNA probe RT lamp reaction as a single user step protocol wherein the said microcontroller based isothermal heating unit comprises microcontroller means, optocoupler relay unit, micro heater, heat sink cooling fan and temperature sensors which operatively connect to a heating block and said thermal control cum reaction unit including said reaction microchamber for generating desired DNA-probe hybridized reaction product adapted to interface with any POC detector of pathogenic infection based on said generated DNA-probe hybridized reaction product.

In another aspect, the present invention provides the POC-based device which is interfaced with said POC detector including colorimetric detector as preferable means for colorimetric detection comprising a colorimetric detection unit including an imaging acquisition and analysis means.

Yet another aspect of the present invention provides a POC based device wherein the said microcontroller based isothermal heating unit comprises microcontroller means which includes pre-programmable isothermal reaction operability options including temperature and duration of heating control means adapted for selectively carrying out sample to solution integration for detection of pathogen-associated RNA including single step swab/saliva to result protocol selectively for (i) pre-conditioning of extracted RNA from sample or RNA directly in any body-fluid sample containing RNA (ii) isothermally based simultaneous reverse transcription of RNA followed by c-DNA amplification and (iii) complementary DNA-probe hybridization seamlessly in said reaction microchamber which is operatively connected to optocoupler rely unit, micro heater, heat sink cooling fan and temperature sensors which operatively connect to said heating unit comprising a heating block; and
said POC detector includes means for colorimetric detector including a colorimetric detection unit including a microfluidic paper strip and an imaging acquisition and analysis means including programmed/pre-set camera properties enabling sample to result including extracted sample RNA to seamless dissemination of test results of said detection of pathogenic infection via nucleic acid based testing.

Yet another aspect of the present invention provides POC based diagnostic device wherein the said microcontroller based isothermal heating unit includes selective operability for pre-programmable isothermal reactions including one or more isothermal processes as per the specific test protocol based controlled heating means of the said reaction microchamber through said heating unit selectively to a specific temperature for a desired period of time as per the specific test protocol via pre-set thermal protocol including for said pre-conditioning of the said RNA present in any body fluid including swab/saliva test sample involving sample homogenization, breaking of viral capsid and inactivation of enzymes for rendering suitable for subsequent amplification to cDNA and complementary DNA-probe hybridization seamlessly in said reaction microchamber favouring desired specificity and sensitivity of said POC detection.

A further aspect of the present invention provides a POC based device microchamber and microchamber guide means for introducing piecewise analyte sample and reaction mixture including specific gene based double modified DNA probes into the said thermal control cum reaction unit and cooperative microchamber guide means for carrying the said microchamber with amplified final reaction mix to the said colorimetric unit for the required colorimetric detection in cooperation with the said microfluidic paper strip and an imaging acquisition analysis means, all seamlessly integrated for selectively carrying out contamination free (i) RNA containing test sample conditioning (ii) reverse transcription of RNA with concomitant DNA amplification, (iii) specific DNA probe hybridization and (iv) dispensing of sample on the said microfluidic paper strip and (v) on-line colorimetric detection free of any manual intervention as a stand-alone, low cost portable RNA-test based diagnostic platform A further aspect of the present invention provides a POC based device comprising microchamber cartridge and microchamber guide rail for the desired introduction of piecewise analyte sample and reaction mixture containing microchamber into the said thermal control cum reaction unit and wherein the said microfluidic paper strip comprises selectively functionalized sections for sequentially executing surface plasmon resonating nanomaterial-conjugated complementary analyte binding/hybridization reaction and the said imaging acquisition and analysis means comprises smartphone-based imaging and analytic means.

In a further aspect, the present invention provides a POC-based device comprising a portable housing supporting the said thermal control cum reaction unit and the said colorimetric detection means which are seamlessly integrated involving the movable said reaction microchamber into the said isothermal amplification unit for the desired reaction and thereafter carrying the said microchamber with amplified and hybridized final reaction mix to an adjacent said colorimetric unit for required colorimetric detection.

A still further aspect of the present invention provides a POC-based device comprising providing said detection unit in a portable platform for ready coupling to the said microfluidic reaction chamber for dispensing the amplified and labelled cDNA product and/or test reagents as required involving on line dispenser mechanism onto a sample pad of the colorimetric detection strip via a seamless fluidic pathway including microfluidic dispenser means.

In another aspect the present invention provides a POC-based diagnostic device comprising the said microcontroller modulated thermal control cum reaction unit including the said reactive microchamber in a holding cartridge for executing piecewise-isothermal reaction steps with a provision of engaging plurality of microchambers' hosting reagents including non-radioactive labelled primer and probe sets, and seamlessly interfacing with the said detection means including functionalized custom-made paper strips preferentially adsorbed with surface plasmon resonating nanomaterial conjugated analytes as well as other target analytes to orchestrate the binding events.

In a further aspect, the present invention provides a POC-based device wherein the said colorimetric detection unit including the said microfluidic paper substrate comprising: sequentially (a) a sample introducing chamber integrated with a channel body of nitrocellulose filter paper; (b) binding section immobilized with colloidal nanomaterials conjugated with primary target analytes in channel made of glass fiber material; (c) detection area on a membrane base including a reaction area adapted for immobilization of specific reaction analytes including a control line for secondary binding; and (d) waste absorbing section comprising of blotting paper/absorbing material with high absorption quality; and cooperatively integrated for image analytics and dissemination via a smartphone app.

Yet another aspect of the present invention provides a POC-based diagnostic device comprising said thermal control cum reaction unit, said colorimetric detection unit and the said image analytic and dissemination means cooperatively integrated into a portable housing (lab-on-a-box) including:
said thermal control unit including an isothermal block including a heating platform on which the said microchambers including puncturable base thereof are placed for the biochemical reaction with cooperative heating control circuitry and power supply operatively connected to said isothermal heating block;

said colorimetric detection unit including a cartridge type access for inserting said microfluidic paper substrate/strip; on-line dispenser mechanism for sequentially dispensing the amplified and labelled cDNA product and/or test reagents as required including puncturing needle valve and dropper for test reagent including LFA buffer, said needle valve mechanism operable for puncturing the base of the microchamber for release of reaction product onto said microfluidic paper substrate/strip and said dropper for controlled dropping of reagents/buffer on said reaction product containing paper substrate/strip; and said image analytics and dissemination section including said smartphone app including image capture, processing and algorithmic implementation and results display operatively connected to a transparent viewing window for image acquisition of colorimetric changes of the reaction strip on said microfluidic paper substrate.

A further aspect of the present invention provides a POC-based device comprising microchamber holding cartridge supporting the microchambers adapted to be movable through a guided rail synchronized with the said cartridge-based feeding of microfluidic paper substrate in the said sample-introducing chamber of the said colorimetric detection unit whereby the microchamber is adapted to be placed in between a fluid dispenser and the sample introducing chamber of the said colorimetric detection unit for the release of the solution onto the said microfluidic paper substrate whereby the sample could flow through the paper substrate matrices due to the capillary action by the force of surface tension and reach out to the detection area through the conjugate section.

Still another aspect of the present invention provides a POC-based device comprising said microchambers include closed contamination-free reaction chamber with a dispensing mechanism fitted with the reaction chamber adapted to be actuated manually and/or automatically to dispense the final product seamlessly onto the microfluidic sample pad of a 'protected' LFA strip internally encapsulated within a transparent polymer made cassette via feedable via a movable cartridge.

Another aspect of the present invention provides a POC-based device wherein said microfluidic paper substrate comprising: sequentially (a) a sample introducing chamber integrated with a channel body of nitrocellulose filter paper; (b) binding section immobilized with colloidal nanomaterials conjugated with primary target analytes in channel made of glass fiber material; (c) detection area on a membrane base including a reaction area adapted for immobilization of specific reaction analytes including a control line for secondary binding; and (d) waste absorbing section comprising of blotting paper/absorbing material with high absorption quality, said binding section including a conjugate section of colloidal gold conjugated Anti-FAM antibody binding with the targeted DNA with amplified dual labelled DNA complex selectively migrating downwards to the said reaction area including immobilized streptavidin and anti-FAM secondary antibodies at a test line and control lines of the strip, respectively while flowing from the sample pad, the amplified DNA complex selectively traversing the test line and binding with the streptavidin for producing the color by the concentration of colloidal gold nanoparticles/nanoshells attached to the same, the free gold nanoparticles/nanoshells-antibody conjugates selectively bypassing the test line and reaching the control line to bind with the immobilized anti-FAM secondary antibodies and producing the color of colloidal nanoparticles/nanoshells.

Yet another aspect of the present invention provides a POC-based device comprising smartphone based image capturing and application including pathogen-specific training image data sets adapted for analyzing exclusive properties mapped to the upstream experimental significance and eventually the decision making based on the analysis offers with unique features integrated for subsequently analyzing the same and displaying the final results onto the smartphone screen enabling the colorimetric detection step on said microfluidic paper platform within 10 minutes, after about 5-10 minutes of sample introduction into the paper strip.

According to another aspect of the present invention, there is provided, for a POC based device as above, (a) scalable module based on number of test samples in plurality of microchambers in said thermal control cum reaction unit (b) said thermal control cum reaction unit and said colorimetric detection unit adapted for modular integrated cooperation and/or stand-alone independent modules (c) portable lab-in-box.

A further aspect of the present invention provides the POC-based device having high specificity of detection involving correspondingly standardized and customized primers against individual gene target regions including target regions of SARS-CoV-2 genome and influenza-A genome which is free of any cross-reactivity other than the target genome sequences.

Yet another aspect of the present invention provides the POC-based device having high specificity of detection of gene target regions of SARS CoV 2 genome involving set of six RT-LAMP primers specifically selective for each gene set (SEQ. ID No. 1-6 for ORF1B, SEQ. ID No. 10-15 for N gene, SEQ. ID No. 19-24 for E gene, SEQ. ID No. 28-33 for RNase P) ensuring free of cross reactivity towards SERS-CoV-2, MERS and other human coronavirus genome sequences.

A still further aspect of the present invention provides the POC-based device adapted for complementary DNA probe hybridization for additional enhancement of specificity of detection involving labelled DNA probes (BLP Probe SEQ.ID No. 7 for ORF1B, BLP Probe SEQ.ID No. 16 for N gene, BLP Probe SEQ.ID No. 25 for E gene and BLP Probe SEQ.ID No. 34 for RNase P) which specifically bind with the RT-LAMP products amplified involving RT-LAMP primers with no non-specific signal in the negative control sets.

In another aspect the present invention provides the POC-based device wherein said microcontroller based isothermal heating unit, operatively connected to carry out microcontroller controlled isothermal heating of at least one reaction microchamber including the said master mix comprising the reverse-transcription cum isothermal amplification reagents in the form of combined and the dual modified (5'-FAM and 3' ddNTP) complementary DNA probe selected from Seq. ID No. 8 for ORF1B, Seq.ID No. 17 for N gene and Seq.ID No. 26 for E gene along with the RNA sample of the analyte, being thus adapted to automatically execute the combined reaction protocol in a concomitant manner and provide required integration of all the reactions necessary for the test as a pre-programmable, customizable, single user-step close tube piecewise isothermal steps to avoid any intermediate user intervention and chance of carryover contamination.

Another aspect of the present invention provides a microfluidic paper substrate based colorimetric detector suitable for POC based diagnostic device for the detection of pathogenic infection via nucleic acid based testing comprising selectively functionalized microfluidic paper strip for sequential executing surface plasmon resonating nanomaterial conjugated complementary analyte binding/hybridization reaction enabling ready on site colorimetric detection of analyte following pre-set programmed interpretation protocol A further aspect of the present invention provides a microfluidic paper substrate based colorimetric detector comprising: sequentially (a) a sample introducing chamber integrated with a channel body of nitrocellulose filter paper; (b) binding section immobilized with colloidal nanomaterials conjugated with primary target analytes in channel made of glass fibre material; (c) detection area on a membrane base including a reaction area adapted for immobilization of specific reaction analytes including a control line for secondary binding; and (d) waste absorbing section comprising of blotting paper/absorbing material with high absorption quality.

Still further aspect of the present invention provides a microfluidic paper substrate based colorimetric detector comprising sample introducing chamber obtained of nitrocellulose filter paper; binding section obtained of glass fiber immobilized with colloidal surface plasmonic nanomaterials including preferably gold nano materials conjugated with primary antibodies; detection section including microfluidic paper platform including microcellulosic membrane having corresponding specific antibody; and waste absorption section.

Another aspect of the present invention provides the microfluidic paper substrate based colorimetric detector comprising: microfluidic paper substrate comprising: sample introducing chamber having selectively a circular, polygonal, rectangular section integrated with a channel body of rectangular section made of nitrocellulose filter paper; binding section immobilized with colloidal nanomaterials conjugated with primary target analytes is rectangular shaped channel made of glass fiber material; detection area on a membrane base including a reaction area adapted for immobilization of specific reaction analytes including a control line for secondary binding; and waste absorbing section with rectangular shaped channel comprising of blotting paper/absorbing material with high absorption quality.

A further aspect of the present invention provides a microfluidic paper substrate based colorimetric detector adapted for the specific detection of SARS-CoV-2 viral RNA comprising said binding section of said the colloidal gold conjugate Anti-FAM antibody binds with the targeted DNA and the amplified dual labelled DNA complex further migrates downwards to the said detection section for reaction where streptavidin and anti-FAM secondary antibodies are immobilized at the test line and control lines of the strip, respectively while flowing from the sample pad, the amplified DNA complex reaches the test line and binds with the streptavidin for producing the color by the concentration of colloidal nanoparticles/nanoshells attached to the same, the free nanoparticles/nanoshells-antibody conjugates bypass the test line and reach the control line to bind with the immobilized anti-FAM secondary antibodies and produce the color of colloidal nanoparticles/nanoshells.

Yet another aspect of the present invention provides a method for POC-based detection of pathogenic infection via nucleic acid based testing, comprising:

carrying out selectively anyone or more of (a) RNA containing test sample conditioning (b) reverse transcription to c-DNA including its amplification, and (c) complementary specific DNA-probe hybridization in at least one reaction microchamber in a single thermal control and reaction unit in a seamlessly integrated manner involving microcontroller modulated isothermal of the reaction microchamber within said thermal control cum reaction unit itself under selectively controlled isothermal heating and cooling steps, including (a) raising temperature to a desired level (b) holding temperature to a desired temperature and (c) lowering temperature to a desired level, thereby carrying out both said isothermal amplification reaction for providing c-DNA and DNA probe hybridization in said same reaction microchamber in said thermal control cum reaction unit in a concomitant fashion for contamination free and free of manual intervention based procedure leading to desired reaction product for subsequent analyte detection based thereon.

In another aspect, the present invention provides a method which is carried out in a POC based device of the present invention wherein the said controlled isothermal heating and cooling cycles are selected based on the nature of the RNA analyte, related isothermal amplification reaction mix including primers and involving complementary probes for hybridization for generation of hybridized reaction product in said reaction microchamber followed by imaging of the thus obtained reaction product for colorimetric detection involving image analytics.

In a further aspect, the present invention provides a method comprising carrying out seamlessly the said analyte detection based on said generated hybridized reaction product in an enclosed reaction microchamber in the said thermal control cum reaction unit by further following colorimetric detection in a seamlessly integrated microfluidic paper strip based colorimetric detection unit based on the said reaction products by ready and spontaneous dispensing of said hybridized reaction products on said microfluidic paper strip involving on-line dispenser mechanism for sequentially dispensing the amplified and labelled cDNA product and/or test reagents as required by activating puncturing needle valve mechanism and dropper for test reagent including LFA buffer, said needle valve mechanism initially operated for puncturing the base of the microchamber for release of reaction product onto said microfluidic paper substrate/strip followed by said dropper activation for controlled dropping of reagents/buffer on said reaction product containing paper substrate/strip for desired colorimetric testing; wherein said colorimetric detection is mediated by surface plasmon resonating nanomaterial coated functionalized and functionalized paper strip for selective binding reactions engaging complementary analytes and seamlessly interfacing with a smartphone enabled analytic and dissemination unit.

Another aspect of the present invention wherein said microcontroller controlled isothermal heating operations involving the said microcontroller means is selectively controlled for carrying out isothermal reaction steps for sample to solution integration for the detection of RNA virus infection including on-line fast and accurate swab/saliva to result protocol.

Still another aspect of the present invention provides the method comprising carrying out steps of the said microcontroller controlled isothermal heating means based on piecewise isothermal reaction operability control adapted for selectively carrying out sample to solution integration for detection of RNA including on-line seamless step of swab/saliva to result protocol, selectively following steps of (i) pre-conditioning of extracted RNA from sample or RNA directly in any swab/saliva sample containing RNA (ii) Isothermally based simultaneous reverse transcription followed by c-DNA amplification and (iii) complementary specific DNA-probe hybridization seamlessly in a reaction microchamber followed by (iv) involving colorimetric detection in the said colorimetric detection unit including a microfluidic paper strip and (v) involving an imaging acquisition and analysis means involving programmed/pre-set camera properties enabling sample to result including sample RNA to seamless dissemination of the test results of the said detection of pathogenic infection via nucleic acid based testing.

In another aspect, the present invention provides a method including carrying out controlled heating of said reaction microchamber through said microcontroller based isothermal heating unit selectively to a specific temperature for a required period of time as per the specific test protocol including for pre-conditioning of said RNA present in any direct swab/saliva test sample for sample homogenization, breaking of viral capsid and inactivation of enzymes selectively in the temperature range of 93-98° C. preferably about 95° C. for 2-5 minutes preferably about 3 minutes for SARS-CoV-2 and influenza-A detection for rendering suitable said RNA present in any direct swab/saliva test sample for subsequent reverse transcription to c-DNA, its amplification, and complementary DNA-probe hybridization seamlessly in said reaction microchamber favoring desired specificity and sensitivity of said POC detection.

A further aspect of the present invention provides the method comprising seamless integration of the said isothermal amplification and the said colorimetric detection by cooperative activation of microchamber and microchamber guide means for introducing piecewise analyte sample and reaction mixture containing reaction microchamber into said thermal control cum reaction unit and involving cooperative microchamber guide means for carrying said microchamber with amplified and hybridized final reaction mix to cooperate with said colorimetric unit for required colorimetric detection in cooperation with the said microfluidic paper strip and involving an imaging acquisition analysis means, all seamlessly carried forward for selectively carrying out contamination free (i) RNA containing test-sample conditioning (ii) Reverse transcription of RNA and DNA amplification, (iii) DNA probe hybridization and (iv) spontaneous dispensing of sample on said microfluidic paper strip and (v) on-line colorimetric detection free of any manual intervention as a stand-alone, low cost portable nucleic acid-based testing.

Yet another aspect of the present invention provides the method involving reaction microchamber cartridge and reaction microchamber guide rail for desired introduction of piecewise analyte sample and reaction mixture containing reaction microchamber into the said thermal control cum reaction unit for subsequent detection of analyte based on said selectively functionalized paper-strip and sequentially executing surface plasmon resonating nanomaterial conjugated complementary analyte binding/hybridization reaction and said imaging acquisition and analysis involving smartphone based imaging and analytic means.

A further aspect of the present invention provides the method which is carried out involving selectively (a) non-specific RNA (b) in vitro synthesized specific RNA, (c) RNA extracted from samples (d) direct swab/saliva based RNA virus samples which is preferably used for on-line seamless sample to solution test, in total compliance to established standards of such test methodology.

Still another aspect of the present invention provides the method wherein said step of conditioning of direct body-fluid based pathogen—associated RNA samples in said thermal control cum reaction unit and its seamless integration for reverse transcription of RNA, amplification of c-DNA and DNA-probe hybridization facilities enhancing specificity and selectively of the detection process including even low concentration levels of dilute samples of detection up to as low as 10 copy numbers.

Another aspect of the present invention provides a method wherein said analyte sample used includes the RNA extracted from body-fluid based sample or pre-treated body fluid based sample leading to isolated RNA suspended in buffer solution preferably saliva-PBS buffer which is placed in the said reaction microchamber for the said desired detection of RNA which is free of any required alteration in subsequent downstream operating procedures in either of the two types of input samples mentioned thereof.

Another aspect of the present invention provides the method carrying out reverse transcription of RNA (to c-DNA), isothermal amplification of c-DNA and complementary specific DNA-probe hybridization of RNA sample for detection in a seamlessly integrated concomitant manner in said reaction micro chamber following
i) isothermal amplification of c DNA facilitated by non-radioactively labelled or unlabeled primers to get billions of copies of non-radioactively labelled or unlabeled c-DNA in a seamlessly integrated thermal control cum reaction unit;
ii) hybridization of the products in step i) above with specific complementary DNA probe including FAM labelled oligonucleotides to generate resulting labelled hybridized cDNA reaction product, which is free of any additional manual operative step for executing the specific probing step with all the reagents for step i) and step ii) being altogether dispensed in a single operation step in said thermal control cum reaction unit.

Still another aspect of the present invention provides the method for carrying out SARS-CoV-2 specific viral RNA detection by carrying out RT-LAMP reaction of the analyte sample with biotin labelled FIP primers resulting in biotin labelled cDNA products and said hybridization process of the amplified cDNA products resulting in enhanced specificity and sensitivity in detection is carried out involving FAM labelled oligonucleotides that target the single-stranded loop region of the RT-LAMP products as complementary results in dual labelled c-DNA products that contain both Biotin and FAM attached to it which are then separated very specifically through a functionalized paper strip containing streptavidin and anti-FAM antibody immobilized at the test line and control line, respectively.

A further aspect of the present invention provides the method for carrying out SARS-CoV-2 specific viral RNA detection comprising carrying out DNA probing involving RT-LAMP reaction and DNA probe hybridization as a single step protocol for required high specificity of detection involving correspondingly standardized custom designed primers against individual gene target regions and dual labelled DNA probes which would be free of any cross-reactivity other than the target genome sequences and also avoiding amplification of the specific DNA probes during initial amplification step Yet another aspect of the present invention provides the method carried out for high specificity of detection of gene target regions of SARS CoV-2 genome involving set of six RT-LAMP primers specifically selective for each gene set (SEQ. ID No. 1-6 for ORF1B, SEQ. ID No. 10-15 for N gene, SEQ. ID No. 19-24 for E gene, SEQ. ID No. 28-33 for RNase P) ensuring free of cross reactivity towards SERS-CoV, MERS and other human coronavirus genome sequences.

Still further aspect of the present invention provides the method comprising involving complementary DNA probe hybridization for additional improvement of specificity of detection including labelled probes which specifically bind with the RT-LAMP products amplified involving RT-LAMP primers including highly specific probes which detect SARS-CoV-2 RNA (BLP ProbeSEQ.ID No. 7 for ORF1B, BLP Probe SEQ.ID No. 16 for N gene, BLP Probe SEQ.ID No. 25 for E gene and BLP Probe SEQ.ID No. 34 for RNase P) with no non-specific signal in the negative control sets.

In another aspect the present invention provides the method comprising carrying out said microcontroller controlled isothermal heating of at least one reaction microchamber including as said reagent master mix including RT-LAMP master-mix and dual modified (5'-FAM and 3' ddNTP) complementary DNA probe selected from Seq. ID No. 8 (for ORF1B), Seq.ID No. 17 (for N gene) and Seq. ID NO 26 (for E gene) along with the RNA sample of analyte such as to concomitantly execute the amplification-probe hybridization reaction and achieve required integrated RT-LAMP mediated amplification with the complementary DNA probe-based detection as a single step close tube reaction and avoid any intermediate user intervention and chance of carryover contamination Another aspect of the present invention provides the method including primer modifications, for said the SARS-CoV-2 detection, carried out involving sequences as hereunder:

| Target Region | Primer | Sequence (5' to 3') | Primer Modification |
|---|---|---|---|
| ORF 1b | F3 SEQ. ID No. 1 | GCCATTAGTGCAAAGAATAGAGC | |
| | B3 SEQ. ID No. 2 | GGCATGGCTCTATCACATTTAGG | |
| | FIP (F1c + F2) SEQ. ID No. 3 | TAGCTCCTCTAGTGGCGGCTATTGCACCGT AGCTGGTGTCTC | 5'-[Btn] |
| | BIP (B1c + B2) SEQ. ID No. 4 | TGTAGTAATTGGAACAAGCAAATTCTATGG TGGCCAACCCATAAGGTGAGGG | |
| | Loop F SEQ. ID No. 5 | TTTTTGATGAAACTGTCTATTGGTCATAGT CATACAG | |
| | Loop B SEQ. ID No. 6 | GGCACAACATGTTAAAAACTGTTTATAGTG ATGTAG | |

-continued

| Target Region | Primer | Sequence (5' to 3') | Primer Modification |
|---|---|---|---|
| | BLP Probe SEQ. ID No. 7 | TTGGCACAACATGTTAAAAACTGTTTATAG TGATG | 5'-[6FAM] |
| | BLP 3'-mod Probe SEQ. ID No. 8 | TTGGCACAACATGTTAAAAACTGTTTATAG TGATG | 5'-[6FAM], 3'-[3d_G] |
| | FLP Probe SEQ. ID No. 9 | GCGGCTATTGATTTCAATAATTTTTGATGA AAC | 5'-[6FAM] |
| N gene | F3 SEQ. ID No. 10 | ACAATGTAACACAAGCTTTCG | |
| | B3 SEQ. ID No. 11 | TTGGATCTTTGTCATCCAATT | |
| | FIP (F1c + F2) SEQ. ID No. 12 | GGCCAATGTTTGTAATCAGTTCCTTAGACG TGGTCCAGAACAA | 5'-[Btn] |
| | BIP (B1c + B2) SEQ. ID No. 13 | GCTTCAGCGTTCTTCGGAATCACCTGTGTA GGTCAACC | |
| | Loop F SEQ. ID No. 14 | TGGTCCCCAAAATTTCCTTGG | |
| | Loop B SEQ. ID No. 15 | CGCGCATTGGCATGGAAGT | |
| | BLP Probe SEQ. ID No. 16 | TTGGCATGGAAGTCACACCTTC | 5'-[6FAM] |
| | BLP 3'-mod Probe SEQ. ID No. 17 | TTGGCATGGAAGTCACACCTTC | 5'-[6FAM], 3'-[3d_C] |
| | FLP Probe SEQ. ID No. 18 | GATTAGTTCCTGGTCCCCAAAATTTCC | 5'-[6FAM] |
| E gene | F3 SEQ. ID No. 19 | TTGTAAGCACAAGCTGATG | |
| | B3 SEQ. ID No. 20 | AGAGTAAACGTAAAAAGAAGGTT | |
| | FIP (F1c + F2) SEQ. ID No. 21 | CGAAAGCAAGAAAAAGAAGTACGCTAGTAC GAACTTATGTACTCATTCG | 5'-[Btn] |
| | BIP (B1c + B2) SEQ. ID No. 22 | GGTATTCTTGCTAGTTACACTAGCCAAGAC TCACGTTAACAATATTGC | |
| | Loop F SEQ. ID No. 23 | ATTAACGTACCTGTCTCTTCCGAAA | |
| | Loop B SEQ. ID No. 24 | ATCCTTACTGCGCTTCGATTGTGTG | |
| | BLP Probe SEQ. ID No. 25 | ATCCTTACTGCGCTTCGATTGTGTG | 5'-[6FAM] |
| | BLP 3'-mod Probe SEQ. ID No. 26 | ATCCTTACTGCGCTTCGATTGTGTG | 5'-[6FAM], 3'-[3d_G] |
| | FLP Probe SEQ. ID No. 27 | ATTAACTATTAACGTACCTGTCTCTTCC | 5'-[6FAM] |
| RNaseP | F3 SEQ. ID No. 28 | TTGATGAGCTGGAGCCA | |

-continued

| Target Region | Primer | Sequence (5' to 3') | Primer Modification |
|---|---|---|---|
| | B3 SEQ. ID No. 29 | CACCCTCAATGCAGAGTC | |
| | FIP (F1c + F2) SEQ. ID No. 30 | GTGTGACCCTGAAGACTCGGTTTTAGCCAC TGACTCGGATC | 5'-[Btn] |
| | BIP (B1c + B2) SEQ. ID No. 31 | CCTCCGTGATATGGCTCTTCGTTTTTTTCT TACATGGCTCTGGTC | |
| | Loop F SEQ. ID No. 32 | ATGTGGATGGCTGAGTTGTT | |
| | Loop B SEQ. ID No. 33 | CATGCTGAGTACTGGACCTC | |
| | BLP Probe SEQ. ID No. 34 | CATGCTGAGTACTGGACCTCG | 5'-[6FAM] |
| | FLP Probe SEQ. ID No. 35 | ATGTGGATGGCTGAGTTGTT | 5'-[6FAM] |

In yet another aspect the present invention provides a method which is carried out in a POC-based device of the present invention.

Another aspect of the present invention provides a method including RT-LAMP reaction of the analyte sample with labelled FIP primers resulting in labelled c-DNA products; said hybridization process of the amplified c-DNA products for enhanced specificity and sensitivity being carried out involving FAM labelled oligonucleotides for the step of DNA probe based hybridization; and
on-line coupling to the said portable platform based detection unit for ready dispensing of amplified and labelled c-DNA product onto a sample pad of the said microfluidic paper strip based colorimetric detection strip via a seamless fluidic pathway including microfluidic dispenser means followed by,
seamlessly interfacing with a cooperative smartphone enabled analytic and dissemination unit thereby enabling contamination-free DNA amplification, DNA probe hybridization and smooth dispensing of the products of the thermal-steps on said microfluidic paper strip, and on-line colorimetric detection free of any manual intervention in a stand-alone, low cost portable nucleic acid based testing as POC method for sample to test result generation including extracted sample RNA to seamless dissemination of test results of said detection of pathogenic infection via nucleic acid based testing.

Still further aspect of the present invention provides the method comprising carrying out piecewise isothermal time-steps of reactions free of any manual intervention and dispensing final reaction products onto said microfluidic paper strip functionalized for self-standing colorimetric read outs for capturing involving camera means including smartphone camera with programmed image analytics and customized-designed algorithmic implementations and rapid dissemination of test outcome.

Yet another aspect of the present invention provides the method which is carried out in said portable and cost effective POC device for RNA detection including specific steps for SARS-CoV-2 viral RNA detection comprising:

providing biotin labelled FIP primer sets, 6-FAM probes and other reagents in an airtight said reaction microchamber including samples including either non-specific RNA or SARS-CoV-2 specific RNA;
switching on said thermal control unit for heating the block from room temperature to the targeted temperature of 62-68° C. preferably about 65° C.;
once the desired temperature is reached, the microchambers hosting the reaction mixture are placed onto the isothermal heating block;
continuing said isothermal heating for the next 25 to 35 minutes preferably about 30 minutes whereby the viral RNA gets converted into c-DNA and subsequently gets amplified into millions-billions of copies;
after completion of the amplification process at said temperature of 62-68° C. preferably about 65° C., the device ramps up to reach the temperature of 93-98° C. preferably about 95° C. and termination process of 3-8 minutes preferably about 5 minutes at 95° C. continues, said thermal processes being performed automatically without requiring any manual intervention;
after the termination process is over, the heating system automatically ramps down to a temperature of 48-55° C. preferably about 50° C. which is required for the hybridization process and during the ramp down process of the device, the hybridization process being performed [6-fluorescein amidite (6-FAM) labelled DNA oligonucleotide] for specific binding of the probe to the amplified and biotin labelled target DNA;
after completion of the reaction procedure, the microchambers are pushed forward to the dispensing position using the cartridge and guided rail mechanism and keep the microchambers to cool down to the room temperature;
introducing the samples onto the sample pad of the paper platform which is carried out in a semi-automatic/automatic manner by pushing the microchamber holder through a guided rail synchronized with the paper platform whereby the microchamber is placed in between the dispensing arrangement and the sample introducing chamber and releases the solution onto the sample pad;

allowing the sample flow through the paper matrices due to the capillary action by the force of surface tension and reaches out to the conjugate section wherein the surface plasmon nanomaterial conjugated anti-FAM antibody binds with the targeted dual labelled DNA and the conjugate-DNA complex further migrates downwards to the reaction area where streptavidin and anti-FAM secondary antibodies are immobilized at the test line and control lines of the strip, respectively;

while flowing from the conjugate section, the amplified conjugate-DNA complex reaches the test line and binds with the streptavidin for producing the color by the concentration of the colloidal nanomaterials attached to the same. the free nanomaterial-antibody conjugates bypass the test line and reach the control line to bind with the immobilized anti-FAM secondary antibodies and produce the color of colloidal nanomaterials to enable the detection involving said imaging and dissipation means including a smartphone device.

Yet another aspect of the present invention is directed to a method as above comprising carrying out complete sample-to-result integration for any numbers of different stand-alone tests, with simple replacement of micro-chamber and paper strip after each test as the only disposables.

According to yet another aspect of the present invention there is provided for novel primers developed in accordance with the present advancement suitable for the desired SARS-CoV-2 detection with enhanced specificity and sensitivity including anyone or more of the selective sequences as hereunder:

| Target Region | Primer | Sequence (5' to 3') | Primer Modification |
|---|---|---|---|
| ORF 1b | F3 SEQ. ID No. 1 | GCCATTAGTGCAAAGAATAGAGC | |
| | B3 SEQ. ID No. 2 | GGCATGGCTCTATCACATTTAGG | |
| | FIP (F1c + F2) SEQ. ID No. 3 | TAGCTCCTCTAGTGGCGGCTATTGCACCGTAGCTGGTGTCTC | 5'-[Btn] |
| | BIP (B1c + B2) SEQ. ID No. 4 | TGTAGTAATTGGAACAAGCAAATTCTATGGTGGCCAACCCATAAGGTGAGGG | |
| | Loop F SEQ. ID No. 5 | TTTTTGATGAAACTGTCTATTGGTCATAGTACTACAG | |
| | Loop B SEQ. ID No. 6 | GGCACAACATGTTAAAAACTGTTTATAGTGATGTAG | |
| | BLP Probe SEQ. ID No. 7 | TTGGCACAACATGTTAAAAACTGTTTATAGTGATG | 5'-[6FAM] |
| | BLP 3'-mod Probe SEQ. ID No. 8 | TTGGCACAACATGTTAAAAACTGTTTATAGTGATG | 5'-[6FAM], 3'-[3d_G] |
| | FLP Probe SEQ. ID No. 9 | GCGGCTATTGATTTCAATAATTTTTGATGAAC | 5'-[6FAM] |
| N gene | F3 SEQ. ID No. 10 | ACAATGTAACACAAGCTTTCG | |
| | B3 SEQ. ID No. 11 | TTGGATCTTTGTCATCCAATT | |
| | FIP (F1c + F2) SEQ. ID No. 12 | GGCCAATGTTTGTAATCAGTTCCTTAGACGTGGTCCAGAACAA | 5'-[Btn] |
| | BIP (B1c + B2) SEQ. ID No. 13 | GCTTCAGCGTTCTTCGGAATCACCTGTGTAGGTCAACC | |
| | Loop F SEQ. ID No. 14 | TGGTCCCCAAAATTTCCTTGG | |
| | Loop B SEQ. ID No. 15 | CGCGCATTGGCATGGAAGT | |
| | BLP Probe SEQ. ID No. 16 | TTGGCATGGAAGTCACACCTTC | 5'-[6FAM] |
| | BLP 3'-mod Probe SEQ. ID No. 17 | TTGGCATGGAAGTCACACCTTC | 5'-[6FAM], 3'-[3d_C] |

-continued

| Target Region | Primer | Sequence (5' to 3') | Primer Modification |
|---|---|---|---|
| | FLP Probe SEQ. ID No. 18 | GATTAGTTCCTGGTCCCCAAAATTTCC | 5'-[6FAM] |
| E gene | F3 SEQ. ID No. 19 | TTGTAAGCACAAGCTGATG | |
| | B3 SEQ. ID No. 20 | AGAGTAAACGTAAAAAGAAGGTT | |
| | FIP (F1c + F2) SEQ. ID No. 21 | CGAAAGCAAGAAAAAGAAGTACGCTAGTAC GAACTTATGTACTCATTCG | 5'-[Btn] |
| | BIP (B1c + B2) SEQ. ID No. 22 | GGTATTCTTGCTAGTTACACTAGCCAAGAC TCACGTTAACAATATTGC | |
| | Loop F SEQ. ID No. 23 | ATTAACGTACCTGTCTCTTCCGAAA | |
| | Loop B SEQ. ID No. 24 | ATCCTTACTGCGCTTCGATTGTGTG | |
| | BLP Probe SEQ. ID No. 25 | ATCCTTACTGCGCTTCGATTGTGTG | 5'-[6FAM] |
| | BLP 3'-mod Probe SEQ. ID No. 26 | ATCCTTACTGCGCTTCGATTGTGTG | 5'-[6FAM], 3'-[3d_G] |
| | FLP Probe SEQ. ID No. 27 | ATTAACTATTAACGTACCTGTCTCTTCC | 5'-[6FAM] |
| RNaseP | F3 SEQ. ID No. 28 | TTGATGAGCTGGAGCCA | |
| | B3 SEQ. ID No. 29 | CACCCTCAATGCAGAGTC | |
| | FIP (F1c + F2) SEQ. ID No. 30 | GTGTGACCCTGAAGACTCGGTTTTAGCCAC TGACTCGGATC | 5'-[Btn] |
| | BIP (B1c + B2) SEQ. ID No. 31 | CCTCCGTGATATGGCTCTTCGTTTTTTCT TACATGGCTCTGGTC | |
| | Loop F SEQ. ID No. 32 | ATGTGGATGGCTGAGTTGTT | |
| | Loop B SEQ. ID No. 33 | CATGCTGAGTACTGGACCTC | |
| | BLP Probe SEQ. ID No. 34 | CATGCTGAGTACTGGACCTCG | 5'-[6FAM] |
| | FLP Probe SEQ. ID No. 35 | ATGTGGATGGCTGAGTTGTT | 5'-[6FAM] |

The advancement is described in greater detail in relation to non-limiting exemplary illustrations and the following figures:

BRIEF DESCRIPTION OF THE NON-LIMITING EXEMPLARY ACCOMPANYING FIGURE

Figure 1:
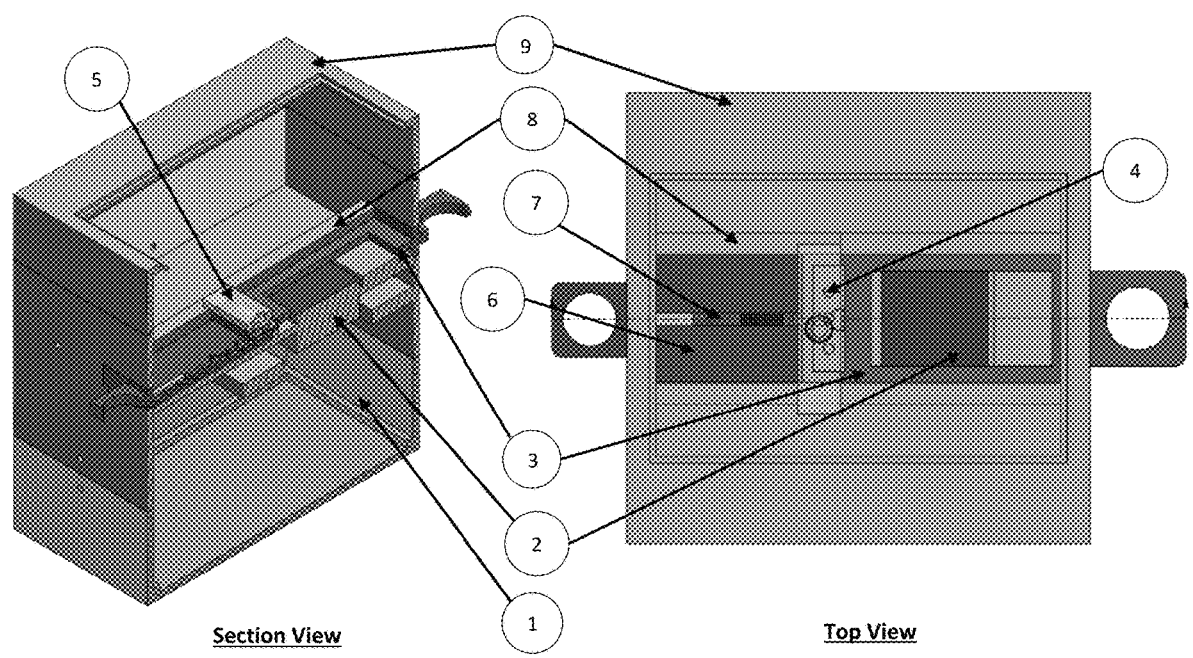
FIG. 1 illustrates schematic drawing of the portable POC device for colorimetric detection of pathogen associated nucleic acids. Each part of the device has been marked and explained in the following figures.
Figure 9:
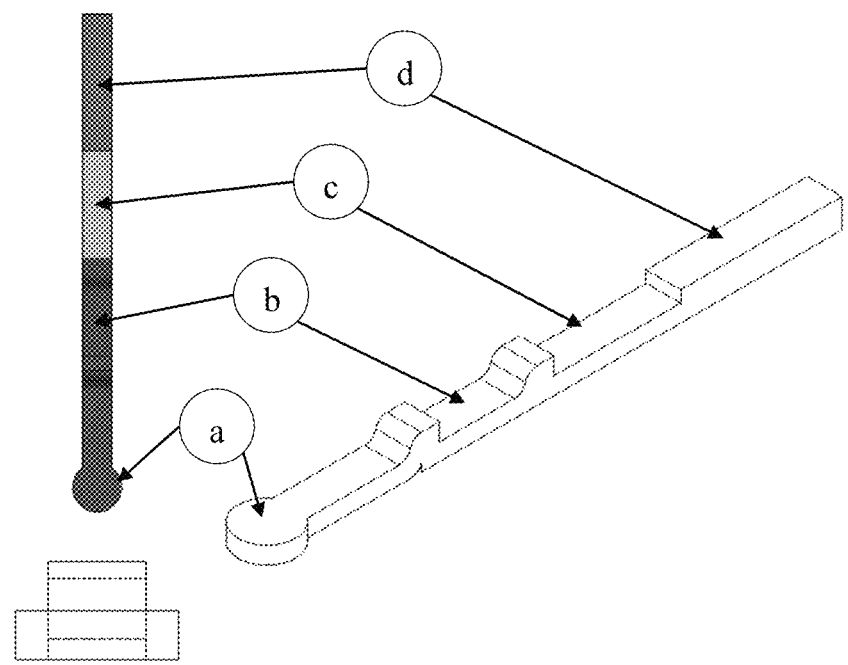

FIG. 9 illustrates an embodiment of the part (7) marked in FIG. 1 i.e. the paper-strip for colorimetric detection of the targeted DNA. As further illustrated in said FIG. 9, Part (a) of the strip (7) is the sample introducing section; part (b) is the conjugation section functionalized with surface plasmon nanomaterials; part (c) is the detection section of the strip made of cellulose membrane functionalized with streptavidin and anti-FAM antibodies; part (d) is the absorbent pad.

Figure 10:
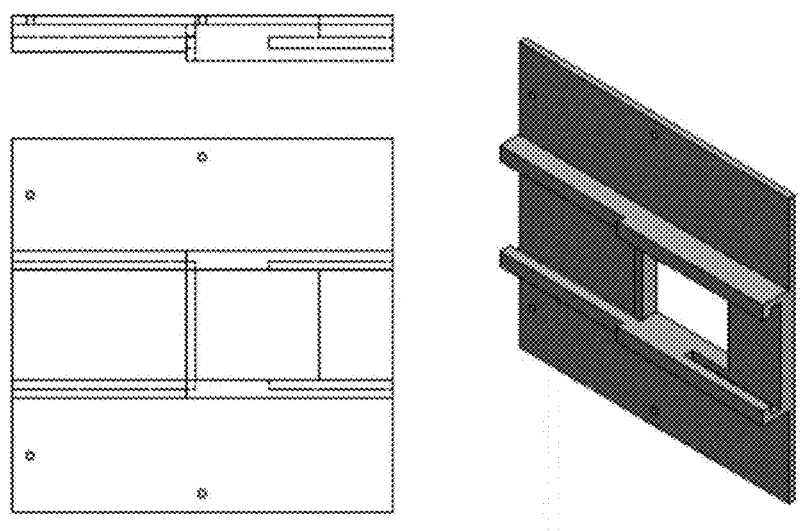

FIG. 10 illustrates an embodiment of the part (8) as marked in FIG. 1 i.e. the guided rail arrangement for insertion of the microchamber and the paper-strip in their desired location into the device for seamless dispensing of the amplified DNA onto the paper-strip without manual intervention.

Figure 11:
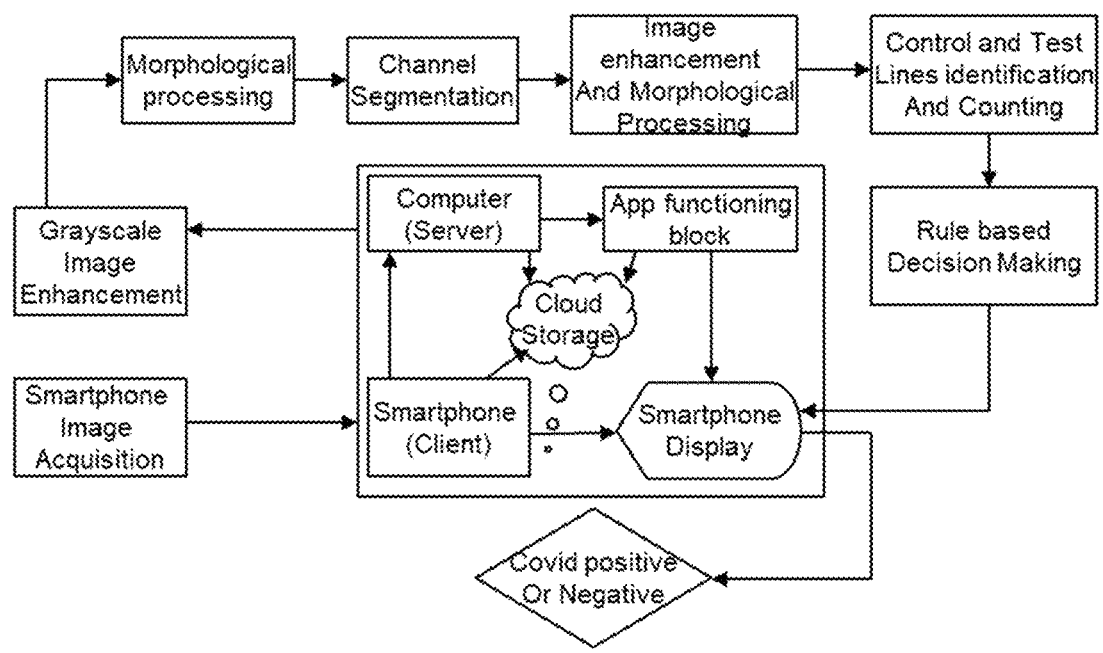

FIG. 11 illustrates the functional block diagram/flow chart of the smartphone-based android app for image acquisition, analysis and result display.

Figure 12:
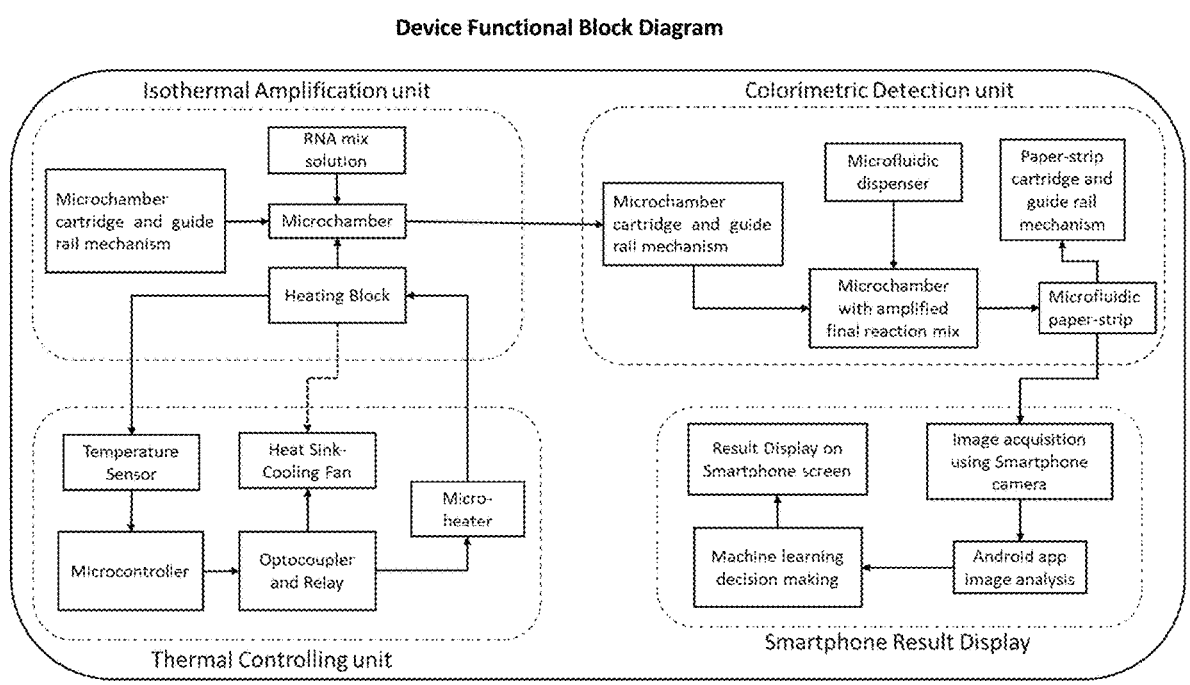

FIG. 12 illustrates the functional block diagram of the generic portable point-of-care device.

Figure 13:
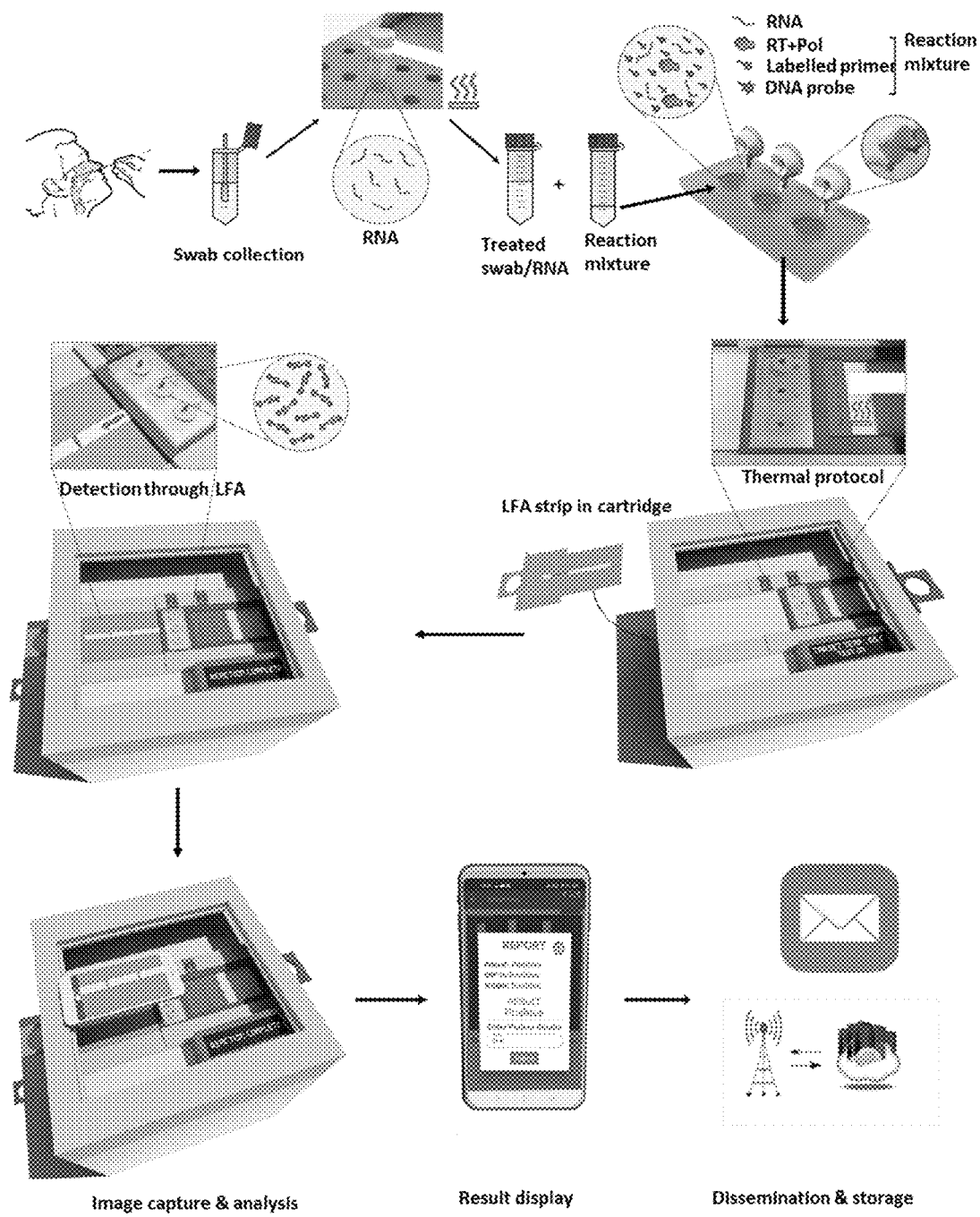

FIG. 13 illustrates the overview of the generic testing methodology in accordance with the present advancement, abbreviated as piecewise isothermal nucleic acid testing (PINAT) for pathogenic infection detection in the integrated device. Followed by collection, the patient body fluid sample may be subjected to RNA extraction or alternatively to a brief initial heat treatment. The purified RNA or the heat-treated sample can be subjected to the subsequent detection protocol. The input RNA is mixed with a reaction master mix containing appropriate enzyme, labelled primers and DNA probes and dispensed to modular reaction-chambers made of soft polymer tubing for subsequent isothermal amplification process. The right inset shows the caps of the reaction-chamber for air-tight sealing. Piecewise isothermal heating of the reaction-mix occurs in the portable device unit as a single user-step process without any intermediate manual intervention. Customization of this thermal protocol for any given test is pre-programmable by using a mathematical step-function: $T=f(t)$. Dispensing of the amplified and labelled cDNA product from reaction chamber to the LFA strip occurs via a manually operated needle valve, with potential automation at the expense of a higher cost. Colorimetric detection of the labelled c-DNA is made on the LFA strip. A smartphone camera is used for image capturing of the reaction pad of the LFA. Smartphone app-based image analysis and result display are rendered onto the mobile screen. Controlled dissemination of the test results to clinical information systems and data analytics may be accommodated via cloud integration.

Figure 14:
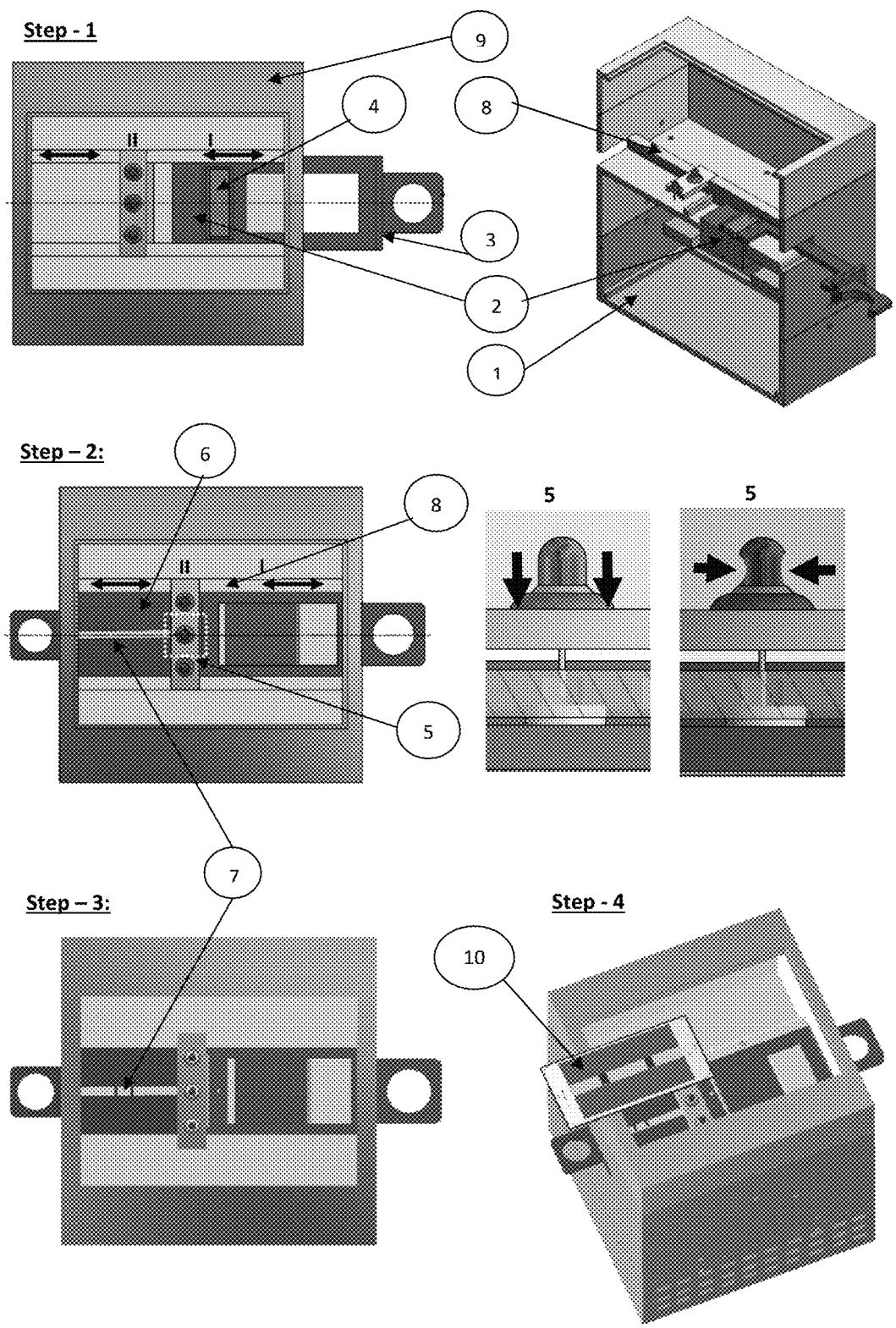

FIG. 14 illustrates the step-wise operative integration of device components during its operation for detection of pathogen associated nucleic acid. Step-1: insertion of the microchamber assembly (4) filled with RNA and master mix onto the heating block (2). For the purpose, at first, the microchambers (transparent) are filled with RNA, master mix with probes, altogether, and sealed airtight, and thereafter, the thus sealed microchamber with its contents is placed onto the microchamber carrying cartridge (3). The microchamber carrying cartridge assembly is then inserted into the device through the desired guided rail (8) assembly (as shown under step-1) up to position I onto the heating block (2) for subjecting to required thermal reactions. Piecewise isothermal processing of the reaction mix is then performed by the device at this position until all the thermal operations are completed. Step-2: Once the required thermal reaction of contents in said microchamber is completed, the microchamber (4) carrying cartridge (3) is inserted further to a second position (position-II) to enable its positioning in between the microfluidic paper substrate based colorimetric detector/paper strip (7) and fluid dispensing mechanism (5). The microfluidic paper substrate based colorimetric detector carrying cartridge (6) is inserted through another guided rail assembly (8) located on the opposite side of the microchamber carrying cartridge (3). The fluid dispensing mechanism (5(a) and 5(b)) includes a puncturing needle valve attached with a dropper holding LFA buffer. At first, the base of the dropper is pressed (shown by arrow in 5(a)) to penetrate the needle through the bottom wall of the micro chamber and puncture it. The product of thermal reactions contained in said microchamber is thus dispensed semi-automatically onto the microfluidic paper substrate based colorimetric detector/paper strip (7). Subsequently, the LFA buffer is also dispensed onto the microfluidic paper substrate based colorimetric detector/paper strip from the dropper (by pressing the side of the dropper as shown in 5(b) using arrow) attached with the dispensing mechanism. This dispensing mechanism can be made automatic using programmable instrumentation or using microfluidic valving system. Step-3: Color generation at the test line and control line. The complex of thermal reaction products and antibody-conjugate traverses through the microfluidic paper substrate based colorimetric detector/paper strip (7) and attached at the test and control line. This color generation takes place within 5-10 minutes of dispensing the products of the thermal reactions onto the LFA paper strip (part-7). Step-4: Smartphone (10) is placed onto the top window (9) of the device at the desired position and captures image of the paper strip with color generated at the test and control lines for ready analytics and dissemination of the test outcome.

Figure 15:
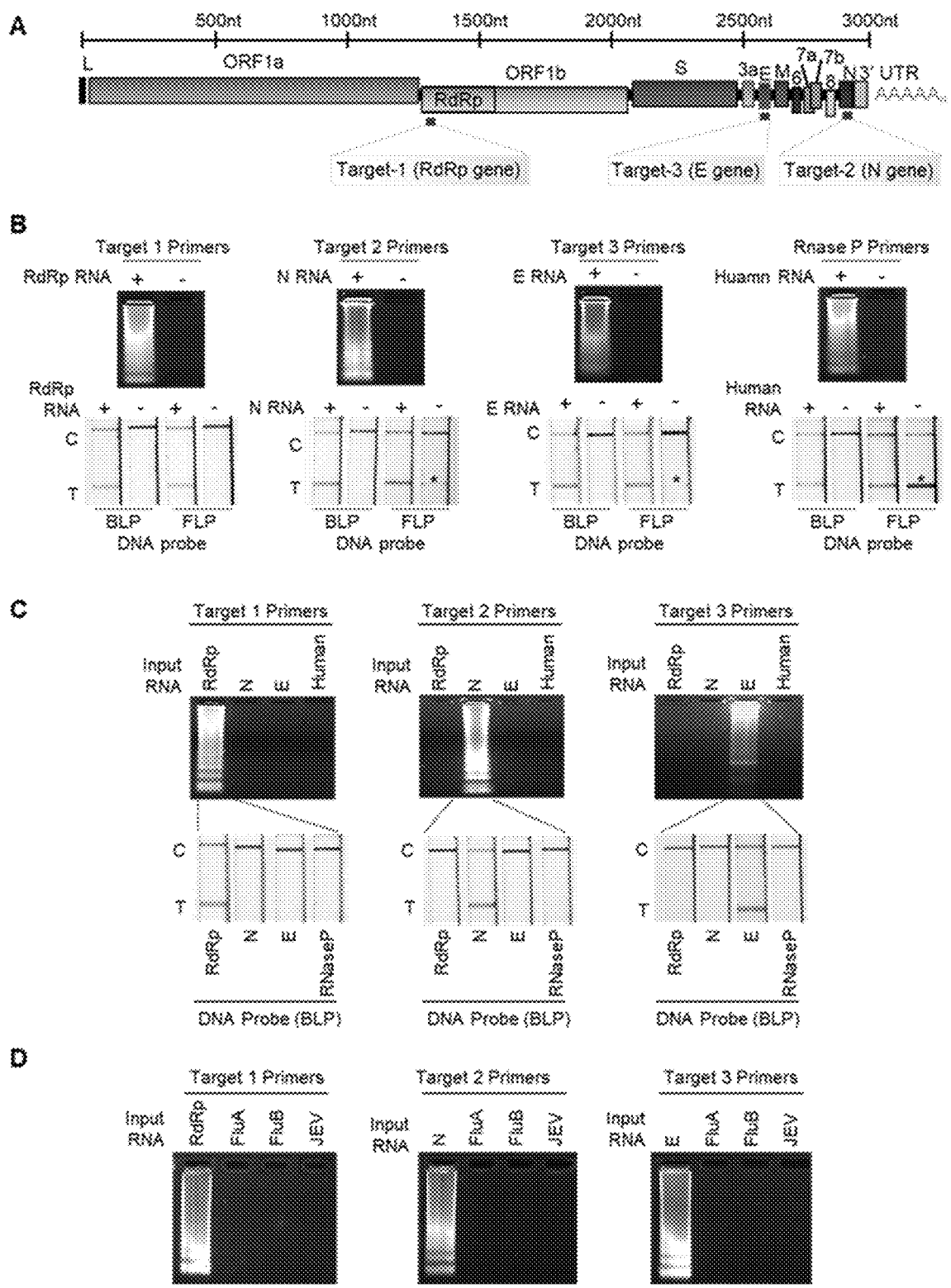
Figure 16:
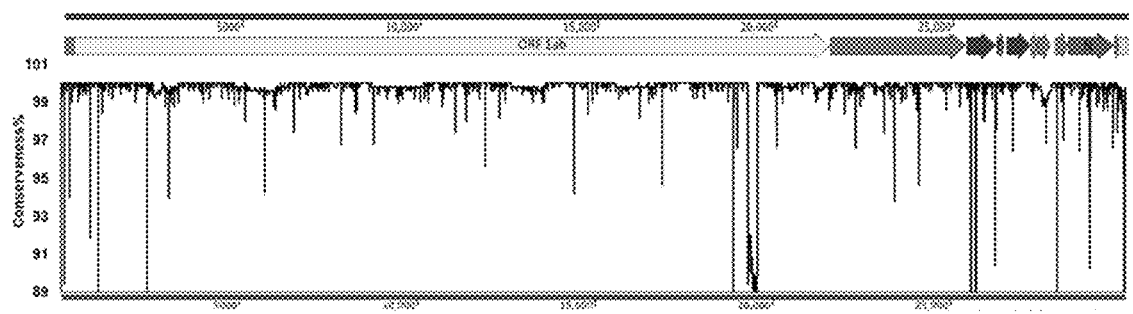
Figure 16:
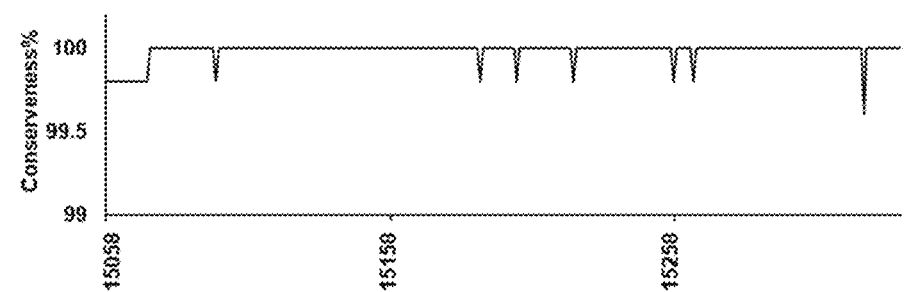
Figure 16:
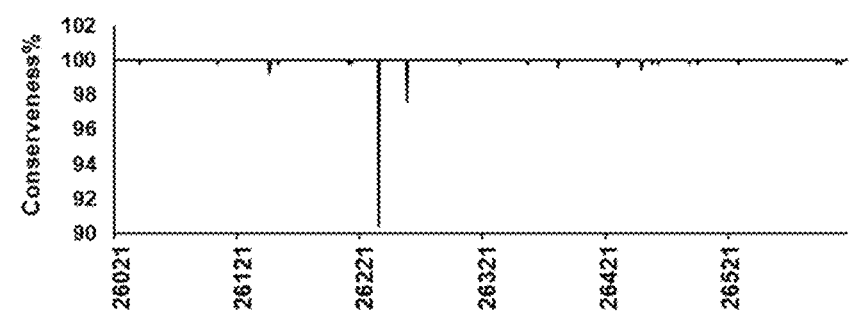
Figure 16:
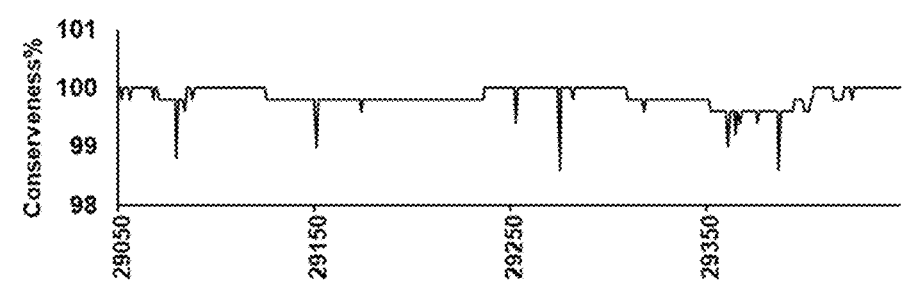

FIG. 15 illustrates the optimization of the test for detecting different target genes in SARS-CoV-2 genomic RNA. (A) Schematic representation of SARS-CoV-2 genome architecture. Different open reading frames were represented with differentially colored boxes. Specific target regions are annotated with dark gray bars and designated as target 1 for RdRp/ORF1b, target 2 for N and target 3 for E genes respectively (B). The integrated reaction cum detection procedure for the testing of individual target regions of viral genomic RNA and RnaseP as internal control. Individual target RNAs were amplified through RT-LAMP reaction and analyzed through 2% agarose gel (top panel) for cross-verification. The amplified reactions were subjected to probing with 6-FMA labelled DNA probes (FLP and BLS) and analyzed through paper strip. Non-specific probing results in appearance of test line in negative control reactions are denoted with asterisks. (C) Cross reactivity of one DNA probe (BLP) towards other SARS-CoV-2 genes or human RNaseP gene. (D) Cross reactivity of individual set of primers and probes against the non-target RNA sequences. RT-LAMP primers designed for one target gene of SARS-CoV-2 showed no cross reactivity against other gene targets, FIG. 16 illustrates the analysis of the conserved nature of the SARS CoV-2 genome. (A) Total 500 complete sequences were aligned with the reference sequence. Positions with gap in reference sequence were not considered. For each position, conservation was calculated by analyzing the positional numerical summery in Bioedit software. Conserved nature of each target regions are expanded in (B) RdRp/ORF1b, (C) N and (D) E.

Figure 17:
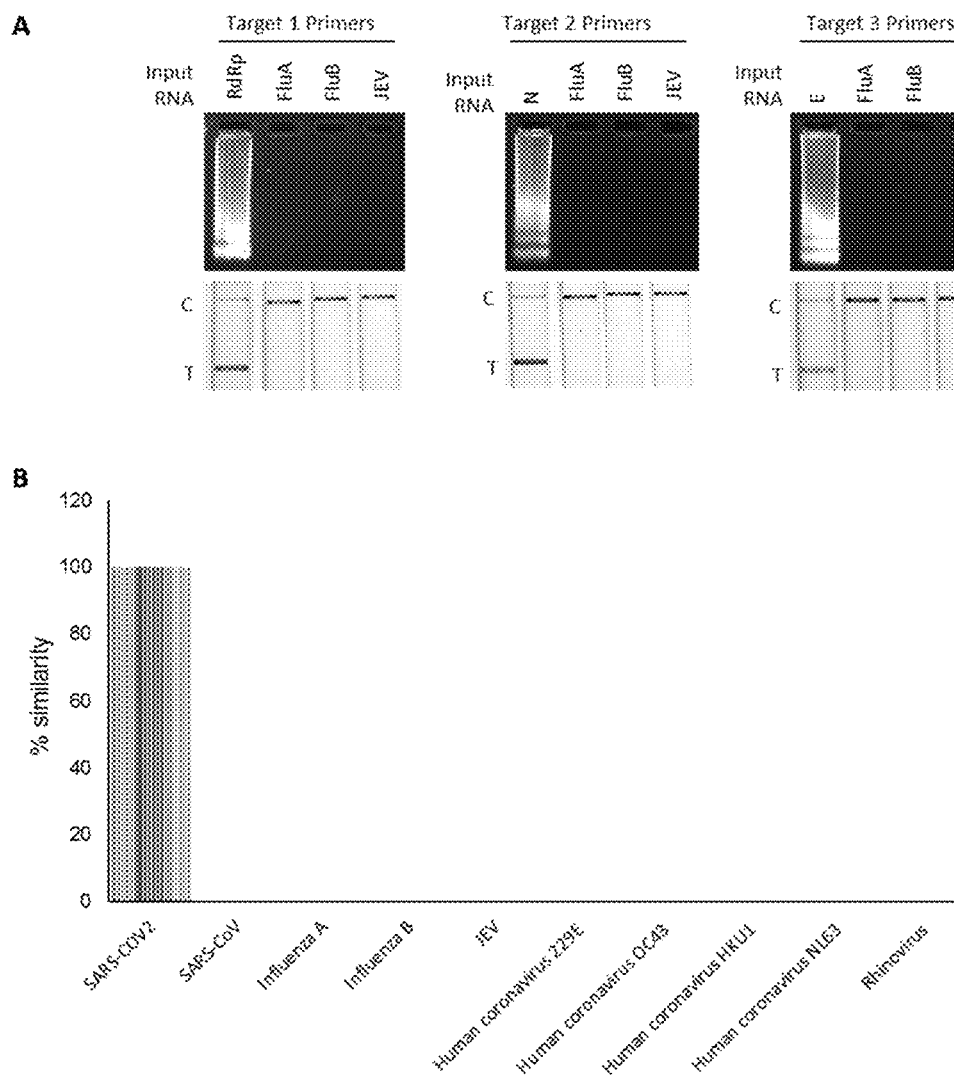

FIG. 17 illustrates cross reactivity of SARS-CoV-2 primers against the genomic RNA of other viruses. (A) Cross reactivity of COVID-19 specific primers were tested using the present protocol against influenza A, influenza B and Japanese Encephalitis viral genomic RNAs isolated from virus particles. Reaction products were analyzed fragments in sextuplets, with LFA based detection. Respective SARS-CoV-2 target genes were used as positive control. (B) Cross reactivity of SARS-CoV-2 specific primers were tested against different RNA viruses in silico.

Figure 18:
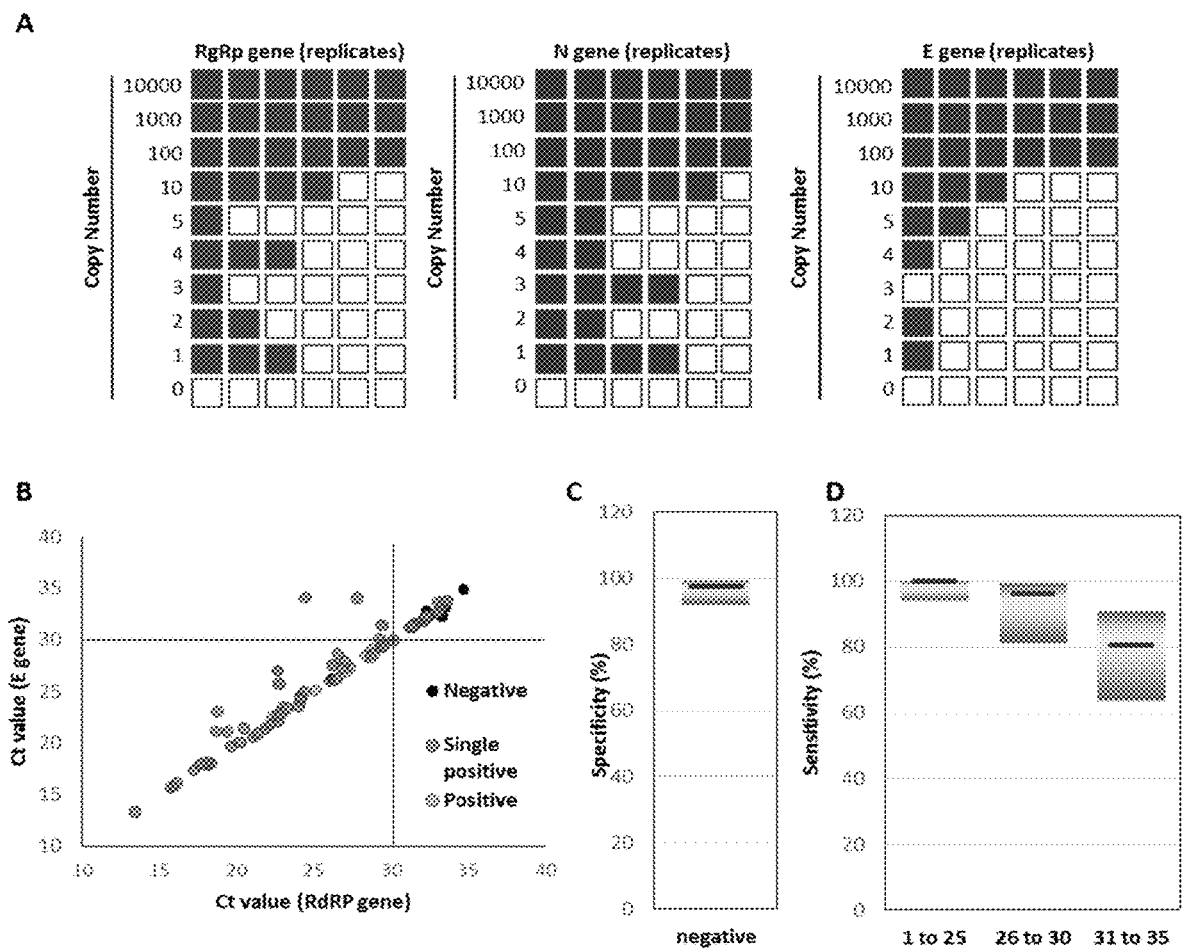

FIG. 18 illustrates that present method shows high sensitivity and specificity for detecting SARS-CoV-2 infection in patient samples (validation tests conducted at ICMR-NICED, Kolkata, India as per strict regulatory guidelines). (A) Limit of detection of the method for individual gene targets. 10-fold serial dilutions of in vitro synthesized gene fragments were subjected to detection in sextuplets. Colored boxes represent positive detection while empty boxes represent negative results for individual replicates. (B & C) Patient sample validation results. (B) distribution of the individual samples across the range of Ct values from 25-35. Samples showing positive or negative for both of the gene targets are represented with red and black circles respectively while positive for one and negative for the other gene target are represented with yellow circles. (C) Box plots showing sensitivity of the detection method for patient samples grouped based upon the Ct values. (D) Specificity of the method.

Figure 19:
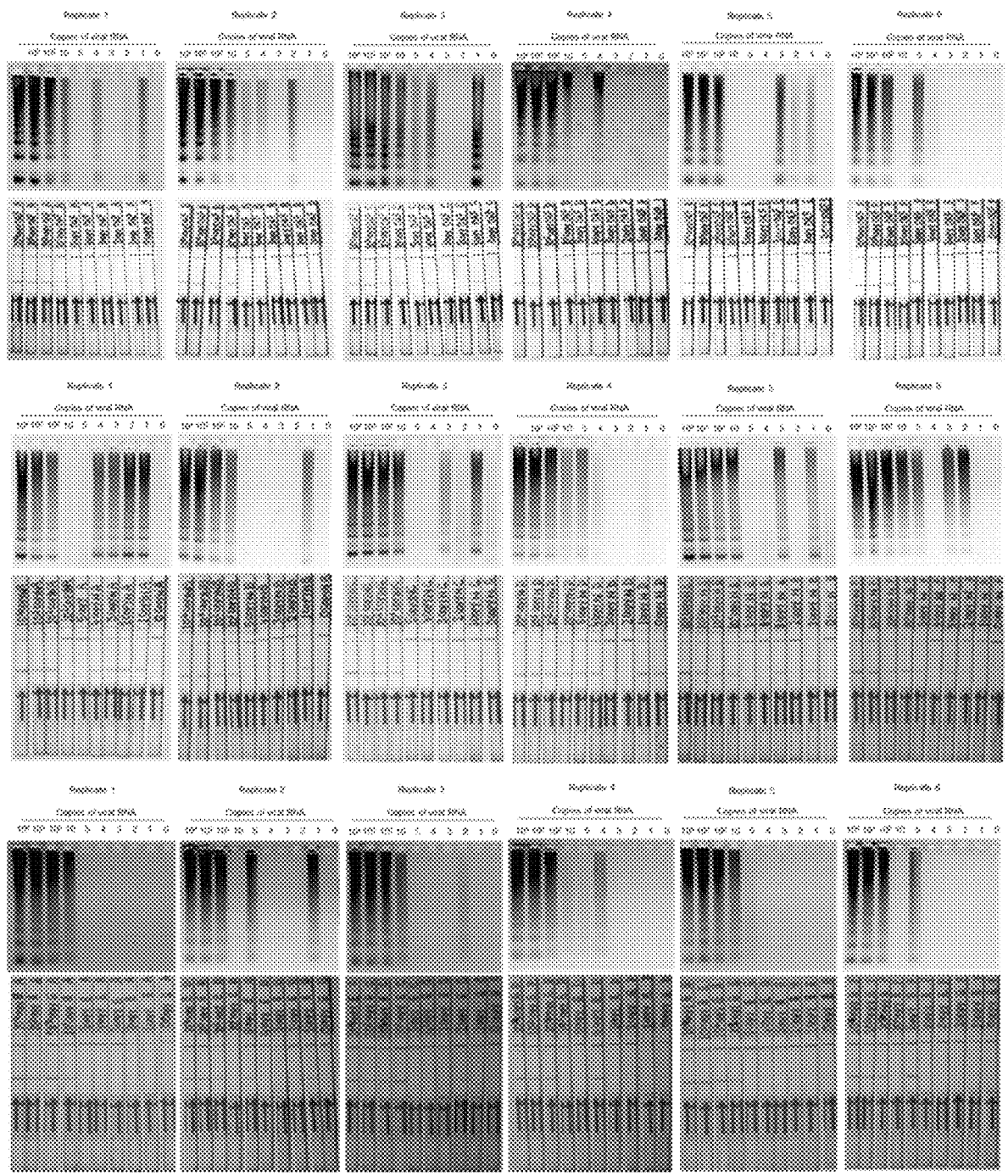

FIG. 19 represents sensitivity of the test using SARS-CoV-2 specific primers and probe. The test protocols were performed with ten-fold serial dilutions of the gene fragment in sextuplets. RT-LAMP reaction products were analyzed by agarose gel electrophoresis followed by DNA probe hybridization and LFA based detection (upper panel-RdRp/ORF1b specific primers, middle panel-N gene specific primers and lower panel-E gene specific primers).

Figure 20:
Figure 20:
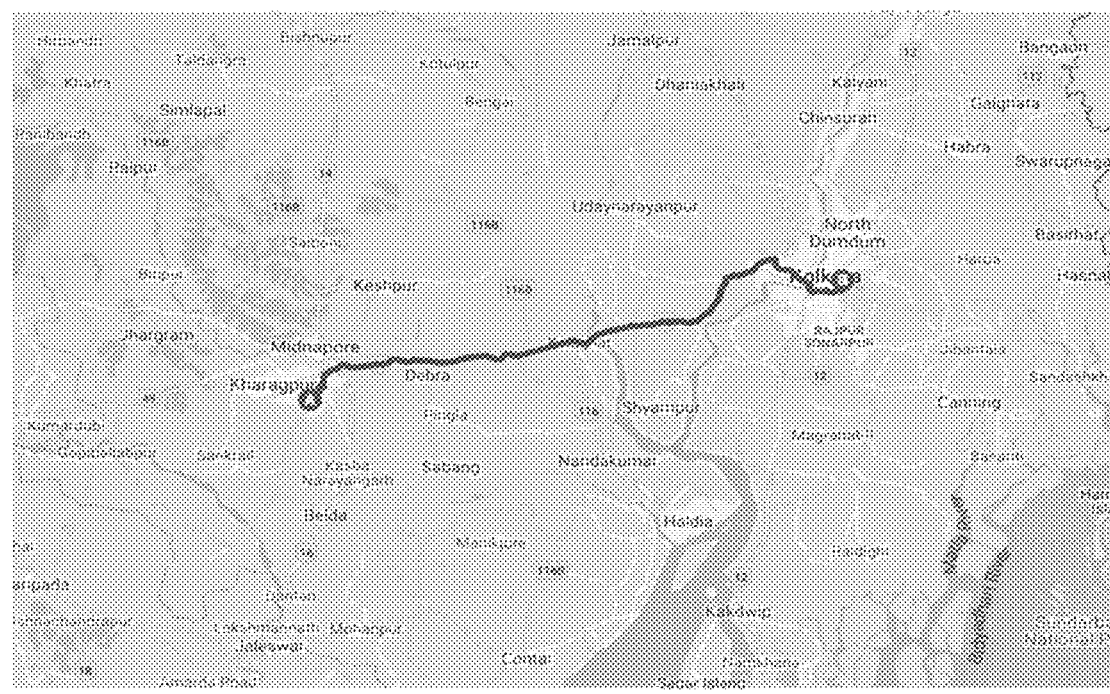

FIG. 20 illustrates kit packaging (upper) and transportation pathway to the test center (lower). The reaction master mixes corresponding to N and RdRp/ORF1b gene targets were reconstituted, tested for quality control and aliquoted in reaction tubes. The reaction master mixes were then transported in ice packs from Indian Institute of Technology Kharagpur to ICMR-NICED where the test with patient samples were conducted using the test method. In peak traffic hours, the nearly 150 km of road travel used to take around 4.5 hours.

Figure 21:
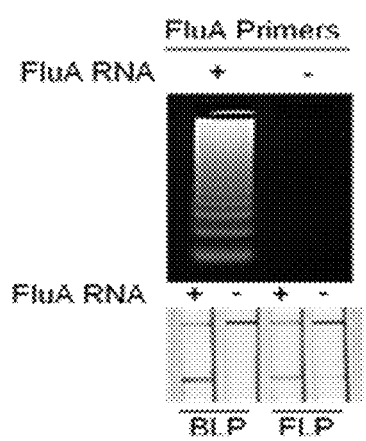

FIG. 21 illustrates method applied for the detection of influenza virus RNA extracted from viruses amplified in MDCK cells. RT-LMAP products were analyzed through agarose gel electrophoresis followed by hybridization with backward or forward loop probed (BLP, FLP) and detected on lateral flow assay strip.

Figure 22:
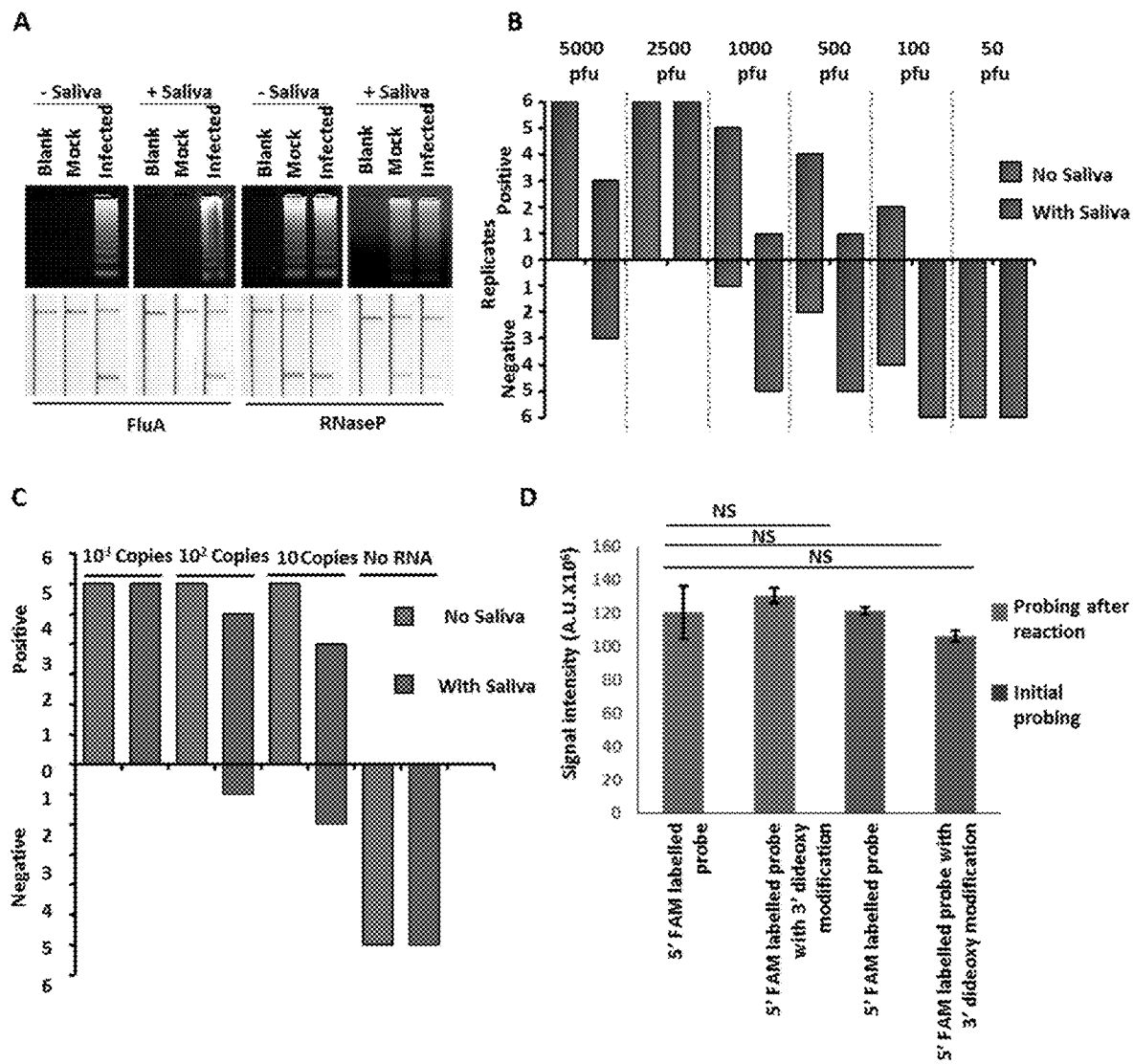

FIG. 22 illustrates a single step solution for detection of RNA virus infection. (A) Detection of influenza A virus genomic RNA directly from infected cells in the presence of human saliva. Human A549 cells infected with influenza A virus, or mock infected, were resuspended in PBS or PBS spiked with human saliva. The suspension was subjected to the detection procedure without prior RNA extraction procedure, but heating at a temperature of 93-98° C. preferably about 95° C. for 2-5 minutes preferably about 3 minutes. (B) Defined numbers of influenza virion particles (PFU), amplified from MDCK cells, were subjected to detection procedure (as mentioned in A) in sextuplets either in presence or absence of human saliva. (C) 10-fold serial dilutions of in vitro synthesized N gene fragment were subjected to detection process in sextuplets either in presence or absence of human saliva. (D) Simultaneous amplification and probing for detection of viral RNA in a single step. RdRp/ORF1b Gene fragment was subjected either to RT-LAMP followed by probing in a sequential manner or simultaneous RT-LAMP and probing reaction in a single step process. In both the cases, BLPs labelled with 5'-FAM and with and without 3'-ddNTP modification were used. Products, at the end of the reaction, were subjected to agarose gel electrophoresis in absence of EtBr and imaged under Cy5 channel.

Figure 23:
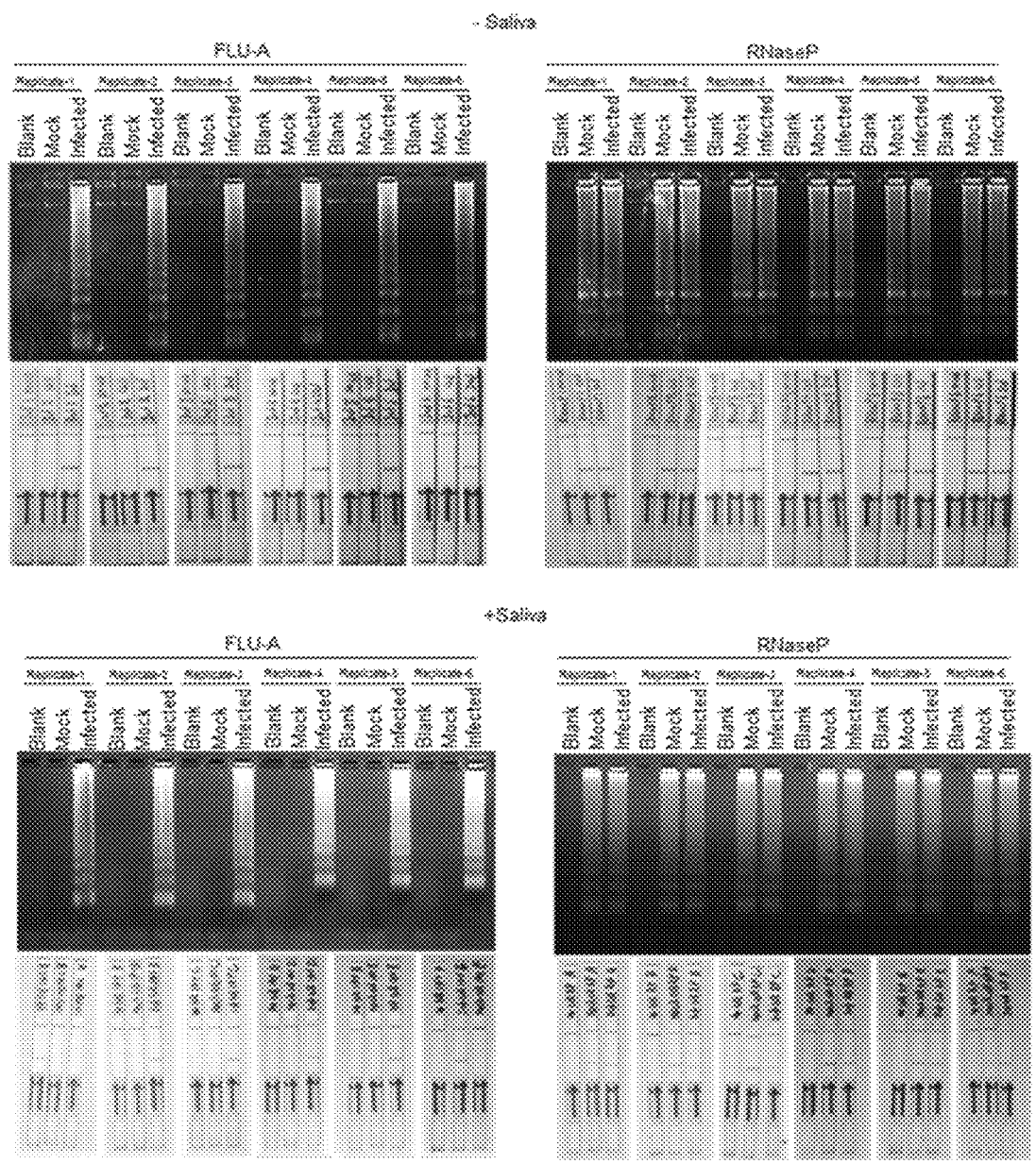

FIG. 23 illustrates (A) RT-LAMP reactions were performed with in vitro transcribed SARS-CoV-2 N gene target region and corresponding primers. Products were subjected to hybridization with BLPs labelled with 5' FAM and with or without 3' ddNTP modification. (B) For single step amplification-cum-probing reactions, both kinds of modified BLPs were added at the beginning of RT-LAMP reaction followed by amplification, head denaturation and hybridization steps carried out without any interruptions. Products were analyzed through agarose gel electrophoresis in absence of EtBr and imaged under Cy5 channel.

Figure 24:
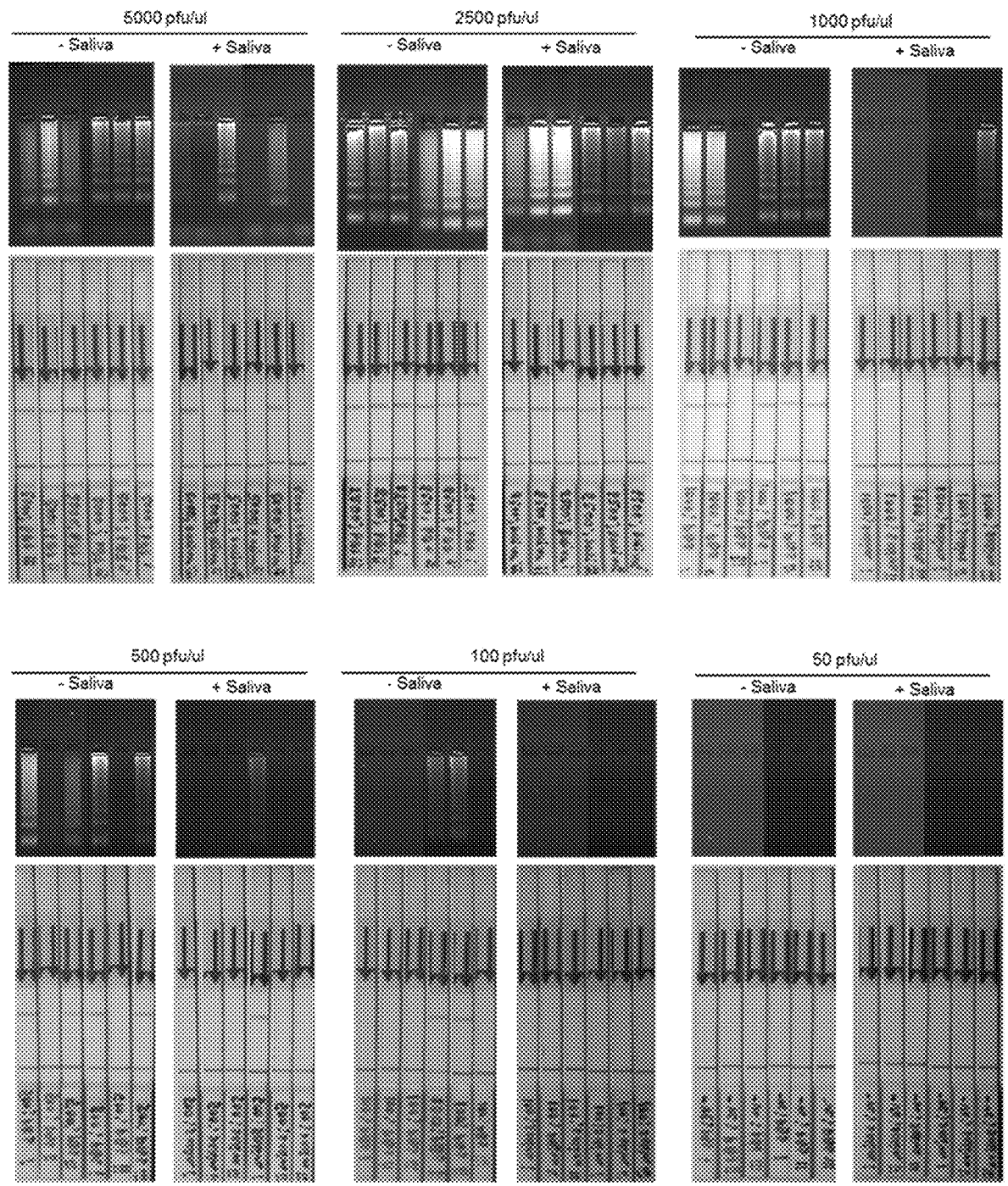

FIG. 24 illustrates limit of detection of the test for detecting influenza A virus RNA directly from virus particles in presence and absence of human saliva. Known PFU of influenza virus particles were diluted in PBS or PBS spiked with human saliva. Subsequently, the sample was directly used for the test (including prior heating at a temperature of 93-98° C. preferably about 95° C. for 2-5 minutes preferably about 3 minutes) without RNA purification.

Figure 25:
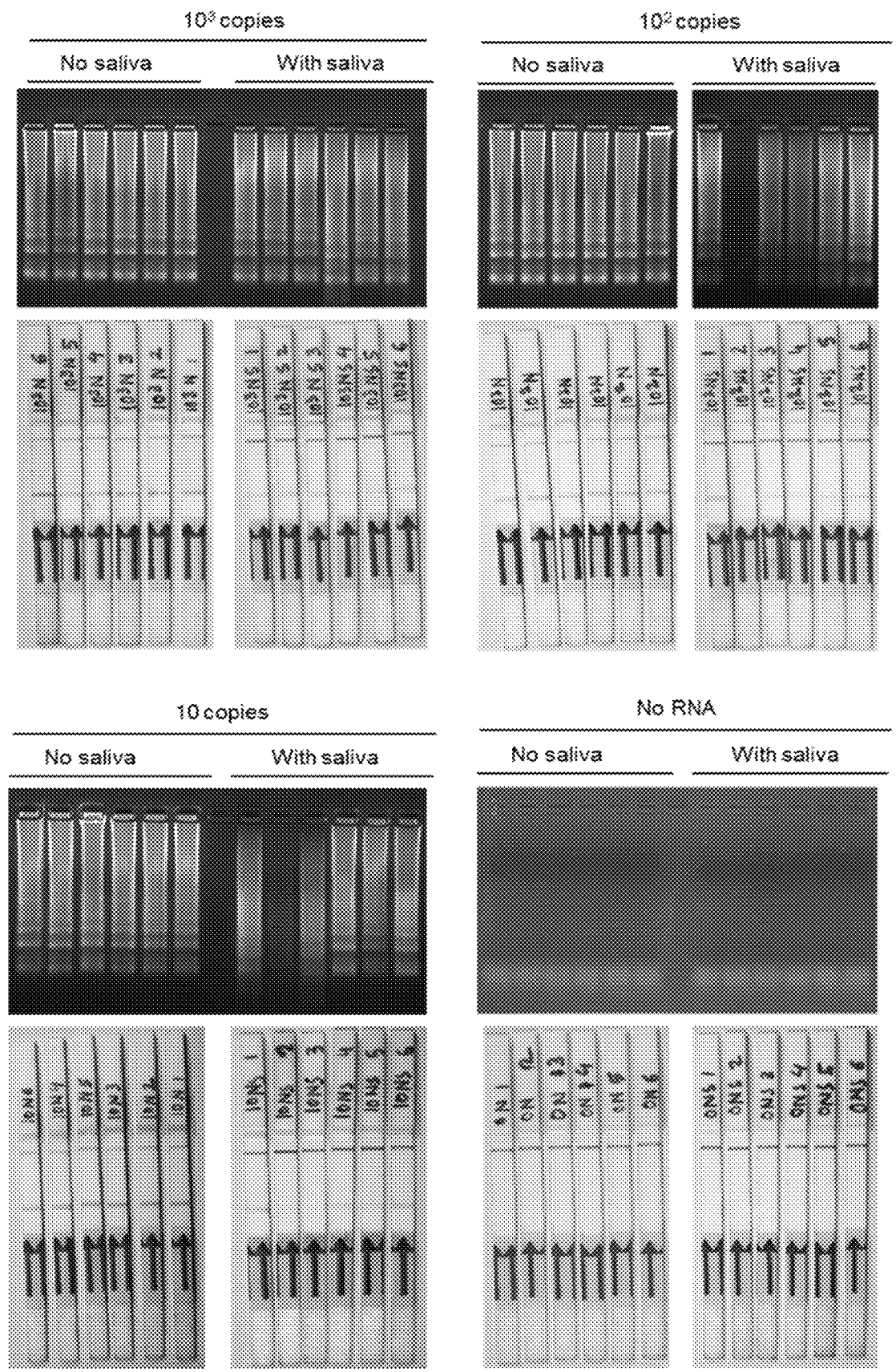

FIG. 25 illustrates Sensitivity of the test for detecting SARS-CoV-2 N-gene specific RNA from human saliva sample. 10-fold serial dilutions of the in-vitro transcribed SARS-CoV-2 N-gene RNA were prepared in PBS or PBS spiked with human saliva which were then subjected to the protocol.

Figure 26:
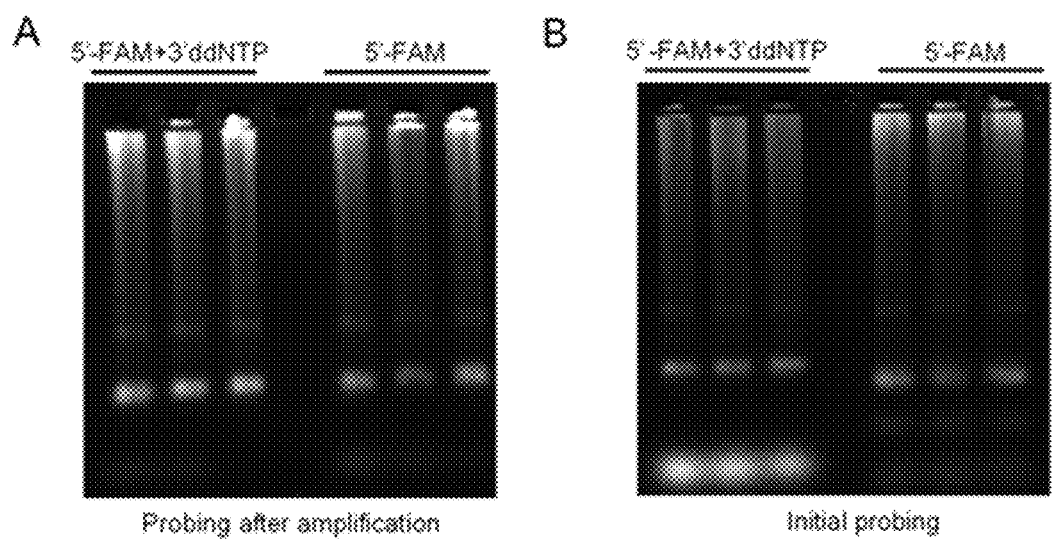

FIG. 26 (A) illustrates RT-LAMP reactions were performed with in vitro transcribed SARS-CoV-2 N-gene target region and the corresponding primers. Products were subjected to hybridization with BLPs labelled with 5' FAM and with or without 3' ddNTP modification. (B) For the integrated amplification-cum-probing step-based protocol, both kinds of modified BLPs were added at the beginning of RT-LAMP reaction followed by amplification, heat denaturation and hybridization steps carried out without any interruptions. Products were analyzed through agarose gel electrophoresis in absence of EtBr and imaged under fluorescein channel.

Figure 27:
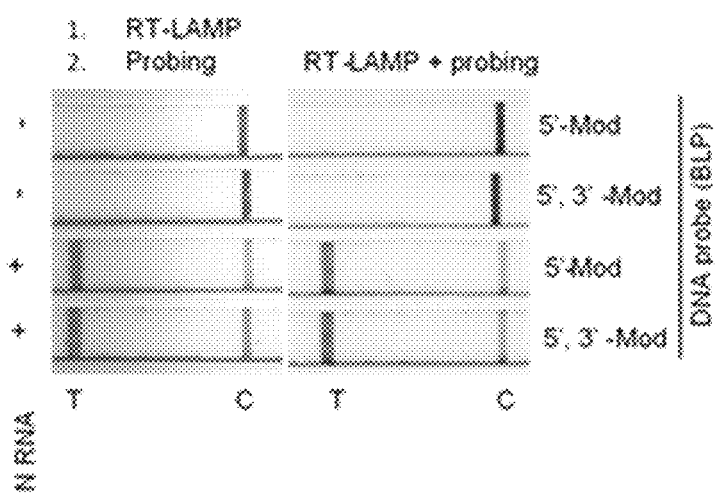

FIG. 27 illustrates RT-LAMP reactions were performed with in vitro transcribed SARS-CoV-2 N-gene target region and the corresponding primers. Products were subjected to hybridization with BLPs labelled with 5' FAM and with or without 3' ddNTP modification (left panel). For the integrated amplification-cum-probing step-based protocol, both kinds of modified BLPs were added at the beginning of RT-LAMP reaction followed by amplification, heat denaturation and hybridization steps carried out without any interruptions. Products were analyzed through LFA.

DESCRIPTION OF THE INVENTION

The present invention as stated herein before thus provides a diagnostic POC device for the detection of pathogen associated nucleic acid, producing test results compatible with acceptable gold standards. The said device and method thereof perform the nucleic acid based detection commensurate with the accuracies of the resource-intensive gold standard RT-PCR method and at the same time is cost effective, robust, user friendly. Such portable device can be installed and functionalized at locations with minimal laboratory resources or can be potentially extrapolated as a POC test in a decentralized manner. Additionally, the generic nature of the portable device unit makes it compatible of performing any similar test methods that combines isothermal reaction and/or lateral flow assay-based detection of the labelled/probed molecules.

The said simple POC device performs three major functionalities sequentially to execute the entire diagnosis process seamlessly with minimal manual intervention. The first major functionality of the device is a reverse transcription concomitantly coupled with the amplification of a tiny amount of RNA to billions of copies of cDNA for ease of detection and identification of the presence of pathogen in the sample. The said amplification process in RT-PCR machine is very complex requires and 40-50 cycles with three-step heating for fast change of temperature at 94-96° C. for denaturation (15-30 sec), at 50-60° C. for annealing (15-30 sec) and 68-72° C. for elongation (>2.5 minutes) per cycle. On the other hand, the amplification process in the device relies upon piecewise isothermal heating steps (typical temperature values range from 62° C. to 98° C.) over pre-defined temporal regimes spanning over minutes. The heating system comprises a heating block, a programmable temperature control unit and a microchamber. This, essentially, is an ultra-low-cost replacement of the expensive Peltier based thermocycling unit of the RT-PCR machine towards achieving equivalent functionalities in terms of DNA amplification.

The second functionality is the detection of the c-DNA after amplification. In the RT-PCR machine, the detection process is very complex optical-based real-time monitoring of the reaction progress for estimation of the amount of DNA by interpreting the increment of the fluorescence signal in each cycle during c-DNA amplification. The detection system includes photodiode, CCD camera with cooling system, LED light for fluorescent excitation, excitation filter, emission filter and fluorescent detector etc. On the other hand, the portable device has colorimetric detection unit for detection of the amplified and labelled c-DNA in a sample using microfluidic paper strip selectively functionalized with surface plasmon resonating nano-materials and antibodies. This is one-step colorimetric analysis and detection for specific pathogen from the final amplified product. The simplicity in the detection protocol is highly advantageous for implementation of the POC device.

The third functionality is data analysis and result display. RT-PCR machine has in-built software associated with the instrumentation for real-time data acquisition and data analysis to estimate the initial load of the pathogen and amount of amplified c-DNA in each cycle. A skilled technician is required to interpret the result for confirming the presence of pathogen and estimate the severity of the infection. On the other hand, the present portable device is integrated with a smartphone means for performing image analysis and dissemination of test results. The colorimetric reaction is captured by the smartphone camera for image analysis and interprets the data using rule-based analysis by the custom-made android app and display the decision of the presence or absence of the targeted pathogen.

In a further aspect, the present invention provides device achieving DNA amplification involving a single DNA polymerase Bst3 along with multiple sets of primers.

In a further aspect, the present invention provides a method and device to achieve a single user-step amalgamation of reverse transcription, DNA amplification and specific DNA probing in a thermal unit that is operatively connected to carry out customized piecewise isothermal close-tube reactions, particularly adapted to arrest any undesired amplification of the specific DNA probe added, thereby obviating the need of any intermediate user intervention, and yet enabling the amplification and specific probing reaction to take place harmonically in the desired sequence.

Another aspect of the present invention provides a specialized app with a machine learning algorithm based on pathogen-specific training image data sets for analyzing exclusive properties mapped to the upstream experimental significance and eventually the decision making based on the analysis offers with unique features of the integrated device.

Another unique aspect of the present invention is that it comprises a pre-programmable thermal control unit capable of inducing designed temperature-time characteristics. This module is not specific to a particular thermal protocol for detecting a specific pathogenic DNA/RNA, but generic enough to be adopted to test-specific thermal protocols for detection of other microorganisms. Further, low-cost materials such as polydimethylsiloxane (PDMS), paper and Pyrex or similar materials have been tested to be adequate for constituting the thermally activated reactive microchamber. Integration of a decisive key step of genomic probe-based detection on a specially functionalized paper strip adds to improved accuracy of the test results. No prior art methodologies have disclosed any PDMS/paper/Pyrex-based microchamber in a portable device for isothermal amplification of the targeted RNA mixed reaction analytes to achieve the amplified c-DNAs. Seamless integration of the microchamber unit with the paper strip ensures spontaneous dispensing of the sample on to the assay strip, without necessitating manual intervention.

The present invention has introduced, for the first time, a piecewise isothermal amplification reaction seamlessly coupled with a complementary DNA probe-based detection as a combined single-user step procedure implementable in a generic pre-programmable customized device for highly accurate and unambiguous test results. This test relies upon RT-LAMP mediated amplification and subsequent detection of the amplified products by specific hybridization with a complementary DNA oligonucleotide. The method consists of three distinct and extremely generic conceptual reaction steps from RNA analysis to test result dissemination.

First, RT-LAMP reaction in presence of biotinylated forward inner primer (FIP-5'Bt) results in generation of 5' biotinylated RT-LAMP products. Second, a 6-fluorescein amidite (6-FAM) labelled DNA oligonucleotide (probe), complementary to the loop regions of the RT-LAMP products, is hybridized through consecutive heat denaturation and annealing process thereby generating dual labelled (Biotin+FAM) products. Third, the dual labelled products and the single labelled free probes get separated on a lateral flow assay strip and captured by the streptavidin and anti-FAM antibody immobilized on the test line and control lines, respectively. The second step acts as a key step towards improving the test specificity via a route that, in contrast to the RNA-mediated CRISPR-Cas based detection, solely relies on DNA probe hybridization, having obvious benefits of inherent stability even outside the ambit of controlled laboratory ambience.

Cas is an endonuclease enzyme that cuts the DNA at a specific location directed by a guide RNA. This is a target-specific technique that can introduce gene knock out or knock in depending on the double strand repair pathway. Engineered CRISPR systems contain two components: a guide RNA (gRNA or sgRNA) and a CRISPR-associated endonuclease (Cas protein). The gRNA is a short synthetic RNA composed of a scaffold sequence necessary for Cas-binding and a user-defined ~20 nucleotide spacer that defines the genomic target to be modified.

The present method overcomes the constraints of the CRISPR-Cas based detection as attributed to the low stability and hence shorter shelf life of sgRNA, which act as serious bottlenecks against implementation without stringent laboratory-based control. Further, sgRNAs are well known for their off-target effects, which may result in false-positive or negative results. Reagents with such reported artifacts are not used in the present test.

Another unique aspect of the invention is to provide a one-step thermal protocol that seamlessly integrates the RT-LAMP mediated amplification of the pathogen associates nucleic acid and hybridization of the 6-FAM labelled DNA probe together without requiring any user intervention in between.

Unique coupling of the reaction chamber and the detection unit in the portable platform avoids manual intervention for dispensing the amplified sample onto the sample pad of the colorimetric detection strip. This is ensured by designing a seamless fluidic pathway using a microfluidic dispensing technique. This eliminates manual pipetting of the sample onto the detection unit. A unique design of the sample introducing chamber ensures that the amplified samples can be introduced directly by pushing the microchamber forward to a position just above the sample pad for direct immobilization of the sample onto the paper strip.

Another unique aspect of this invention is a single step RNA isolation protocol that could be coupled with the one step amplification-detection reaction to present a simple "sample-to-result" solution for the detection of pathogenic infection with all the pertinent steps formatted in a customizable piece-wise isothermal testing format in a pre-programmable portable device unit.

A smartphone integrated analytical platform is coupled with the detection unit for implementing machine-learning enabled decision-making features premised on image analysis and algorithms. This not only results in a seamless dissemination of test results (positive, negative, or indecisive) but also ensures efficient data management in the cloud to act as a pointer to medical decision making for community-level interventions.

Real-time PCR based detection relies upon highly expensive reagents and consumables which increases the overall cost of the detection. The present invention provides a method relying upon a single DNA polymerase Bst3 along with multiple sets of primers.

Additionally, the detection is performed on functionalized paper based strips instead of complex instrumentation-based detection, which reduces the overall cost per experiment to a significant extent without sacrificing the accuracy of the test.

The existing RT-LAMP protocols, employed for detection of pathogen associated nucleic acids, relies either upon indirect pH based colorimetric or fluorescence-based detection techniques which makes the results ambiguous and difficult to interpret. The present invention, on the other hand, provides a device to detect the thermally amplified genomic products through specific hybridization with a complementary DNA probe that makes the detection precise and unambiguous.

A further aspect of the present invention provides a detailed method for SARS CoV-2 detection involving the portable POC device which is carried out comprising:
(i) providing biotin labelled primer sets, hybridization probes and other reagents in an airtight said reaction microchamber including samples (including either non-specific RNA or viral RNA/COVID-19 specific RNA).
(ii) switching on the said thermal control unit for heating the block from room temperature to the targeted temperature of 62-68° C., preferably about 65° C.;
(iii) once the desired temperature is reached, the microchambers hosting the reaction mixture are placed onto the isothermal heating block.
(iv) continuing said isothermal heating for the next 25 to 35 minutes preferably about 30 minutes whereby the RNA gets converted into cDNA and subsequently gets amplified into millions-billions of copies.
(v) after completion of the amplification cycle at said about 65° C., the device ramps up to reach the temperature of 93-98° C. preferably about 95° C. and termination cycle of 3-8 minutes preferably about 5 minutes at 95° C. continues, said heating cycles being performed automatically without requiring any manual intervention.
(vi) after the termination cycle is over, the heating system automatically ramps down to the temperature of 48-55° C. preferably about 50° C. which is required for the hybridization cycle and this cycle carried out for specific binding of the probe to the amplified target DNA.
(vii) after completion of the reaction procedure, the microchambers are pushed forward to the dispensing position using the cartridge and guided rail mechanism and keep the microchambers to cool down to the room temperature automatic/automatic manner by pushing the microchamber holder through a guided rail synchronized.
(viii) introducing the products from the above step onto the sample pad of the paper platform which is carried out in a semi-automatic manner with respect to the paper platform whereby the microchamber is placed in between the dispensing arrangement and the sample introducing chamber and releases the solution onto the sample pad using a needle valve.
(ix) allowing the sample flow through the paper matrices due to the capillary action by the force of surface tension and reach out to the conjugate section wherein the colloidal surface plasmon nanomaterial conjugated anti-FAM antibody binds with the targeted dual labelled amplified cDNA and the conjugate-DNA complex further flows downwards to the reaction area where streptavidin and anti-FAM secondary antibodies are immobilized at the test line and control lines of the strip, respectively.
(x) while flowing from the sample pad, the amplified conjugate-DNA complex reaches the test line and binds with the streptavidin for producing the color by the concentration of the colloidal nanomaterials attached to the same. The free nanomaterial-antibody conjugates bypass the test line and reach the control line to bind with the immobilized anti-FAM secondary antibodies and produce the color of the nanomaterial to enable the detection involving said imaging and dissipation means including a smartphone device.

Still further aspect of the present invention provides a method wherein the time duration for the exclusive step of colorimetric detection on the paper platform is within 10 minutes. The smartphone app is activated for capturing images of the reactions visible at the control line and test line of the paper strip, based on programmed camera properties, subsequently analyzing the same and displaying the final results onto the smartphone screen.

Yet another aspect of the present invention provides a method for COVID 19 detection, wherein said primer modifications were carried out involving sequences as hereunder:

| Target Region | Primer | Sequence (5' to 3') | Primer Modification |
|---|---|---|---|
| ORF 1b | F3 SEQ. ID No. 1 | GCCATTAGTGCAAAGAATAGAGC | |
| | B3 SEQ. ID No. 2 | GGCATGGCTCTATCACATTTAGG | |
| | FIP (F1c + F2) SEQ. ID No. 3 | TAGCTCCTCTAGTGGCGGCTATTGCACCGT AGCTGGTGTCTC | 5'-[Btn] |
| | BIP (B1c + B2) SEQ. ID No. 4 | TGTAGTAATTGGAACAAGCAAATTCTATGG TGGCCAACCCATAAGGTGAGGG | |
| | Loop F SEQ. ID No. 5 | TTTTTGATGAAACTGTCTATTGGTCATAGT ACTACAG | |
| | Loop B SEQ. ID No. 6 | GGCACAACATGTTAAAAACTGTTTATAGTG ATGTAG | |
| | BLP Probe SEQ. ID No. 7 | TTGGCACAACATGTTAAAAACTGTTTATAG TGATG | 5'-[6FAM] |
| | BLP 3'-mod Probe SEQ. ID No. 8 | TTGGCACAACATGTTAAAAACTGTTTATAG TGATG | 5'-[6FAM], 3'-[3d_G] |
| | FLP Probe SEQ. ID No. 9 | GCGGCTATTGATTTCAATAATTTTTGATGA AAC | 5'-[6FAM] |
| N gene | F3 SEQ. ID No. 10 | ACAATGTAACACAAGCTTTCG | |
| | B3 SEQ. ID No. 11 | TTGGATCTTTGTCATCCAATT | |
| | FIP (F1c + F2) SEQ. ID No. 12 | GGCCAATGTTTGTAATCAGTTCCTTAGACG TGGTCCAGAACAA | 5'-[Btn] |
| | BIP (B1c + B2) SEQ. ID No. 13 | GCTTCAGCGTTCTTCGGAATCACCTGTGTA GGTCAACC | |
| | Loop F SEQ. ID No. 14 | TGGTCCCCAAAATTTCCTTGG | |
| | Loop B SEQ. ID No. 15 | CGCGCATTGGCATGGAAGT | |
| | BLP Probe SEQ. ID No. 16 | TTGGCATGGAAGTCACACCTTC | 5'-[6FAM] |
| | BLP 3'-mod Probe SEQ. ID No. 17 | TTGGCATGGAAGTCACACCTTC | 5'-[6FAM], 3'-[3d_C] |
| | FLP Probe SEQ. ID No. 18 | GATTAGTTCCTGGTCCCCAAAATTTCC | 5'-[6FAM] |
| E gene | F3 SEQ. ID No. 19 | TTGTAAGCACAAGCTGATG | |
| | B3 SEQ. ID No. 20 | AGAGTAAACGTAAAAGAAGGTT | |
| | FIP (F1c + F2) SEQ. ID No. 21 | CGAAAGCAAGAAAAGAAGTACGCTAGTAC GAACTTATGTACTCATTCG | 5'-[Btn] |
| | BIP | GGTATTCTTGCTAGTTACACTAGCCAAGAC | |

-continued

| Target Region | Primer | Sequence (5' to 3') | Primer Modification |
|---|---|---|---|
| | (B1c + B2) SEQ. ID No. 22 | TCACGTTAACAATATTGC | |
| | Loop F SEQ. ID No. 23 | ATTAACGTACCTGTCTCTTCCGAAA | |
| | Loop B SEQ. ID No. 24 | ATCCTTACTGCGCTTCGATTGTGTG | |
| | BLP Probe SEQ. ID No. 25 | ATCCTTACTGCGCTTCGATTGTGTG | 5'-[6FAM] |
| | BLP 3'- mod Probe SEQ. ID No. 26 | ATCCTTACTGCGCTTCGATTGTGTG | 5'-[6FAM], 3'-[3d_G] |
| | FLP Probe SEQ. ID No. 27 | ATTAACTATTAACGTACCTGTCTCTTCC | 5'-[6FAM] |
| RNaseP | F3 SEQ. ID No. 28 | TTGATGAGCTGGAGCCA | |
| | B3 SEQ. ID No. 29 | CACCCTCAATGCAGAGTC | |
| | FIP (F1c + F2) SEQ. ID No. 30 | GTGTGACCCTGAAGACTCGGTTTTAGCCAC TGACTCGGATC | 5'-[Btn] |
| | BIP (B1c + B2) SEQ. ID No. 31 | CCTCCGTGATATGGCTCTTCGTTTTTTCT TACATGGCTCTGGTC | |
| | Loop F SEQ. ID No. 32 | ATGTGGATGGCTGAGTTGTT | |
| | Loop B SEQ. ID No. 33 | CATGCTGAGTACTGGACCTC | |
| | BLP Probe SEQ. ID No. 34 | CATGCTGAGTACTGGACCTCG | 5'-[6FAM] |
| | FLP Probe SEQ. ID No. 35 | ATGTGGATGGCTGAGTTGTT | 5'-[6FAM] |

Importantly, in keeping with a further aspect of the present advancement, the primer design of the test reagents is made exclusive to enhance the specificity and sensitivity in tune with DNA-probe-hybridization mediated specific probing step introduced under the present advancement as a seamless one-step procedure integrated with the piecewise-isothermal test format. As an essential measure to ensure that, all the outer primers are designed to be non-AT rich with the melting temperatures ranging in between 55° C. to 65° C. Lengths of the amplicons are kept within 200 base pairs and distance between the F2 to F1 and B2 to B1 are maintained within 40-60 base pairs. Additionally, during primer design, the potential dimer formation ability between the biotinylated FIP and FAM labelled probes is evaluated, which could otherwise lead to false positive signals in lateral flow assay. The cross reactivity between different sets of primers, DNA probes and their gene targets is also tested. All these criteria have been highly selective for the desired performance of the seamlessly coupled RT-LAMP reaction backbone with DNA probe hybridization and LFA based detection of the advancement, to enhance specificity and sensitivity of the test as compared to the naïve RT-LAMP format.

Following examples illustrate the present invention in further detail.

EXAMPLES

Figure 2:
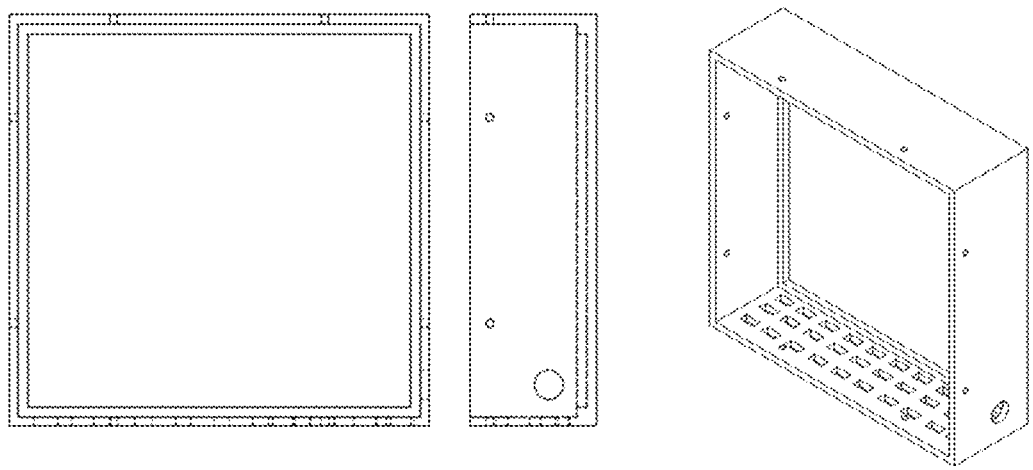
FIG. 2 illustrates schematic drawing of the part (1) of the device marked in FIG. 1. This is the base cover of the device for accommodating all the components for the isothermal heating unit.
Figure 3:
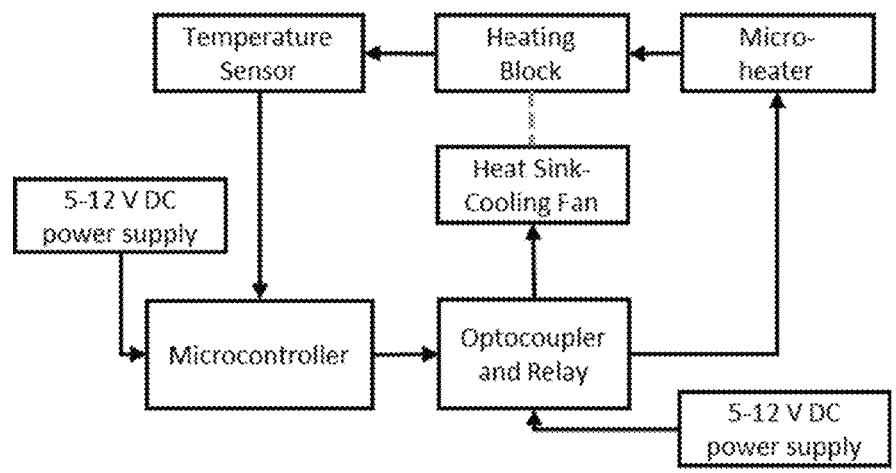
FIG. 3 illustrates functional block diagram of the isothermal heating unit comprising a heating block, micro-heater, temperature sensor, heatsink-fan assembly, microcontroller and optocoupler-relay unit.
Figure 4:
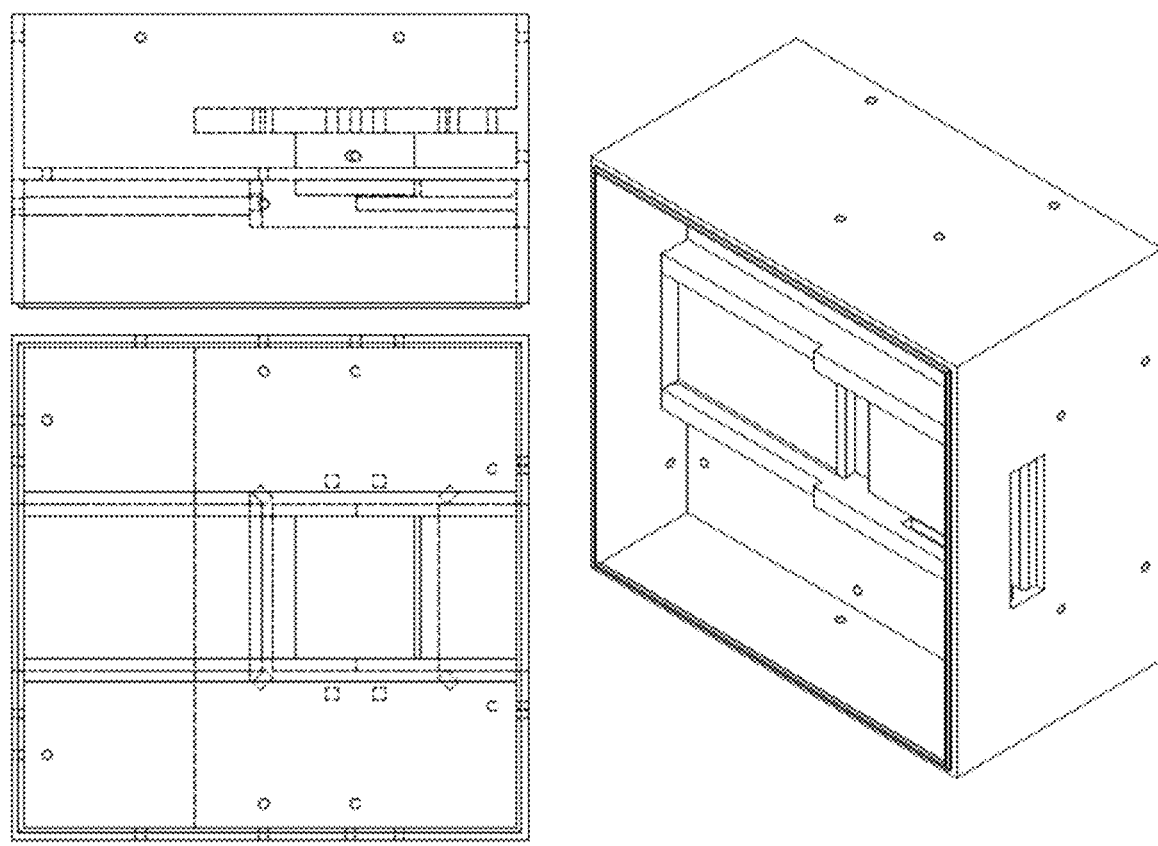
FIG. 4 illustrates the design drawing of the middle part of the device that includes guided rail arrangement for insertion of microchamber and paper-strip. This part also accommodates the fluid dispensing unit, heating block.
Figure 5:
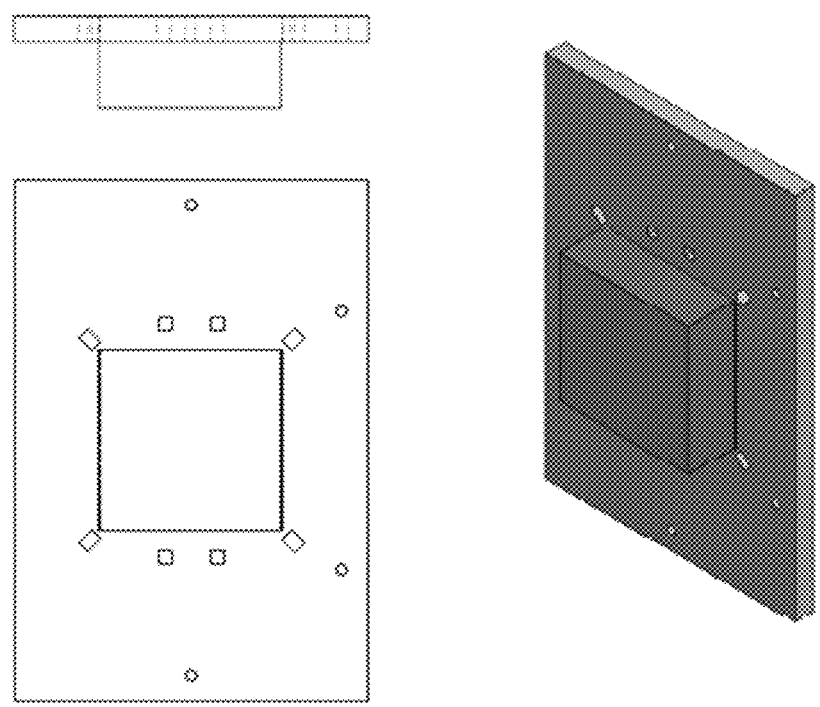
FIG. 5 illustrates an embodiment of the part (2) marked in FIG. 1 with heating block and heat sink holding arrangement.

Example 1: Sample-to-Answer Portable POC Device for Detection of Viral RNA i) Exemplary Illustration of the Integrated Portable Device: The RT-PCR simplified portable device is specially designed for seamless integration of all the functionalities together to perform sequential events for execution of the entire detection process (FIG. 1). According to an exemplary embodiment, the outer cover of the device is fabricated using 1.1 mm thick mild steel sheet to ensure structural robustness without sacrificing economy of manufacturing. The top cover, paper-strip cartridge and microchamber holding cartridges are developed using additive manufacturing technology with a 3D printer (TECH B V30, India). This production is up scalable via injection moulding for rapid and inexpensive fabrication. The device included a simplified isothermal heating unit with pre-programmable temperature control for RT-LAMP based simultaneous reverse transcription followed by c-DNA amplification from the RNA mix solution into the microchamber. The aluminum heating block (2) with a cartridge heater and a temperature sensor is inserted into it and the block is seated on the heat-sink fan assembly fixed on a platform over the part (1). The thermal reaction block (heating unit), made of aluminium, was drilled with the numbers of slots same as the numbers of test reactions that may be run in parallel. This aspect of the design is completely flexible and hallmarked by unrestricted scalability, at the expense of altering the size of the device. The microchamber (4) was fabricated using transparent polymers. Materials like polydimethylsiloxane (PDMA), PMMA and Pyrex are considered for this purpose in different versions of the test instrument, with no perceptible difference in the outcome. The microchamber (4) for amplification of RNA was seated on a cartridge (3) and the assembly inserted through a guided rail for positioning the microchamber on the heating block (2). The microchamber (4) with amplified RNA mix product can then further be inserted through the guided rail assembly and precisely positioned in between the microfluidic dispenser and the paper strip. The fluid dispensing mechanism (5) may be implemented via either automated or manual arrangement for dispensing amplified c-DNA product and buffer solution onto the sample pad of the paper-strip (7). The paper-strip was encapsulated within a transparent cassette and fixed on another cartridge (6) which can be inserted through the guided rail assembly to a desired position for automated dispense of the products from microchamber. The guided rail assembly (8) was designed for seamless integration of the thermal reaction unit with the detection unit. The top cover (9) has a viewing window covered with a transparent Pyrex or glass or other non-brittle materials for monitoring the isothermal heating of the RNA mix samples. A smartphone can be put onto the transparent window within a marked area for image acquisition of the colorimetric change of the reaction strip on the paper platform.

ii) Exemplary Illustration of the Thermal Control Unit:

A thermal control unit was generically adapted and developed with capabilities of arbitrary multi-step isothermal processes that can be pre-programmed in a customized manner, and was thus established as a platform technology for implementing improvised RT-LAMP-based method. The complex thermal cycle used in RT-PCR for DNA amplification has been simplified in the said device with a pre-programmable piece-wise isothermal heating cycle. The functional block diagram of the said isothermal heating unit is represented in the FIG. 3 whereas FIG. 2 represents the lower part of the device for accommodating all the hardware of the heating unit. The hardware for thermal control according to the exemplary embodiment was obtained involving of an Arduino microcontroller, a 40 W heating cartridge, a DS18B20 one-wire temperature sensor, a fan with heat sink, optocoupler-relay (DC) unit, and a SMPS power unit. The rectangular or circular shaped aluminum heating block was machined and fixed with an arrangement in the middle part of the device (FIG. 4 and FIG. 5). A normally open relay was utilized for triggering alternately the heating of the block through the cartridge heater or cooling of the block through the fan-heat sink assembly. The heating block was attached to the fan-heat sink assembly with the help of thermal paste for effective thermal contact. Candle wax (locally sourced) was put in the tubule holder for ensuring good thermal contact. The Arduino program includes fetching the temperature data and executing one of the following three functions:

a) Raise the temperature to the targeted temperature—here the heater relay is actuated through an active low signal to an optocoupler. During this phase, the optocoupler to the cooling fan relay is set to high and remains off.

b) Hold the temperature to the desired value. This function consists of a temperature threshold so that the temperature is maintained within a specified +− range. Falling below T−dT actuates the heating relay while raising the temperature above T+dT actuates the cooling relay. The temperature oscillates between T+dT and T−dT; the oscillations are minimized due to the size of the thermal mass of the heating block. The total time of holding a particular desired temperature is also specified via pre-programming.

c) Lower the temperature—this function is similar to (a) but instead of actuating the heating circuit, the cooling circuit is actuated. The temperature is read every 3 seconds and redundancy temperature sensor checks are made to ensure no signal-scrambling through the one-wire interface.

Figure 6:
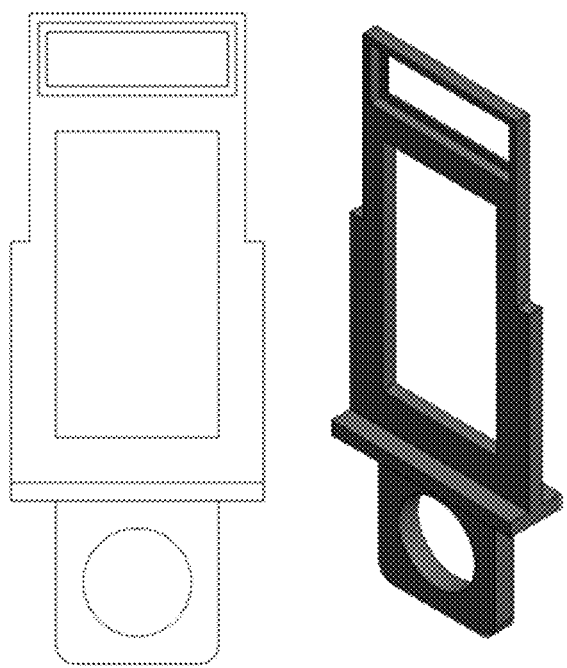
FIG. 6 illustrates an embodiment of the part (3) marked in FIG. 1 i.e. the cartridge for holding the microchamber and insert into the device through the guided rail assembly.
Figure 7:
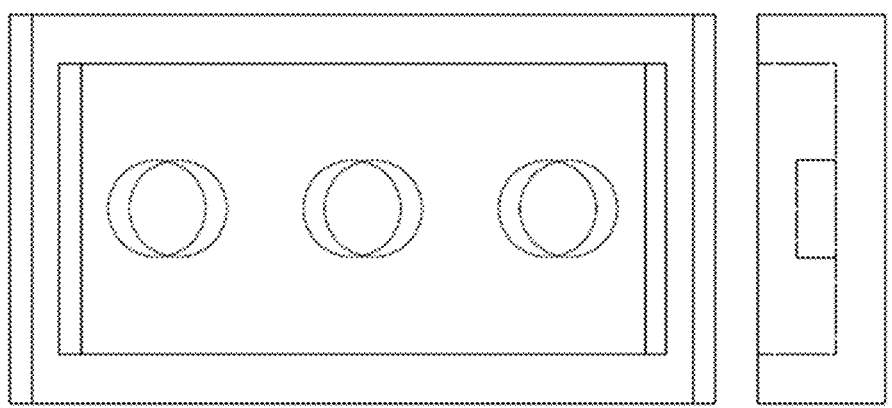
FIG. 7 illustrates an embodiment of the part (4) marked in FIG. 1 i.e. the microchamber for holding and isothermal amplification of DNA and RT-LAMP mixture.
Figure 8:
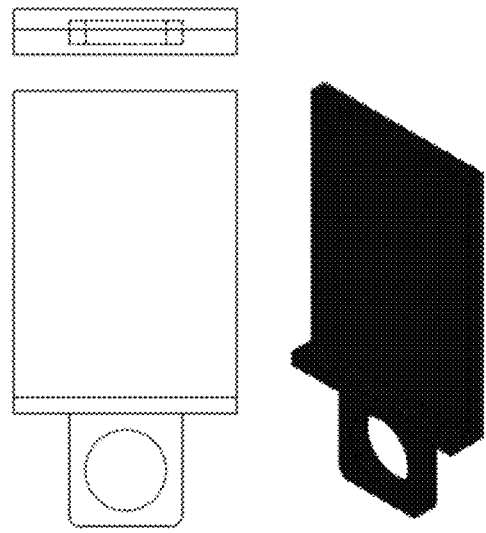
FIG. 8 illustrates an embodiment of the part (6) marked in FIG. 1 i.e the cartridge for holding the paper-strips and insert into the device through the guided rail assembly.

The advantage of utilizing an Arduino microcontroller is that it allows for LCD display of real-time temperatures, easy integrability, temperature logging, as well as smartphone and web-based applications. The entire assembly is found to be extremely easy to operate and adaptable as per user requirements, obviating the need of specially-trained laboratory technicians.

iii) Exemplary Illustration of Microchamber:

The microchamber according to an exemplary embodiment is adapted and developed for isothermal heating of a reactant system to amplify the RNA into c-DNA for subsequent colorimetric detection of the targeted pathogen (FIG. 7). The microchambers are circular or rectangular or polygonal in shape and size may vary as per the volume to be amplified. There could be one or more microchambers in a single detection system. The material for fabrication of the microchamber is primarily polydimethylsiloxane/paper/Pyrex or similar biocompatible polycarbonates. The microchamber is fixed onto a cartridge (FIG. 6) for placing it onto heating block as it is the first stop position for the cartridge. The RNA mix sample is airtight sealed into the reaction chamber during the isothermal heating.

iv) Exemplary Illustration of the Functionalized Microfluidic Paper Platform:

For colorimetric detection of the target genomic material in the amplified c-DNA, the present invention provides specially functionalized microfluidic paper platform (FIG. 9). The said microfluidic paper platform is simulated by mimicking its properties in each section via computational fluid dynamics, for obtaining the optimum flow rate and reaction of the species based on the chosen paper grades and membranes constituting different sections of the lateral flow assay. This microfluidic paper platform comprises a circular/polygonal/similar shaped sample introducing chamber (part-a), a rectangular binding section for immobilizing the conjugates (part-b), a detection area includes a test line and a control line (part-c) and a waste absorbent section (part-d). The sample introducing part is made of nitrocellulose filter paper comprises a circular section integrated with a rectangular channel section. The construction of the sample introduction part is unique for seamless integration of dispensing of the amplified c-DNA product onto the sample introducing chamber. The binding or conjugate section of the paper device is made of glass fibers or similar materials. This binding area is immobilized with colloidal surface plasmonic nanomaterials (such as gold nanoparticles, nanoshells) conjugated with primary antibodies. The reaction area of the paper platform is made of a nitrocellulose membrane on which specific antibodies (for example, streptavidin and anti-FAM antibodies for COVID-19 detection) may be immobilized on two separate lines, seamlessly interfacing with a smartphone camera-based image grabbing unit (see later). Finally, the waste absorbing section is made of a blotting paper/material with high absorption capacity.

iv) Exemplary Illustration of Smartphone App-Based Image Processing and Result Display:

The smartphone-based android app works on a simple image processing algorithm and is very user-friendly. Different edge detection techniques with few object detection techniques are used to detect and identify the test lines and control lines from the paper-based test strip. An algorithm (Table 1) has been developed based upon some rule-based decision for optimization using machine learning approach for providing accurate decision about the presence or absence of the infection in terms of positive or negative result.

unit, which includes the isothermal amplification unit, performs the activity of reverse transcription of RNA to c-DNA followed by its amplification in the said device in a single user-step reaction. The thermal control unit controls the temperature of the aluminum heating block on which the RNA mix filled microchamber is situated. The microchamber is placed onto the surface of the heating block with the help of a cartridge inserted through a guided rail. An illustrative representation of the guided rail assembly is shown in the FIG. 10. The RNA mix solution is isothermally heated for performing biochemical reaction within the air-tight sealed microchamber to produce c-DNA product by the method of reverse transcription and loop-mediated isothermal amplification. On the other hand, the entire colorimetric detection process is executed by colorimetric detection unit and smartphone result display unit. The synchronization between the thermal control cum reaction unit and the

TABLE 1

The algorithm for interpretation of the test results.

| Sample case | Attempt-1 Possible result | | | | | Attempt-2 Possible result | | | |
|---|---|---|---|---|---|---|---|---|---|
| | RNaseP | ORF-1b | N gene | Inference | Remarks | RNaseP | ORF-1b | N gene | Conclusion |
| 1 | − | − | − | Test not valid | Repeat test | + | − | − | Negative |
| | | | | | | + | + | + | Positive |
| | | | | | | − | + | + | Repeat test with freshly collected sample. |
| 2 | − | + | + | Positive | Conclusive | | | | |
| 3 | + | + | + | Positive | Conclusive | NA | NA | NA | NA |
| 4 | + | − | − | Negative | Conclusive | NA | NA | NA | NA |
| 5 | + | + | − | Presumptive positive | Repeat test | + | + | + | Positive |
| | | | | | | + | + | − | Positive |
| | | | | | | + | − | − | Negative |
| 6 | + | − | + | Presumptive positive | Repeat test | + | + | + | Positive |
| | | | | | | + | − | + | Positive |
| | | | | | | + | − | − | Negative |

The android app (named as COVIRAP) was developed based on the interpretation algorithm in the Table 1 on the API level 21 to 30 used in most of the available commercial smartphones. The user-friendly smartphone app performs multiple important functionalities starting from image capturing, machine learning-based analysis and processing, display of the final result and in parallel send the data to the cloud server. The overall workflow of the smartphone app is given in FIG. 11. These features are generic and can be implemented in other smartphone platforms as well. Arresting the possibilities of false reaction signal by using training sets of images of true and falsified test results via dynamic machine learning is another feature of the mobile app that improves the overall efficacy of detection.

v) Exemplary Illustration of Integration of Multiple Functionalities into a Simplified Portable Device:

The entire process of pathogen associated nucleic acids detection using the portable device is performed by synchronizing two major functionalities of the RT-LAMP based isothermal amplification with functionalized paper-based colorimetric detection together on a single platform. There are four functional modular units to execute these two separate functionalities represented in the functional block diagram in the FIG. 12. The thermal control cum reaction colorimetric detection unit is done by the guided rail assembly for smooth transition of the microchamber from the heating block to the position to dispense the amplified sample onto the sample introducing area of the paper strip. The cartridge with microchamber is pushed forward after completion of the isothermal heating to its second stop in between the fluid dispenser and the paper strip. The needle valve based microfluidic dispenser releases the amplified solution from the microchamber onto the sample introducing area of the paper strip to flow downstream for detection in the test line and control line by colorimetric reaction process. The smartphone is placed in its designated place onto the top window of the device for image capturing after generation of colored lines on the paper strip. The android app processes the captured image and displays the decision on smartphone screen after analyzing the colorimetric reaction with the in-house developed image processing algorithm.

The complete implementation of the workflow from sample collection to result dissemination using the portable device unit is represented in FIG. 13 and FIG. 14. This generic workflow is applicable to any arbitrary nucleic acid based detection protocols (including the RT-LAMP-CRISPR method) where isothermal amplification products are detected using LFA based detection method. (1) The body fluid sample collected from the patient may either be used to extract RNA using established methods or alternatively subjected to a brief heating step which can be performed in heating slots present in the device. (2) The purified RNA or the heat lysed sample is subsequently mixed with the test reagents generically containing primers, probes and enzymes and dispensed altogether in dedicated reaction-chambers. (3) The reactions are held in the portable device under pre-programmed piecewise isothermal time-steps without intermediate manual intervention (4) The final products are dispensed onto the LFA paper strips and the colorimetric readouts developed therein are captured using a smartphone camera, for subsequent image analytics and algorithmic implementation and rapid dissemination of the test outcome.

Example 2: Method of Detection of RNA Virus by the POC Device

The experimental procedure has been successfully tested for detection of influenza A and COVID-19 virus. For illustration, SARS-CoV-2 specific experimental details are given below. Notably, differences between the procedures of testing different pathogenic infections merely lie in the use of specific primers, DNA probes and specific hybridization temperature within the same overall framework (FIG. 15A). The isothermal amplification reaction mixture for SARS-CoV-2 detection is prepared using NEB WarmStart LAMP kit, #1700s (for fluorescence, agarose gel electrophoresis and paper strip based detection) or NEB WarmStart Colorimetric LAMP 2× Master mix #1800s (for visual detection) by adding up biotinylated forward inner primer (FIP-5'Bt) sets (seq.no, 3, 12, 21 and 30 for ORF1B, for N gene, E gene, RNase P respectively), 6-fluorescein amidite (6-FAM) labelled DNA oligonucleotide (probes of Seq.no.7 and 9; 16 and 18, 25 and 27; 34 and 35 for ORF1B, for N gene, E gene and RNaseP gene respectively) or dual modified (5'-FAM and 3' ddNTP) complementary DNA probes (Seq. ID.No. 8, 17 and 26 for ORF1B, N gene, E gene respectively) and other reagents as directed by the manufacturer in an airtight reaction microchamber.

Either non-specific RNA or 'in vitro synthesized SARS-CoV-2 specific RNA', or RNA extracted from suspected human patient samples was added to separate microchambers as for comparison of positive and negative results. First, the device is switched on for heating the block from room temperature to the targeted temperature of 65° C. The ramp-up time for reaching the target temperature is 4-5 minutes. Once the desired temperature is reached, the microchambers hosting the reaction mixture are placed onto the isothermal heating block. The isothermal heating of the system continues for the next 25-35 minutes preferably for 30 minutes. During this period, the RNA gets converted into c-DNA and subsequently gets amplified into millions of copies. After completion of the amplification cycle at a temperature of 62-68° C. preferably about 65° C., the device ramps up in ~4 minutes to reach the temperature of 93-98° C. preferably about 95° C. and termination cycle of 3-8 minutes preferably about 5 minutes at 95° C. continues. All these heating cycles are designed to be performed automatically without requiring any intervention by the user. After the termination cycle is over, the heating system automatically ramps down to 48-55° C. preferably about 50° C. which is required for the hybridization step. This step carries out specific binding of the probe to the amplified target DNA. After completion of the reaction procedure, the microchambers are pushed forwards to the second stop and cooled down to the room temperature. The samples are now ready for introducing onto the sample pad of the paper platform. This step is done in a semi-automatic manner by pushing the microchamber holder through a guided rail synchronized with the paper platform. The microchamber is placed just above the sample introducing chamber of the paper strip and releases the solution onto the sample pad with the aid of a microfluidic dispenser (needle valve). Sample flows through the paper matrices due to the capillary action by the force of surface tension and reaches out to the conjugate section. Here, the colloidal gold conjugated Anti-FAM antibody binds with the targeted DNA and the amplified labeled DNA complex further flows downwards to the reaction area where streptavidin and anti-FAM secondary antibodies are immobilized at the test line and control lines of the strip, respectively. While flowing from the sample pad, the amplified DNA complex reaches the test line and binds with the streptavidin for producing the color by the concentration of colloidal gold nanoparticles/nanoshell attached to the same. The free gold nanoparticles/nanoshell-antibody conjugates bypass the test line and reach the control line to bind with the immobilized anti-FAM secondary antibodies and produce the color of colloidal nanoparticles/nanoshells. The time duration exclusive for colorimetric detection on the paper platform is within 10 minutes. After 5-10 minutes of sample introduction onto the paper strip, the smartphone app is activated for capturing images based on programmed camera properties, subsequently analyzing the same and displaying the final results onto the smartphone screen.

Results:

Standardization of the Protocol for the Detection of SARS-CoV-2 Genomic RNA:

To detect SARS-CoV-2 infection using this method, three highly conserved target regions have been identified in the SARS-CoV-2 genomic RNA that reside within the RNA dependent RNA polymerase (RdRp/ORF1b) gene (ORF1B), the nucleocapsid (N) gene and the envelope (E) gene (FIG. 15A and FIG. 16). Choices of such multiple highly conserved regions remain imperative and critical amidst the dynamically mutating strains of the infecting pathogen. Individual sets of RT-LAMP primers with high specificity against the target regions (FIGS. 16 A and B) were designed to detect and amplify each of the target regions.

Short in vitro-transcribed (IVT) RNA fragments mimicking the gene targets mentioned above were first used for the standardization of the RT-LAMP reactions (FIG. 15B upper panel). Primers specific to human RNaseP gene were used as internal control. For complementary DNA probe-based detection via LFA, 6-FAM labelled forward and backward loop probes (FLP and BLP) for each set of viral genes and RNaseP were designed and tested their ability to specifically detect the corresponding RT-LAMP reaction products. BLPs, against all of the target genes, exhibited highly specific detection in the form of the test line on the paper strips which was absent in the negative control sets. FLPs, in contrast, showed weak to moderate nonspecific signals even in the negative control sets for N, E and RNaseP genes (FIG. 15B, lower panel), which could be attributed to partial complementarity of 6-FAM labelled probes with biotin labelled primers. For subsequent experiments, BLPs were therefore used for specific probing and LFA based detection procedure.

Next, the cross reactivity of individual set of primers and probes were tested against the non-target RNA sequences. RT-LAMP primers designed for one target gene of SARS-CoV-2 showed no cross reactivity against other gene targets (FIG. 15C, upper panel). Additionally, the products amplified from one gene target could only be detected with the corresponding BLPs (FIG. 15C, lower panel), ensuring the high specificity of our double layered detection method. The method also showed no cross reactivity against the genomic RNAs of other corona viruses including SARS, OC43, NL63, 229E and HKU1 (FIG. 17B) as well as other RNA viruses like Influenza A, Influenza B or Japanese Encephalitis Virus (JEV) genomic RNAs (FIGS. 17A and B) and hence confirmed that it can specifically detect and distinguish SARS-CoV-2 infection from infections caused by other viruses with similar clinical presentations.

In vitro sensitivity assay was performed to ascertain the limit of detection (LOD) of the present method for individual target genes. Individual reaction sets containing 104 to 1 copy per microliter of the contrived RNA samples were then subjected to the test reaction protocol in sextuplets. Primers and probes corresponding to all of the gene targets showed the ability to consistently detect 100 copies of RNA molecules in six out of six replicates (FIG. 18A and FIG. 19). For the replicates containing 10 copies of RNA, N gene, RdRp/ORF1b and E gene primer sets showed 5/6, 4/6 and 3/6 positive detections, respectively, suggesting the following order of sensitivity: Target 1(RdRp/ORF1b)>Target 2(N)>Target 3(E). All of the gene targets exhibit inconsistent results for higher dilutions suggesting a limit of detection as 10 copies per microliter. Summarily, the generic method demonstrated the capability of detecting 10 copies of viral RNA reliably for majority of replicates and 100 copies of viral RNA for all of the replicates, which is comparable to or superior to other RT-LAMP based detection technologies reported for similar applications.

Field Validation Test for the Detection of SARS-CoV-2 Infection in Patients Under Resource Limited Settings:

The high specificity and sensitivity of the test in the in-vitro experiments prompted to evaluate its efficacy in detecting the presence of SARS-CoV-2 genomic RNA in the nasopharyngeal swab samples isolated from patients. For this purpose, an experimental model was set up which could mimic performing the diagnostic procedure in a remote location in resource limited setting. The ready-to-use reaction-mixes in the forms of packed test kits were pre-aliquoted and were transported from the lab to the patient sample testing center over a road-travel duration of several hours and subsequently stored in a normal refrigerator at 4° C. overnight before performing the test procedure (FIG. 20). Purposefully, no specific attention was laid to perform the test in controlled ambience.

RNA extracted from 200 double-blinded patient samples were used, among which 115 were positive and 85 were negative for SARS-CoV-2 infection as determined by the ICMR-NIV developed RT-PCR assay, with the Ct values distributed in between the range of 15 and 35. Primers specific to N gene and RdRp/ORF1b(ORF1B) were employed to detect the presence of viral RNA as these two target gene sets showed higher sensitivity than E gene target (FIG. 18A). RNaseP was used as internal control. All the test reactions were performed using the portable instrument and the final results were recorded and analysed with the help of the custom-made app trained with the algorithm mentioned in Table 1. Briefly, a test with both the gene targets showing positive results was considered as infection positive while negative results with both of them confirm negative infection. For samples (observed mostly with high CT values) with one gene target showing positive and other showing negative results, the test was repeated and repetition of the exact same trend confirmed positive infection (FIG. 18B).

Considering all 200 patient samples, our method showed a positive percentage agreement 93.91% and negative percent agreement 97.64% (FIG. 18C, D and Table 2). However, for the samples of Ct values 30 and below, which acts as a suitable reference for clinical decision making, the positive percent agreement values reached to 98.79%. To overrule the cross reactivity of the assay, SARS-CoV-2 negative panel (n=85) included 10 known influenza A positive nasopharyngeal samples. All the Influenza positive samples showed negative results for the presence of SARS-CoV-2. This data confirms that the test is capable of detecting SARS-CoV-2 infection in patient samples with high, moderate and low viral loads with superior sensitivity and specificity in contrast to other LAMP-based detection technologies. Additionally, the present experimental model confirms that the present test method is suitable to be implemented in the remote areas with limited infrastructure and resources.

TABLE 2

Present test result for patient-sample based validation of SARS-CoV-2 infection.

| | Ct value | <=25 | >25 to 30 | >30 to 35 | Negative |
|---|---|---|---|---|---|
| True | Positive | 59 | 24 | 25 | N/A |
| | Negative | N/A | N/A | N/A | 83 |
| False | Positive | N/A | N/A | N/A | 2 |
| | Negative | 0 | 1 | 6 | N/A |
| Sensitivity | | 100% | 96.15% | 80.65% | N/A |
| Specificity | | N/A | N/A | N/A | 97.65% |

One step sample-to-result integration for detection of RNA-signature infection via single step swab/saliva-to-result protocol was standardized that could be implemented without changing the basic principle of the generic test-bench and work-flow of the present invention. This endeavor obviates the tedious workflow of RNA isolation or any intermediate steps, like intermediate addition of DNA probes in the protocol, facilitating implementation in point-of-care setting.

For this purpose, an integrated approach for detecting genomic RNA directly from the pathogenic particles or from the infected cells using Influenza A virus as a model system was incorporated in the device. The present protocol, for that purpose, was standardized for detecting the segment seven (open reading frame M2) of influenza A/H1N1/WSN/1933 virus genomes (Table 3) using extracted RNA samples (FIG. 21). Subsequently, experiments were performed where influenza A virus infected human lung epithelia cells (A549) were re-suspended in phosphate buffer saline (PBS) spiked with the saliva collected from an infection negative donor. A saliva-PBS suspension containing 100 such cells was then subjected to a brief pre-heating step (93-98° C. preferably about 95° C. for 2-5 minutes preferably about 3 minutes) in the portable instrument before being used as an input for the subsequent steps of the protocol. This heating step was likely to cater multifarious objectives including sample homogenization, breaking up the viral capsid and inactivation of the inhibitory enzymes present in human saliva. This adapted protocol was successful in consistently detecting both influenza virus RNA as well as the RNaseP mRNA from the heat ruptured cell lysate either in absence or presence of saliva (0.5% final concentration) (FIG. 22A and FIG. 23). Additionally, this protocol could detect as low as 500 influenza virion particles (measured in terms of plaque forming units-PFU) diluted in PBS without any additional RNA extraction process in absence of saliva (FIG. 22B and FIG. 24). In dilution containing saliva (0.5% final concentration), the method shows a sensitivity of 2500 plaque forming units which is much lower than the usual viral load in a patient showing clinical symptoms.

The limit of detection (LOD) as ascertained for SARS-CoV-2 N gene target in the presence and absence of saliva. Tenfold serial dilutions of contrived N gene fragments were prepared either in PBS or in PBS spiked with saliva and subsequently subjected to the present procedure in sextuplets. Encouragingly, even in presence of saliva, the present method could successfully detect up to 100 and 10 copies of viral RNA in 5/6 and 4/6 replicates which is comparable to the saliva negative controls (FIG. 22C and FIG. 25). This ensures high sensitivity and robustness of the N gene target specific primers in amplifying corresponding gene fragment in stringent experimental conditions.

List of RT-LAMP Primers and Probe

| Target Region | Primer | Sequence (5' to 3') | Primer Modification |
|---|---|---|---|
| ORF 1b | F3 SEQ. ID No. 1 | GCCATTAGTGCAAAGAATAGAGC | |
| | B3 SEQ. ID No. 2 | GGCATGGCTCTATCACATTTAGG | |
| | FIP (F1c + F2) SEQ. ID No. 3 | TAGCTCCTCTAGTGGCGGCTATTGCACCGTAGCTGGTGTCTC | 5'-[Btn] |
| | BIP (B1c + B2) SEQ. ID No. 4 | TGTAGTAATTGGAACAAGCAAATTCTATGGTGGCCAACCCATAAGGTGAGGG | |
| | Loop F SEQ. ID No. 5 | TTTTTGATGAAACTGTCTATTGGTCATAGTACTACAG | |
| | Loop B SEQ. ID No. 6 | GGCACAACATGTTAAAAACTGTTTATAGTGATGTAG | |
| | BLP Probe SEQ. ID No. 7 | TTGGCACAACATGTTAAAAACTGTTTATAGTGATG | 5'-[6FAM] |
| | BLP 3'-mod Probe SEQ. ID No. 8 | TTGGCACAACATGTTAAAAACTGTTTATAGTGATG | 5'-[6FAM], 3'-[3d_G] |
| | FLP Probe SEQ. ID No. 9 | GCGGCTATTGATTTCAATAATTTTTGATGAAC | 5'-[6FAM] |
| N gene | F3 SEQ. ID No. 10 | ACAATGTAACACAAGCTTTCG | |
| | B3 SEQ. ID No. 11 | TTGGATCTTTGTCATCCAATT | |
| | FIP (F1c + F2) SEQ. ID No. 12 | GGCCAATGTTTGTAATCAGTTCCTTAGACGTGGTCCAGAACAA | 5'-[Btn] |
| | BIP (B1c + B2) SEQ. ID No. 13 | GCTTCAGCGTTCTTCGGAATCACCTGTGTAGGTCAACC | |
| | Loop F SEQ. ID No. 14 | TGGTCCCCAAAATTTCCTTGG | |
| | Loop B SEQ. ID No. 15 | CGCGCATTGGCATGGAAGT | |
| | BLP Probe SEQ. ID No. 16 | TTGGCATGGAAGTCACACCTTC | 5'-[6FAM] |
| | BLP 3'-mod Probe SEQ. ID No. 17 | TTGGCATGGAAGTCACACCTTC | 5'-[6FAM], 3'-[3d_C] |
| | FLP Probe SEQ. ID No. 18 | GATTAGTTCCTGGTCCCCAAAATTTCC | 5'-[6FAM] |
| E gene | F3 SEQ. ID No. 19 | TTGTAAGCACAAGCTGATG | |
| | B3 | AGAGTAAACGTAAAAGAAGGTT | |

-continued

| Target Region | Primer | Sequence (5' to 3') | Primer Modification |
|---|---|---|---|
| | FIP (F1c + F2) SEQ. ID No. 20 | CGAAAGCAAGAAAAAGAAGTACGCTAGTAC GAACTTATGTACTCATTCG | 5'-[Btn] |
| | BIP (B1c + B2) SEQ. ID No. 21 | GGTATTCTTGCTAGTTACACTAGCCAAGAC TCACGTTAACAATATTGC | |
| | Loop F SEQ. ID No. 22 | ATTAACGTACCTGTCTCTTCCGAAA | |
| | Loop B SEQ. ID No. 23 | ATCCTTACTGCGCTTCGATTGTGTG | |
| | BLP Probe SEQ. ID No. 24 | ATCCTTACTGCGCTTCGATTGTGTG | 5'-[6FAM] |
| | BLP 3'-mod Probe SEQ. ID No. 25 | ATCCTTACTGCGCTTCGATTGTGTG | 5'-[6FAM], 3'-[3d_G] |
| | FLP Probe SEQ. ID No. 26 | ATTAACTATTAACGTACCTGTCTCTTCC | 5'-[6FAM] |
| RNaseP | F3 SEQ. ID No. 27 | TTGATGAGCTGGAGCCA | |
| | B3 SEQ. ID No. 28 | CACCCTCAATGCAGAGTC | |
| | FIP (F1c + F2) SEQ. ID No. 29 | GTGTGACCCTGAAGACTCGGTTTTAGCCAC TGACTCGGATC | 5'-[Btn] |
| | BIP (B1c + B2) SEQ. ID No. 30 | CCTCCGTGATATGGCTCTTCGTTTTTTCT TACATGGCTCTGGTC | |
| | Loop F SEQ. ID No. 31 | ATGTGGATGGCTGAGTTGTT | |
| | Loop B SEQ. ID No. 32 | CATGCTGAGTACTGGACCTC | |
| | BLP Probe SEQ. ID No. 33 | CATGCTGAGTACTGGACCTCG | 5'-[6FAM] |
| | FLP Probe SEQ. ID No. 34 | ATGTGGATGGCTGAGTTGTT | 5'-[6FAM] |

TABLE 3

| | | | | |
|---|---|---|---|---|
| Influenza A (Segment 7) | F3 SEQ. ID No. 36 | GGGCTGTGACCACTGAAG | | |
| | B3 SEQ. ID No. 37 | AGCAATATCCATGGCCTC TG | | |
| | FTP (F1c+F2) SEQ. ID No. 38 | TGAGACCGATGCTGGGAG TCATGGCATTTGGCCTGG TATG | 5'-[Btn] | |
| | BIP (B1c+B2) SEQ. ID No. 39 | TGGTTCTAGCCAGCACTA CAGCCTGCTTGCTCACTC GATCC | | |
| | Loop F SEQ. ID No. 40 | GCAATCTGTTCACAGGTT GCG | | |
| | Loop B SEQ. ID No. 41 | TAAGGCTATGGAGCAAAT GGC | | |
| | BLP Probe SEQ. ID No. 42 | TAAGGCTATGGAGCAAAT GGCT | 5'-[6FAM] | |
| | FLP Probe SEQ. ID No. 43 | GCAATCTGTTCACAGGTT GCG | 5'-[6FAM] | |

The other exclusive aspect of saliva to result integration is combining the specific DNA probe hybridization step with the initial amplification step, thereby excluding any in-between manual intervention during the test reactions. For this purpose, the 6-FAM labelled complementary DNA probe (BLP) was added from very beginning of the reaction, resulting in a master-mix which contains all reaction components in it (enzyme mix, RT-LAMP primers, and DNA probe). Hence, mere addition of the input RNA to the master mix and subsequent initiation of the thermal protocol could result in dual labelled products which then could be subjected to direct detection. Although an attractive proposition, the initial addition of the DNA probe in the RT-LAMP reaction as an integrated single-step protocol necessitated additional safeguards as this could potentially lead to the concomitant amplification of the probe itself and hence might interfere with the amplification or specificity of the detection process. To avoid such adverse artefacts, double modified DNA probe harbouring 6-FAM and a di-deoxy nucleotide were included at its 5'- and 3'-termini respectively. Test reactions were performed in presence of either regular (5'-6-FAM) or dual modified (5'-6-FAM+3'-ddNTP) DNA probes and subsequently monitored. As evidenced, addition of either the 6-FAM or the 6-FMA-3'ddNTP probes from the very beginning of the reaction showed signal comparable to the conventional two-step detection procedure with no non-specific signals in negative control sets in either of these cases (FIG. 22D, FIG. 26 and FIG. 27). Together, this modification along with the body fluid-to result integration in the test protocol, when implemented with the help of the present device, holds the potential to revolutionize the nucleic acid-based detection of pathogenic infection and essentially bring high-end molecular diagnostics from sophisticated labs to the field where controlled laboratory-standard interventions remain challenging.

Hence, it is evidenced that the portable POC device of the present invention performs the detection of pathogen associated nucleic acid, producing test results with specificity and sensitivity compatible with acceptable gold standards without involving the conventionally used expensive instruments and skilled human resources. Additionally, integration of smartphone app based analysis and result display further obviates manual interpretation and ensures data dissemination and sharing to benefit public health intervention. Thus, the present invention provides a low cost portable platform to achieve the desired task and is a disruptive replacement to PCR machines that act as traditional benchmark thermal control units in nucleic acid based testing.

The invention claimed is:

1. A portable point of care (POC) based device for piecewise detection of pathogenic infection via nucleic acid based testing of samples comprising:

a portable housing of scalable dimensions supporting a modular and scalable thermal control cum reaction unit (2) for accommodating required number of test reactions to be run in parallel including at least one microcontroller based isothermal heating unit comprising of a heating block, micro-heater, temperature sensor, heat-sink fan assembly, microcontroller and optocoupler-relay unit;

said portable housing of scalable dimensions supporting a modular and scalable thermal control cum reaction unit (2) having guide means for seamless integration therein and therebetween of (i) at least one movable reaction microchamber (4) carrier including a cartridge carrier for carrying at least one movable reaction microchamber comprising a closed and air tight sealable microchamber including a puncturable base and (ii) a POC detector unit comprising of POC detector carrier supporting a microfluidic paper substrate;

said portable housing of scalable dimensions supporting said modular and scalable thermal control cum reaction unit (2) including guide means for inserting therein said at least one movable reaction microchamber (4) carrier including a cartridge carrier for said at least one movable reaction microchamber for carrying in closed contamination free and in sealed airtight manner its contents including selectively desired samples and reagents including labelled primer and probe sets for seamless integration to a first position in said portable housing of scalable dimensions and on said modular and scalable thermal control cum reaction unit for desired isothermal heating for executing piecewise-isothermal reaction steps of the contents in said at least one movable reaction microchamber (4) selectively for carrying out in said at least one movable reaction microchamber anyone or more of (a) RNA containing test sample conditioning (b) reverse transcription to c-DNA including its amplification, and (c) complementary DNA-probe hybridization in said at least one movable reaction microchamber (4) to generate desired reaction product including DNA-probe hybridized reaction product in said at least one movable reaction microchamber;

said portable housing of scalable dimensions further including an on-line dispenser mechanism (5) adapted to cooperate for dispensing the generated desired reaction product including DNA-probe hybridized thermal reaction products from said at least one movable reaction microchamber onto said POC detector unit comprising of microfluidic paper substrate when placed thereunder said at least one movable reaction microchamber inside said portable housing of scalable dimensions;

said portable housing of scalable dimensions having further guide means for carrying said at least one movable reaction microchamber (4) carrier post said selectively controlled isothermal heating piecewise of the said at least one movable reaction microchamber and carrying the generated desired reaction product including DNA-probe hybridized thermal reaction products therein to a second position within said portable housing of scalable dimensions under said on-line dispenser mechanism (5)

said portable housing of scalable dimensions including said modular and scalable thermal control cum reaction unit (2) also having guide means for inserting therein and seamlessly integrating of said POC detector means carrier for moving in a POC detector means within said portable housing of scalable dimensions and thereunder any said at least one movable reaction microchamber disposition in said second position within said portable housing of scalable dimensions post said selectively controlled isothermal heating piecewise of the samples and reagents in said at least one movable reaction microchamber and having the generated desired reaction product including DNA-probe hybridized thermal reaction products therein;

said on-line dispenser mechanism (5) including puncturing needle valve for puncturing of said puncturable base of said movable reaction microchamber and thereby on-line sequentially dispensing of the amplified and labelled cDNA product and/or test reagents as said generated reaction product including DNA-probe hybridized thermal reaction products from said at least one movable reaction microchamber disposition in its said second position onto said microfluidic paper substrate of said POC detector unit;

said POC detector unit comprising of said microfluidic paper substrate including selectively functionalized surface plasmon resonating nano materials and immobilized bio-conjugates for colorimetric detection thereon outside of said movable reaction microchamber and its related online image acquisition of the colorimetric changes in said microfluidic paper substrate involving said selectively functionalized with surface plasmon resonating nano materials and immobilized bio-conjugates for desired piecewise and contamination free detection of pathogenic infection from reaction products including DNA-probe hybridized thermal reaction products based on samples and reagents based reaction products of respective at least one movable reaction microchamber (4) based samples.

2. The portable POC-based device claimed in claim 1 comprising:
said modular and scalable thermal control cum reaction unit (2) adapted for DNA probe RT lamp reaction as a single user step protocol being scalable including plurality of thermal reaction blocks each including said microcontroller based isothermal heating unit based on the number of tests run in parallel and wherein each said microcontroller based isothermal heating unit comprises microcontroller means including optocoupler relay unit, micro heater, heat sink cooling fan and temperature sensors which operatively connect to a heating block.

3. The POC-based device as claimed in claim 1 wherein said portable housing of scalable dimensions supporting a modular and scalable thermal control cum reaction unit (2) having guide means for seamless integration therein include:
guided rail assembly for placement of said POC detector including colorimetric detectors for colorimetric detection comprising a colorimetric detection unit including an imaging acquisition and analysis means.

4. The portable POC-based device as claimed in claim 3 wherein,
the said colorimetric detection unit including a cartridge carrier cooperating with guide rail assembly within said portable housing of scalable dimensions supporting said modular and scalable thermal control cum reaction unit (2) carrying a microfluidic paper substrate (7) including a first sample introduction region of nitrocellulose filter paper, followed by conjugation section functionalized with surface plasmon nanomaterials, a detection section obtained of cellulose membrane functionalized with streptavidin and anti-FAM antibodies and finally an absorbent pad favouring sequentially:
(a) a sample introducing chamber integrated with a channel body of nitrocellulose filter paper;
(b) binding section immobilized with colloidal nanomaterials conjugated with primary target analytes in channel made of glass fiber material;
(c) detection area on a membrane base including a reaction area adapted for immobilization of specific reaction analytes including a control line for secondary binding; and
(d) waste absorbing section comprising of blotting paper/absorbing material with high absorption quality;
cooperatively integrated for image analytics and dissemination via a smartphone app.

5. The portable POC-based device as claimed in claim 3 wherein, said POC detector means carrier for desired piecewise and contamination free detection including a cartridge carrier include microfluidic paper substrate comprising sequentially:
(a) a sample introducing chamber integrated with a channel body of nitrocellulose filter paper;
(b) binding section immobilized with colloidal nanomaterials conjugated with primary target analytes in channel made of glass fiber material;
(c) detection area on a membrane base including a reaction area adapted for immobilization of specific reaction analytes including a control line for secondary binding; and
(d) waste absorbing section comprising blotting paper/absorbing material with high absorption quality, said binding section including a conjugate section of colloidal gold conjugated Anti-FAM antibody binding with the targeted DNA with amplified dual labelled DNA complex selectively migrating downwards to the said reaction area including immobilized streptavidin and anti-FAM secondary antibodies at a test line and control lines of the strip, respectively while flowing from the sample pad, the amplified DNA complex selectively traversing the test line and binding with the streptavidin for producing the color by the concentration of colloidal gold nanoparticles/nanoshells attached to the same, the free gold nanoparticles/nanoshells-antibody conjugates selectively bypassing the test line and reaching the control line to bind with the immobilized anti-FAM secondary antibodies and producing the color of colloidal nanoparticles/nanoshells.

6. The portable POC-based device as claimed in claim 1 wherein the said modular and scalable thermal control cum reaction unit (2) comprises microcontroller means which includes:
pre-programmable piecewise-isothermal reaction operability options including temperature and duration of heating control means adapted for selectively carrying out sample to result integration for detection of RNA-signatured infection including single step body-fluid to result protocol selectively for (i) pre-conditioning of extracted RNA from sample or RNA directly in any swab/saliva sample containing RNA (ii) isothermally-based simultaneous reverse transcription of RNA followed by c-DNA amplification and (iii) complementary DNA-probe hybridization seamlessly in said reaction microchamber which is operatively connected to optocoupler rely unit, micro heater, heat sink cooling fan and temperature sensors which operatively connect to said heating unit comprising a heating block; and
said POC detector includes means for colorimetric detector include said colorimetric detection unit including a microfluidic paper strip (7) and an image acquisition and analysis means including programmed/pre-set camera properties enabling sample to result including extracted sample RNA to seamless dissemination of test results of said detection of pathogenic infection via nucleic acid based testing.

7. The portable POC-based device as claimed in claim 1 wherein said modular and scalable thermal control cum reaction unit (2) supported in said portable housing of scalable dimensions includes:
selective operability for pre-programmable isothermal reactions including one or more isothermal processes as per the specific test protocol based controlled heating means of said reaction microchamber through said heating unit selectively to a specific temperature for a desired period of time as per the specific test protocol via pre-set thermal protocol including for said pre-conditioning of the said RNA present in any body fluid including swab/saliva test sample involving sample homogenization, breaking of viral capsid and inactivation of enzymes for rendering suitable for subsequent reverse transcription to cDNA, its amplification, and complementary DNA-probe hybridization seamlessly in said reaction microchamber favoring desired specificity and sensitivity of said POC detection.

8. The portable POC-based device as claimed in claim 1 wherein:
said portable housing of scalable dimensions supporting said modular and scalable thermal control cum reaction unit (2) accommodates therein said moveable reaction microchamber (4) and moveable reaction microchamber guide (8) means for introducing piecewise analyte sample and reaction mixture including biotin labelled FIP primers and other primers with the melting temperatures ranging in between 55° C. to 65° C. and selectively target RNA analyte specific gene based DNA probes preferably double modified DNA probes in the microchamber into said thermal control cum reaction unit and cooperative moveable reaction microchamber guide means for carrying said moveable reaction microchamber with amplified final reaction mix to said colorimetric unit for required colorimetric detection in cooperation with a microfluidic paper strip and an imaging acquisition analysis means, all seamlessly integrated for selectively carrying out contamination free (i) RNA containing test sample conditioning (ii) reverse transcription and DNA amplification, (iii) specific DNA-probe hybridization and (iv) dispensing of sample on said microfluidic paper strip and (v) on-line colorimetric detection free of any manual intervention as a stand-alone, low cost portable RT-PCR based testing.

9. The portable POC-based device as claimed in claim 1 comprising:

microchamber cartridge (3) and moveable reaction microchamber guide rail (8) for desired introduction of piecewise analyte sample and reaction mixture containing moveable reaction microchamber into said thermal control cum reaction unit (2) and said POC detector means carrier for desired piecewise and contamination free detection including a cartridge carrier including a microfluidic paper strip (7) comprises selectively functionalized paper-strip including a first sample introduction region of nitrocellulose filter paper, followed by conjugation section functionalized with surface plasmon nanomaterials, a detection section obtained of cellulose membrane functionalized with streptavidin and anti-FAM antibodies and finally an absorbent pad for sequentially executing surface plasmon resonating nanomaterial conjugated complementary analyte binding/hybridization reaction and said imaging acquisition and analysis means comprises smartphone based imaging and analytic means.

10. The POC-based device as claimed in claim 1 comprising:

providing said detection unit (7) in a portable platform for ready coupling to the said portable housing of scalable dimensions supporting therein the modular and scalable thermal control cum reaction unit (2) for microfluidic dispensing of the amplified and labelled c-DNA product and/or test reagents as required involving said on-line dispenser mechanism (5) onto said microfluidic paper based sample pad of the colorimetric detection strip (7) via a seamless fluidic pathway including microfluidic dispenser means.

11. The portable POC-based device as claimed in claim 1 comprising:

said portable housing of scalable dimensions supporting said modular and scalable thermal control cum reaction unit (2) including the said moveable reaction microchamber (4) in a holding cartridge (3) for executing piecewise-isothermal reaction steps with a provision of engaging plurality of moveable reaction microchambers hosting reagents including non-radioactive labelled primer and probe sets, and seamlessly interfacing with the said detection means including functionalized custom-made paper strips (7) including a first sample introduction region of nitrocellulose filter paper, followed by conjugation section functionalized with surface plasmon nanomaterials, a detection section obtained of cellulose membrane functionalized with streptavidin and anti-FAM antibodies and finally an absorbent pad preferentially adsorbed with surface plasmon resonating nanomaterial conjugated analytes as well as other target analytes to orchestrate the binding events.

12. The portable POC-based device as claimed in claim 1 comprising: said portable housing of scalable dimensions supporting said modular and scalable thermal control cum reaction unit (2) includes guide rail assembly for said colorimetric detection unit (7) cooperatively integrated into a portable housing (lab-on-a-box) including:

said modular and scalable thermal control cum reaction unit (2) including at least an isothermal block including a heating platform on which the said microchamber including puncturable base thereof are placed for the test reaction with cooperative heating control circuitry and power supply operatively connected to said isothermal heating block;

said colorimetric detection unit including a cartridge (6) type access for inserting said microfluidic paper substrate/strip including a first sample introduction region of nitrocellulose filter paper, followed by conjugation section functionalized with surface plasmon nanomaterials, a detection section obtained of cellulose membrane functionalized with streptavidin and anti-FAM antibodies and finally an absorbent pad;

said on-line dispenser mechanism for sequentially dispensing the amplified and labelled cDNA product and/ or test reagents as required including puncturing needle valve and dropper for test reagent including LFA buffer, said puncturing needle valve operable for puncturing the base of the moveable reaction microchamber for release of reaction product onto said microfluidic paper substrate/strip and said dropper for controlled dropping of reagents/buffer on said reaction product containing paper substrate/strip; and said image analytics and dissemination section including a smartphone app including for image capture, processing and algorithmic implementation and results display operatively connected to a transparent viewing window (9) for image acquisition of colorimetric changes of the reaction strip on said microfluidic paper substrate.

13. The portable POC-based device as claimed in claim 1 to comprising at least:

one movable reaction microchamber holding cartridge supporting the at least one movable reaction microchambers adapted to be movable through a guided rail (8) synchronized with said cartridge-based feeding of microfluidic paper substrate (7) including a first sample introduction region of nitrocellulose filter paper, followed by conjugation section functionalized with surface plasmon nanomaterials, a detection section obtained of cellulose membrane functionalized with streptavidin and anti-FAM antibodies and finally an absorbent pad in the said sample-introducing chamber of the said colorimetric detection unit whereby the moveable reaction microchamber is adapted to be placed in between a fluid dispenser and the sample introducing chamber of the said colorimetric detection unit for the release of the solution onto the said microfluidic paper substrate whereby the sample could flow through the paper substrate matrices due to the capillary action by the force of surface tension and reach out to the detection area through the conjugate section.

14. The portable POC-based device as claimed in claim 1 comprising:
    said moveable reaction microchambers include closed contamination free reaction chamber with a dispensing mechanism fitted with the reaction chamber adapted to be actuated manually and/or automatically to dispense the final product seamlessly onto the microfluidic sample pad of a 'protected' LFA strip internally encapsulated within a transparent polymer made cassette via feedable via a movable cartridge.

15. The portable POC-based device as claimed in claim 1 comprising: smartphone (10) based image capturing and application including pathogen-specific training image data sets adapted for analyzing exclusive properties mapped to the upstream experimental significance and eventually the decision making based on the analysis offers with unique features integrated for subsequently analyzing the same and displaying the final results onto the smartphone screen enabling colorimetric detection step on said microfluidic paper platform (7) within 10 minutes, after about 5-10 minutes of sample introduction into the paper strip.

16. The portable POC-based device as claimed in claim 1 which is selectively,
    (a) scalable based on number of test samples in plurality of moveable reaction microchambers in said thermal control cum reaction unit
    (b) said thermal control cum reaction unit and said colorimetric detection unit adapted for modular integrated cooperation and/or stand-alone independent modules (c) portable lab-in-box.

17. The portable POC-based device as claimed in claim 1 wherein, said at least one movable reaction microchamber (4) hosts desired samples and reagents including labelled primer and probe sets for executing piecewise-isothermal reaction steps having high specificity of detection involving correspondingly standardized and customized primers against individual gene target regions including target regions of SARS-CoV-2 genome, influenza-A which is free of any cross-reactivity other than the target genome sequences with said detector unit including microfluidic paper platform with nitrocellulose membrane having corresponding specific immobilized complementary bio-conjugates including specific reaction analyte therein.

18. The portable POC-based device as claimed claim 1 having high specificity of detection of gene target regions of SARS CoV-2 genome involving set of six RT-LAMP primers specifically selective for each gene set (SEQ. ID No. 1-6 for ORF1B, SEQ. ID No. 10-15 for N gene, SEQ. ID No. 19-24 for E gene, SEQ. ID No. 28-33 for RNase P) ensuring free of cross reactivity towards SARS-CoV, MERS and other human coronavirus genome sequences.

19. The portable POC-based device as claimed in claim 1 as adapted for complementary DNA probe hybridization for additional enhancement of specificity of detection including labelled probes (BLP Probe SEQ.ID No. 7 for ORF1B, BLP Probe SEQ.ID No. 16 for N gene, BLP Probe SEQ.ID No. 25 for E gene and BLP Probe SEQ.ID No. 34 for RNase P) which specifically bind with the RT-LAMP products amplified involving RT-LAMP primers with no non-specific signal in the negative control sets.

20. The portable POC-based device as claimed in claim 1 wherein,
    said microcontroller based isothermal heating unit (2), operatively connected to carry out microcontroller-controlled isothermal heating of at least one moveable reaction microchamber (4) including as said master mix comprising the reverse-transcription cum isothermal amplification reagents and the dual modified (5'-FAM and 3' ddNTP) specific complementary DNA probe selected from Seq. ID No. 8 for ORF1B, Seq.ID No. 17 for N gene and Seq.ID No. 26 for E gene along with the RNA sample of the analyte;
    said microfluidic paper substrate based detector unit having a binding section including a conjugate section of colloidal nanoparticle/nanoshell and complementary bio-conjugates including specific reaction analyte therein binding with the targeted DNA with amplified dual labelled DNA complex thus enabled for selectively migrating downwards to the said reaction area including therein said immobilized complementary bio-conjugates including specific reaction analyte comprising streptavidin and anti-FAM secondary antibodies at a test line and control lines of the strip, respectively while flowing from the microfluidic paper substrate based sample pad, the amplified DNA complex selectively traversing the test line and binding with a specific immobilized bio-conjugates including specific reaction analyte comprising streptavidin for producing the color by the concentration of colloidal nanoparticles/nanoshells attached to the same, the free nanoparticles/nanoshells-analyte conjugates selectively bypassing the test line and reaching the control line to bind with the immobilized bio-conjugates including specific reaction analyte therein and producing the color of colloidal nanoparticles/nanoshells thereby said detector unit including said selectively functionalized with surface plasmon resonating nano materials and immobilized bio-conjugates adapted for automatically executing the combined reaction protocol in a concomitant manner and provide required integration of all the reactions necessary for the test as a pre-programmable, customizable, single user-step close tube piecewise isothermal steps to avoid any intermediate user intervention and chance of carryover contamination.

* * * * *